(12) United States Patent
Moller et al.

(10) Patent No.: US 6,492,495 B1
(45) Date of Patent: Dec. 10, 2002

(54) PTP-S31: A NOVEL PROTEIN TYROSINE PHOSPHATASE

(75) Inventors: Niels Peter Hundahl Moller; Karin Bach Moller, both of Munich; Axel Ullrich, Martinsried bei Munich, all of (DE)

(73) Assignee: Max-Planck-Gesellschaft zur Forderung der Wissenschaften e.V., Gottingen (DE)

( * ) Notice: Subject to any disclaimer, the term of this patent is extended or adjusted under 35 U.S.C. 154(b) by 0 days.

(21) Appl. No.: 09/361,096

(22) Filed: Jul. 26, 1999

Related U.S. Application Data

(62) Division of application No. 08/449,609, filed on May 24, 1995, now Pat. No. 5,952,212, which is a division of application No. 08/036,210, filed on Mar. 23, 1993, now Pat. No. 5,585,233.

(51) Int. Cl.[7] .............................................. C07K 16/00
(52) U.S. Cl. ................................ 530/387.9; 530/388.26
(58) Field of Search .......................... 530/387.9, 388.26

(56) References Cited

FOREIGN PATENT DOCUMENTS

| WO | WO-9201050 A1 | * | 1/1992 |
| WO | 94/21800 | | 9/1994 |

OTHER PUBLICATIONS

Hooft van Huijsduijnen, R., Gene 225:1–8, 1998.*
Charbonneau and Tonks, "1002 Protein phosphatases?", Ann. Rev. Cell. Biol. 8:463–493 (1992).
Charbonneau, et al., "Human placenta protein–tyrosine–phosphatase: Amina acid sequence and relationship to a family of receptor–like proteins", Proc. Natl. Acad. Sci. USA 86:5252–5256 (1989).
Chernoff, et al., "Cloning of a cDNA for a major human protein–tyrosine–phosphatase", PNAS US 87:2735–2739 (1990).
Cool, et al., "cDNA isolated from a human T–cell library encodes a member of the protein–tyrosine–phosphatase family", Proc. Natl. Acad. Sci. USA 86:5257–5261 (1989).
Fantus, et al., "Pervanadate [Peroxide(s) of vanadate] mimics insulin action in rat adipocytes via activation of the insulin receptor tyrosine kinase", Biochem. 28:8864–8871 (1989).
Fischer, et al., "Protein tyrosine phosphatases: A diverse family of intracellular and transmembrane enzymes", Science 253:401–406 (1991).
Freeman, et al., "Identification of a human src homology 2–containing protein–tyrosine–phosphatase: A putative homolog of *Drosophila corkscrew*", Proc. Natl. Acad. Sci. USA 89:11239–11243 (1992).
Gebbink, et al., "Cloning, expression and chromosomal localization of a new putative receptor–like protein tyrosine phosphatase", FEBS Lett. 290:123–130 (1991).

Gu, et al., "Identification, cloning, and expression of a cytosolic megakaryocyte protein–tyrosine–phosphatase with sequence homology to cytoskeletal protein 4.1", Proc. Natl. Acad. Sci. USA 88:5867–5871 (1991).
Guan, et al., "Cloning and expression of a protein–tyrosine–phosphatase", Proc. Natl. Acad. Sci. USA 87:1501–1505 (1990).
Hariharan, et al., "Cloning and characterization of a receptor–class phophotyrosine phosphatase gene expressed on central nervous system axons in *Drosophila melanogaster*", Proc. Natl. Acad. Sci. USA 88:11266–11270 (1991).
Hunter, "A tail of two src's: *Mutatis mutandis*", Cell 49:1–4 (1987).
Hunter, "Protein–tyrosine phosphatases: The other side of the coin", Cell 58:1013–1016 (1989).
Itoh, et al., "Purification and characterization of the catalytic domains of the human receptor–linked protein tyrosine phosphatases HPTP beta, leukocyte common antigen (LCA), and leukocyte common antigen–related molecular (LAR)", J. Biol. Chem. 267:12356–12363 (1992).
Jirik, et al., "Cloning and chromosomal assignment of a widely expressed human receptor–like protein–tyrosine phosphatase". FEBS Lett. 273:239–242 (1990).
Jirik, et al., "Cloning of a novel receptor–like protein tyrosine phosphatase from a human hepatoblastoma cell line", FASEB J. 4A:2082 (Abstr. 2253) (1990).
Kaplan, et al., "Cloning of three human tyrosine phosphatases reveals a multigene family of receptor–linked protein–tyrosine–phosphatases expressed in brain", Proc. Natl. Acad. Sci. USA 87:7000–7004 (1990).
Krueger, et al., "Structural diversity and evolution of human receptor–like protein tyrosine phosphatases", EMBO J. 9:3241–3252 (1990).
Lombroso, et al., "Molecular characterization of a protein–tyrosine–phosphatase enriched in striatum", Proc. Natl. Acad. Sci. USA 88:7242–7246 (1991).
Margolis, et al., "EGF induced tyrosine phosphorylation of phospholipase C–II: A potential mechanism for EGF receptor signaling", Cell 57:1101–1107 (1989).

(List continued on next page.)

*Primary Examiner*—Patrick J. Nolan
(74) *Attorney, Agent, or Firm*—Foley & Lardner

(57) ABSTRACT

A novel protein tyrosine phosphatase designated PTP-S31 and its subfamily are identified, as are nucleic acid molecule coding therefor. Included in this;family are PTP-S31 proteins or glycoproteins having one, two, or three identified amino acid changes in previously defined consensus sequences in the catalytic phosphatase domains of known protein tyrosine phosphatases. The PTP-S31 proteins or glycoproteins may be produced by recombinant means. Antibodies to PTP-S31 proteins or glycoproteins and nucleic acid constructs coding therefor, and methods for screening molecules which can bind to PTP-S31 proteins or glycoproteins and inhibit or stimulate their enzymatic activity, are provided.

9 Claims, 29 Drawing Sheets

OTHER PUBLICATIONS

Matthews, et al., "Characterization of hematopoietic intracellular protein tyrosine phosphatases: Description of a phosphatase containing an SH2 domain and another enriched in proline—, glutamic acid—, serine—, and threonine–rich sequences", Mol. Cell. Biol. 12:2396–2405 (1992).

Matthews, et al., "Identification of an additional member of the protein–tyrosine–phosphatase family: Evidence for alternative splicing in the tyrosine phosphatase domain", Proc. Natl. Acad. Sci. USA 87:4444–4448 (1990).

Miyajima, et al., "Cytokine receptors and signal transduction", Ann. Rev. Immunol. 10:295–331 (1992).

Morla, et al., "Reversible tyrosine phosphorylation of cdc2–Dephosphorylation accompanies activation during entry into mitosis", Cell 58:193–203 (1989).

Mustelin, et al., "Rapid activation of the T–cell tyrosine protein kinase pp56lck by the CD45 phophotyrosine phophatase", Proc. Natl. Acad. Sci. USA 86:6302–6306 (1989).

Ohagi, et al., "Sequence of a cDNA encoding human LRP (leukocyte common antigen–related peptide)", Nucl. Acids Res. 18:7159 (1990).

Ostergaard, et al., "Expression of CD45 alters phosphorylation of the lck–encoded tyrosine protein kinase in murine lymphoma T–cell lines", Proc. Natl. Acad. Sci. USA 86:8959–8963 (1989).

Pallen, et al., "Purification of a phosphotyrosine phosphatase that dephosphorylates the epidermal growth factor receptor autophosphorylation sites", Ann. N.Y. Acad. Sci. 551:299–308 (1988).

Patthy, "Homology of a domain of the growth hormone/prolactin receptor family with type III modules of fibronectin", Cell 61:13–14 (1990).

Plutzky, et al., "Isolation of a src homology 2–containing tyrosine phosphatase", Proc. Natl. Acad. Sci. USA 89:1123–1127 (1992).

Pot and Dixon, "A thousand and two protein tyrosine phosphatases", Biochem. Biophys. Acta. 1136:35–43 (1992).

Ralph, et al., Structural variants of human T200 glycoprotein (leukocyte common antigen), EMBO J. 6:1251–1257 (1987).

Shen, et al., "A protein–tyrosine phosphatase with sequence similarity to the SH2 domain of the protein–tyrosine kinases", Nature 352:736–739 (1991).

Shier and Watt, "Primary structure of a putative receptor for a ligand of the insulin family", J. Biol. Chem. 264:14605–14608 (1989).

Stover, et al., "Protein–tyrosine–phosphatase CD45 is phosphorylated transiently on tyrosine upon activation of Jurkat T cells", Proc. Natl. Acad. Sci. USA 88:7704–7707 (1991).

Streuli, et al., "A family of receptor–like protein tyrosine phosphatases in humans and Drosophila", Proc. Natl. Acad. Sci. USA 86:8698–8702 (1989).

Streuli, et al., "A new member of the immunoglobulin super–family that has a cytoplasmic region homologous to the leukocyte common antigen", J. Exp. Med. 168:1523–1530 (1988).

Streuli, et al., "Distinct functional roles of the two intracellular phosphatase like domains of the receptor–linked protein tyrosine phosphatases LCA and LAR", EMBO Journal 9:2399–2407 (1990).

Takekawa, et al., "Cloning and characterization of a human cDNA encoding a novel putative pyroplasmic protein–tyrosine–phosphatase", Biochem. Biophys. Res. Commun. 189(2):1223–1230 (1992).

Tonks, et al., "CD45, an integral membrane protein tyrosine phosphatase", J. Biol. Chem. 265:10674–10680 (1990).

Tonks, et al., "Purification of the major protein–tyrosine–phosphatases of human placenta", J. Biol. Chem., 263:6722–6730 (1988).

Tsai, et al., "Isolation and characterization of temperature–sensitive and thermostable mutants of the human receptor–like protein tyrosine phosphatase LAR", J. Biol. Chem. 266(16):10534–10543 (1991).

Ullrich, et al., "Insulin–like growth factor I receptor primary structure: comparison with insulin receptor suggests structural determinants that define functional specificity", EMBO J. 5:2502–2512 (1986).

Yang and Tonks, "Isolation of a cDNA clone encoding a human protein–tyrosine phosphatase with homology to the cytoskeletal–associated proteins band 4.1, ezrin, and talin", Proc. Natl. Acad. Sci. USA 88:5949–5953 (1991).

Yi, et al., "Protein tyrosine phosphatase containing SH2 domains: Characterization, preferential expression in hemaotpoietic cells, and localization to human chromosome 12p12–p13", Mol. Cell. Biol. 12:836–846 (1992).

* cited by examiner

```
  1  gaaaccagagcaaaaacattagtaatgctaacacagtgtttgaaaaaggacggatcaga    60
  1  E  T  R  A  K  T  L  V  M  L  T  Q  C  F  E  K  G  R  I  R    20

61  tgccatcagtattggccagaggacaacaagccagttactgtctttggagatatagtgatt  120
 21  C  H  Q  Y  W  P  E  D  N  K  P  V  T  V  F  G  D  I  V  I    40

121  acaaagctaatggaggatgttcaaatagattggactatcaggatctgaaaattgaaagg  180
 41  T  K  L  M  E  D  V  Q  I  D  W  T  I  R  D  L  K  I  E  R    60

181  catggggattgcatgactgttcgacagtgtaactttactgcctggccagagcatgggtt   240
 61  H  G  D  C  M  T  V  R  Q  C  N  F  T  A  W  P  E  H  G  V    80

241  cctgagaacagcgcccctctaattcactttgtgaagttggttcgagcaagcaggcacat  300
 81  P  E  N  S  A  P  L  I  H  F  V  K  L  V  R  A  S  R  A  H   100

301  gacaccacctatgattgtt                                            321
101  D  T  T  P  M  I  V                                           107
```

FIG. 1

```
  1 ETRAKTLVMLTQCFEKGRIRCHQYWPEDNKPVTVFGD...IVITKLMEDVQ  48
    ::.:.:|||.:||.:.:||.:||.:|:.:  ::  :|::.:|:
 -- EQKSRGVVMLNRVMEKGSLKCAQYWPQKEEKEMIFEDTNLKLTLISEDIK 150

49 IDWTIRDLKIERHG..DCMTVRQCNFTAWPEHGVPENSAPLIHFVKLVR.  95
    .:|.:|:.|:..:.  ||.|:|||:|.|:|:|||||:|.:.:|:|:|:|
151 SYYTVRQLELENLTTQETREILHFHYTTWPDFGVPESPASFLNFLFKVRE 200

96 .ASRAHDTTPMIV..................................... 107
     :|:..:  .|::.|
201 SGSLSPEHGPVVHCSAGIGRSGTFCLADTCLLLMDKRKDPSSVDIKKVL  250
```

FIG. 2

```
1    tatttagcttgggaagtaatacgggatatttaactccttgggtttgaaaccatgt          60

61   cattatgagatgaggccaataagcaagaaatccttcctgcaacatgttgaagagctttg     120
21      M  R  M  R  P  I  S  K  K  S  F  L  Q  H  V  E  E  L  C      40

121  cacaaacaacaacctaaagtttcaagaagaaTTTTCGGAATTACCAAAATTTCTTCAGGA    180
41    T  N  N  L  K  F  Q  E  E  F  S  E  L  P  K  F  L  Q  D       60

181  TCTTTCTTCAACTGATGCTGATCTGCCCTTGGAATAGAGCAAAAAACCGCTTCCCAAACAT   240
61    L  S  S  T  D  A  D  L  P  W  N  R  A  K  N  R  F  P  N  I    80

241  AAAACCATATAATAACAGAGTAAAGctgatagctgacgctagtgttccaggttcgga      300
81    K  P  Y  N  N  N  R  V  K  L  I  A  D  A  S  V  P  G  S  D   100

301  ttatattaatgccagctatatttctgttattatgtccaaatgaatttattgctactca     360
101   Y  I  N  A  S  Y  I  S  G  Y  L  C  P  N  E  F  I  A  T  Q   120

361  aggtccactaccaggaacagttggagattttggagaatggtgtgggaaaccagagcaaa    420
121   G  P  L  P  G  T  V  G  D  F  W  R  M  V  W  E  T  R  A  K   140

421  aacattagtaatgctaacacagtgttttgaaaaggacgatcagatgccatcagtattg      480
141   T  L  V  M  L  T  Q  C  F  E  K  G  R  I  R  C  H  Q  Y  W   160

481  gccagaggacaacaagccagtctctttggagatatagtgattacaaagctaatgga       540
161   P  E  D  N  K  P  V  T  V  F  G  D  I  V  I  T  K  L  M  E   180
```

FIG. 3A

```
541  ggatgttcaaatagattggactatcaggatctgaaaattgaaaggcatgggattgcat  600
181    D  V  Q  I  D  W  T  I  R  D  L  K  I  E  R  H  G  D  C  M   200

601  gactgttcgacagtgtaacttactgcctgccagagcatgggttcctgagacagcgc    660
201    T  V  R  Q  C  N  F  T  A  W  P  E  H  G  V  P  E  N  S  A   220

661  ccctctaattcactttgtgaagttggttcgagcaagcaggcacacatgacaccacctat  720
221    P  L  I  H  F  V  K  L  V  R  A  S  R  A  H  D  T  T  P  M   240

721  gattgttcactgcaggcacagtatatcttttacaccagtgccattctgatctcttatca  780
241    I  V  H  C  R  H  S  I  S  F  Y  T  S  A  F  W  I  S  Y  Q   260

781  aataagggaagtaatcagcccatctgttttgttaactattcagcacttcagaagatggac  840
261    I  R  E  V  I  S  P  S  V  L  L  T  I  Q  H  F  R  R  W  T   280

841  tctttggacgccatggaaggtgatgttgagcttgatgtttaatggaagaaccactatgtaaata  900
281    L  W  T  P  W  K  V  M  L  S  L  N  G  K  K  P  L  C  K  Y   300

901  ttcagaccaaaggatacaattggaagagattttaaatcccaggggccaagttacccc    960
301    S  D  Q  R  I  Q  L  E  E  I  F  K  S  Q  G  P  P  K  L  P  P   320

961  tcattcttccgaattgaatgtgcaacctaaagaaatatctatgtcttctcactgtgc    1020
321    H  S  S  E  L  K  C  A  T  L  K  K  Y  L  C  F  S  H  C  A    340

1021 ctttccaaacgattgaacattttaagactagttcttgaaatagctaatacagaataat    1080
341    F  P  N  G  L  N  I  L  R  L  V  L  E  N  S  *               355
```

FIG. 3B

```
1081  tatttgttttgtacagaataaatattatgcatttaaatgcttaagaaaagacatcccat  1140
1141  atgtttttgaagtcctccatatttggaataagccaaatagaaaattattattatattag  1200
1201  cattaatgttcaatgtgaatttccctatgtattggatttaatttgaggacaaaagtt   1260
1261  gtaaatgttgattcagtagtgttgttttggcttacagggtattgatgttcttgtgata   1320
1321  atttccaggactgtcataatgatctgtacttccatgtacacccctgttttgaatcctc   1380
1381  tgttttatgagtgctgagatatcatctcatgatcccgaacagctgaacagtaacccctg  1440
1441  acactgcagggattacttggcctttatacaacacagtagctcttcaggacacttagg   1500
1501  gctatttaatttcgattgtgtcttcagtttgagaaccttaaaagaaaattaaagtgcaa  1560
1561  ttgcacacatgaaattacagagtaccattctagcaaacctacatttgtaactttaaaac  1620
1621  acaagttttxcccctgtattgtatattcaaatatatagtaaatgtatcagagtatttgc  1680
```

FIG. 3C

| | | |
|---|---|---|
| 1681 | ccattagatgatcaacctaatattaacattctgaagagtttcttcagcaaaatgta | 1740 |
| 1741 | tcaagagtaataaaacactgtgcgtgtttcaagcttgtaaaccaatgatctgctgt | 1800 |
| 1801 | ggtgccaacagagacttccaaatggattatgttaaatggccgtcatttcccaagg | 1860 |
| 1861 | ttgattttgagcagtatacttggtggaactgaaaacaaagaaattaaccatctatagcaa | 1920 |
| 1921 | attcaaggtttctttatagaaatctttcagcctccatcttattaaatagtgacaatgtg | 1980 |
| 1981 | gtaagttttgaattatatgaactcattttgtcatagattcaattaagagtaataaatag | 2040 |
| 2041 | tattaattatgctcttctatgataagaagtatatctttatgcttattccgctggaacata | 2100 |
| 2101 | tatatatatgaaatgctatggccaataaaattgaattttaatgaaaaaaaaaaaaa | 2160 |
| 2161 | aaaaaaaaaaaa | 2173 |

FIG. 3D

```
  1  MRMRPISKKSFLQHVEELCTNNNLKFQEEFSELPKFLQDLSSTDADLPWN   50
     ::   ::   :: :  ::  ::   ::: :  :  : : ::
  1  .........MEMEKEFEQI..DKSGSWAAIYQDIRHEASDFPCRVAKLPKN   40

51  RAKNRFPNIKPYNNNRVKLIADASVPGSDYINASYISGYLCPNEFIATQG   100
     ::  :: ::   : :: ::  :  :::::::  :::       :::::
 41  KNRNRYRDVSPFDHSRIKLHQE.....DNDYINASLIKMEEAQRSYILTQG   86

101  PLPGTVGDFWRMVWETRAKTLVMLTQCFEKGRIRCHQYWPEDNKPVTVFG   150
     ::: : ::::: :: :::::   :::::: ::  ::::: :::
 87  PLPNTCGHFWEMVWEQKSRGVVMLNRVMEKGSLKCAQYWPQKEEKEMIFE   136

151  D..IVITKLMEDVQIDWTIRDLKIERHG...DCMTVRQCNFTAWPEHGVPE   196
        ::: ::  ::: :: :: ::::       ::: :  ::: :: :::
137  DTNLKLTLISEDIKSYYTVRQLELENLTTQETREILHFHYTTWPDFGVPE   186
```

FIG. 4A

```
197  NSAPLIHFVKLVR..ASRAHDTTPMIVHCRHSI.......SFYTSAFWISY  238
      ..::.::--.::...:::.::::::.--..:::
187  .SPASFLNFLFKVRESGSLSPEHGPVVVHCSAGIGRSGTFCLADTCLLLMD  236

239  QIREVIS...PSVLLTIQHFRRWTLWTPWKVMLSLNGKKPLCKY.......  279
      ::.::...:.:...::.:.:.::...::::...
237  KRKDPSSVDIKKVLLEMRKFRMGLIQTADQLRFSYLAVIEGAKFIMGDSS   286

280  .SDQRIQL.EEIFKSQGPKLPPHSSELKCATLKKYLCFSHCAFPNGLNIL.  327
      :.:.:--.:::..:::::...::.::.:::..:--
287  VQDQWKELSHEDLEPPPEHIPPPPRPPK.RILEPHNGKCREFFPNHQWVK   335

328  RLVLENS...........................................  334
      .:.--
336  EETQEDKDCPIKEEKGSPLNAAPYGIESMSQDTEVRSRVVGGSLRGAQAA   385
```

FIG. 4B

```
  1  acaacaagccagttactgtctttggagatatagtgattacaaagctaatggaggatgttc   60
  1   N  K  P  V  T  V  F  G  D  I  V  I  T  K  L  M  E  D  V  Q   20

61  aaatagattggactatcagggatctgaaaattgaaaggcatgggattgcatgactgttc  120
 21   I  D  W  T  I  R  D  L  K  I  E  R  H  G  D  C  M  T  V  R   40

121  gacagtgtaactttactgcctggccagagcatgggggttcctgagaacagcgcccctctaa  180
 41   Q  C  N  F  T  A  W  P  E  H  G  V  P  E  N  S  A  P  L  I   60

181  ttcactttgtgaagttggttcgagcaaggcacagcaccacacctatgattgttc  240
 61   H  F  V  K  L  V  R  A  S  R  A  H  D  T  P  M  I  V  H   80

241  actgcagtgctggagttggaagaaactggagttttattgctctgaccatttaacacaac  300
 81   C  S  A  G  V  G  R  T  G  V  F  I  A  L  D  H  L  T  Q  H  100
```

FIG. 5A

```
301  atataaatgaccatgattttgtggatatatggactagtgctgaactgagaagtgaaa   360
101   I   N   D   H   D   F   V   D   I   Y   G   L   V   A   E   L   R   S   E   R   120

361  gaatgtgcatggtgcagaatctggcacagtatatctttttacaccagtgcattctggatc   420
121   M   C   M   V   Q   N   L   A   Q   Y   I   F   L   H   Q   C   I   L   D   L   140

421  tcttatcaaataaggaagtaatcagcccatctgtttgttaactattcagcacttcaga    480
141   L   S   N   K   G   S   N   Q   P   I   C   F   V   N   Y   S   A   L   Q   K   160

481  agatggactctttggacgccatggaaggtgatgttgagcttgaatgggaaga          532
161   M   D   S   L   D   A   M   E   G   D   V   E   L   E   W   E         177
```

FIG. 5B

```
  1     tatttagcttggaagtaatacgggatatttaaactccttggggtttgaaaccatgt          60

61     cattatgagaatgaggccaataagcaagaaatccttcctgcaacatgttgaagagctttg      120
 21      M   R   M   R   P   I   S   K   K   K   S   F   L   Q   H   V   E   E   L   C    40

121     cacaaacaacaacctaaagtttcaagaagaaTTTTCGAATTACCAAAATTTCTTCAGGA       180
 41      T   N   N   N   L   K   F   Q   E   E   F   S   E   L   P   K   F   L   Q   D    60

181     TCTTTCTTCAACTGATGCTGATCTGCCTTGGAATAGAGCAAAAAACCGCTTCCCAAACAT      240
 61      L   S   S   T   D   A   D   L   P   W   N   R   A   K   N   R   F   P   N   I    80

241     AAAACCATATAATAACAGAGTAAAGctgatagctgacgctagtgttccaggttcgga        300
 81      K   P   Y   N   N   N   R   V   K   L   I   A   D   A   S   V   P   G   S   D   100

301     ttatattaatgccagctatatttctgttattatgtccaatgaattattgctactca         360
101      Y   I   N   A   S   Y   I   S   G   Y   L   C   P   N   E   F   I   A   T   Q   120

361     aggtcccactaccaggaacagttggagatttttgaaaaaggaacagagcaaa             420
121      G   P   L   P   G   T   V   G   D   F   W   R   M   V   W   E   T   R   A   K   140

421     aacattagtaatgctaacacagtgttcggagatatagtgattacaaagctaattg          480
141      T   L   V   M   L   T   Q   C   F   E   K   G   R   I   R   C   H   Q   Y   W   160

481     gccagaggacaacaagccagtgtcactgtctttggagatatagtgattacaaagctaatgga    540
161      P   E   D   N   K   P   V   T   V   F   G   D   I   V   I   T   K   L   M   E   180

541     ggatgttcaaatagattggactatcaggatcctgaaaattgaaaggcatggggattgcat     600
181      D   V   Q   I   D   W   T   I   R   D   L   K   I   E   R   H   G   D   C   M   200
```

FIG. 6A

| | | |
|---|---|---|
| 601<br>201 | gactgttcgacagtgtaacttactgcctggccagagcatgggttcctgagaacagcgc<br>T V R Q C N F T A W P E H G V P E N S A | 660<br>220 |
| 661<br>221 | ccctctaattcactttgtgaagttggttcgagcaaggcacatgacaccacacctat<br>P L I H F V K L V R A S R A H D T T P M | 720<br>240 |
| 721<br>241 | gattgttcactgcagtgctgctggagttggaagaactggagttttattgctctggaccattt<br>I V H C S A G V G R T G V F I A L D H L | 780<br>260 |
| 781<br>261 | aacacaacatataaatgaccatgattttgtggatatatatggactagtagctgaactgag<br>T Q H I N D H D F V D I Y G L V A E L R | 840<br>280 |
| 841<br>281 | aagtgaaagaatgtgcatggtgcagaatctggcacagtatatctttttacaccagtgcat<br>S E R M C M V Q N L A Q Y I F L H Q C I | 900<br>300 |
| 901<br>301 | tctggatctcttatcaaataaggaagtaatcagcccatctgttttgttaactattcagc<br>L D L L S N K G S N Q P I C F V N Y S A | 960<br>320 |
| 961<br>321 | acttcagagatgactctttggacgccatgaaggtgattgttgagcttgaatgggaaga<br>L Q K M D S L D A M E G D V E L E W E E | 1020<br>340 |
| 1021<br>341 | aaccactatgtaaatattcagaccaaaggatacaattggaagagattttaaatcccagg<br>T T M * | 1080<br>343 |
| 1081 | ggccaaagttaccccctcattcttccgattgaaatgtgcaacctaaagaatatctat | 1140 |
| 1141 | gcttctctcactgtgcctttccaaacgattgaacatttaagactagttcttgaaaata | 1200 |

FIG. 6B

```
1201  gctaatacagaataattatttgtacagaataatattatgcattttaaatgctta    1260
1261  agaaaagacatcccatatgttttttgaagtcctccatatttttgaataagccaaatagaaa  1320
1321  attattattatattagcattaatgtttcaatgtttccctatgtattggatttaat  1380
1381  tttgaggacaaaagttgtaaatgttgattcagtagtgttgttttggcttacagggtattg  1440
1441  atgtttcttgtggataatttccaggactgtcataatgatctgtacttccatgtacacccc  1500
1501  tgtgttttgaatcctctgttttatgagtgctgagatatcatctcatgatcccgaacagct  1560
1561  gaacagtaacccctgacactgcaggattactggcctttatacaacacagtagctc  1620
1621  ttcagggacacttaggctatttaattcgattgtcttcagtttgagaccttaaaag  1680
1681  aaaattaaaagtgcaattgcacacatgaaattacagagtaccattctagcaaacctacat  1740
1741  ttgtaacttttaaaacacaagttttxcccctgtattgtattcaaatatatagtaaat  1800
```

FIG. 6C

| | | |
|---|---|---|
| 1801 | gtatcagagtatttgcccattagatatgatcaacctaatattaacaattctgaagagttt | 1860 |
| 1861 | cttcagcaaaatgtatcaagagtaataaaacactgtgcgtgtttcagcttgtaaacc | 1920 |
| 1921 | aatgatctgctgtgtggtgccaacagagacttccaaatggattatgttaaatggccgtc | 1980 |
| 1981 | atttcatttcccaaggttgattttgagcagtatacttggtggaactgaaaacaaagaaat | 2040 |
| 2041 | taaccatctatagcaaattcaagtttctttatagaaaatctttcagcctccatcttatt | 2100 |
| 2101 | aaatagtgacaatgtggtaagttttgaattatatgaactcattttgtcatagatttcaat | 2160 |
| 2161 | taagagtaataaatagtattaattatgctcttctatgataagaagtatatcttatgctta | 2220 |
| 2221 | tttccgctggaacatatatatatgaaatgctatggccaataaaattgaattttaatga | 2280 |
| 2281 | aaaaaaaaaaaaaaaaaaaaaaaaaaa | 2309 |

FIG. 6D

```
CD45-D1     MNVEP-IHADILLETYKRKIADEGRLFLAEFQSIPRVFSKFPIKEARKPFNQNKNRYVDI
LAR-D1      MRDHPPIPITDLADNIERLKANDGLKFSQEYESIDPG-QQFTWENSNLEVNKPKNRYANV
PTP-18      MEME---------KEFEQI--DKSGSWAAIYQDIRHEASDFPCRVAKLPKNKNRNRYRDV
PTP-S31-D   MRMRP-ISKKSFLQHVEELCTNNNLKFQEEFSELPKFLQDLSSTDADLPWNRAKNRFPNI
                 *         .    .   .   .    *.  .**. ..

CD45-D1     LPYDYNRVELSEINGDAGSNYINASYIDGFKEPRKYIAAQGPRDETVDDFWRMIWEQKAT
LAR-D1      IAYDHSRVILTSIDGVPGSDYINANYIDGYRKQNAYIATQGPLPETMGDFWRMVWEQRTA
PTP-18      SPFDHSRIKLHQEDN-----DYINASLIKMEEAQRSYILTQGPLPNTCGHFWEMVWEQKSR
PTP-S31-D   KPYNNNRVKLIADASVPGSDYINASYISGYLCPNEFIATQGPLPGTVGDFWRMVWETRAK
             ...  .*. *            .****. *     .* .***   *  ..** *.** ..

CD45-D1     VIVMVTRCEEGNRNKCAEYWPSMEEGTRAFGD--VVVKINQHKRCPDYIIQKLNIVNKKE
LAR-D1      TVVMMTRLEEKSRVKCDQYWPAR--GTETCGL--IQVTLLDTVELATYTVRTFAL-HKSG
PTP-18      GVVMLNRVMEKGSLKCAQYWPQKEEKEMIFEDTNLKLTLISEDIKSYYTVRQLELENLTT
PTP-S31-D   TLVMLTQCFEKGRIRCHQYWPEDNKPVTVFGD--IVITKLMEDVQIDWTIRDLKIERHGD
             .**.. .    *   . *  .***         . .                . . ...

CD45-D1     KATGREVTHIQFTSWPDHGVPEDPHLLLKLRRRVNAFSNFFS--GPIVVHCSAGVGRTGT
LAR-D1      SSEKRELRQFQFMAWPDHGVPEYPTPILAFLRRVKACNPLDA--GPMVVHCSAGVGRTGC
PTP-18      -QETREILHFHYTTWPDFGVPESPASFLNFLFKVRESGSLSPEHGPVVVHCSAGIGRSGT
PTP-S31-D   CMT----VRQCNFTAWPEHGVPENSAPLIHFVKLVRASRAHDT--TPMIVHCSAGVGRTGV
                  . .. .**. ****  . ...   *        *..****.**.*

CD45-D1     YIGIDA----MLEGLEAENKVDVYGYVVKLRRQRCLMVQVEAQYILIHQALVEYNQFGETE
LAR-D1      FIVIDA----MLERMKHEKTVDIYGHVTCMRSQRNYMVQTEDQYVF HEALLEAATCGHTE
PTP-18      FCLADTCLLLMDKRKDPSSVDIKKVLLEMRKFRMGLIQTADQLRFSYLAVIEGAKFIMGD
PTP-S31-D   FIALDH----LTQHINDHDFVDIYGLVAELRSERMCMVQNLAQYIFLHQCILDLLSNKGSN
                       *      **.    .  * *    ..*  *   .     ...   .
```

FIG.7

```
  1  gccttcgtcaactaattctccttaaattttagaacttcatcccaataacttattagaaaaa   60
 61  aaagaaagtagaataggttctatggaattaaaacaagaaaaagaagtcgagtagctataa   120
 21                    N  K  K  K  K  S  S  S  Y  K             40
121  atttgcaacatattcagagaggtgattttaacaaggaattatttgactaaatgtcttta   180
 41   F  A  T  Y  S  E  R                                         60
181  cttaaaagaaaactaaacctaatttatatactttgtgtgaactcccttcttgactt       240
241  tactccgcttgtttagaattcgacagaagcagaaagaaggtggcacatactcctcctcag  300
 81              I  R  Q  K  Q  K  E  G  G  T  Y  S  P  Q       100
301  gatgcagaaattattgacactaaattgaagctggatcagctcatcacagtggcagacctg  360
101   D  A  E  I  I  D  T  K  L  K  L  D  Q  L  I  T  V  A  D  L 120
361  gaactgaaggacgagagattaacgcgatactctcattctttttagacgcaaggagatt    420
121   E  L  K  D  E  R  L  T  R  Y  S  S  F  F  F  R  R  K  E  I 140
421  tttgtcatccagttacttagttatagaaaatccatcaagccaataagcaagaaatcctttc 480
141   F  V  I  Q  L  L  S  Y  R  K  S  I  K  P  I  S  K  K  S  F 160
481  ctgcaacatgttgaagagctttgcacaaacaacctaaagtttcaagaatttcg         540
161   L  Q  H  V  E  E  L  C  T  N  N  N  L  K  F  Q  E  E  F  S 180
541  gaattaccaaaatttcttcaggatctcttcaactgatgctgcttggaataga           600
181   E  L  P  K  F  L  Q  D  L  S  S  T  D  A  D  L  P  W  N  R 200
```

FIG. 9A

```
601  gcaaaaaccgcttcccaaacatataaaccatataataacagagtaaagctgatagct  660
201   A  K  N  R  F  P  N  I  K  P  Y  N  N  N  R  V  K  L  I  A   220

661  gacgctagtgttccaggttccgattatattctggtatattctggttattatgt      720
221   D  A  S  V  P  G  S  D  Y  I  N  A  S  Y  I  S  G  Y  L  C   240

721  ccaaatgaatttattgctactcaaggtccactaccaggaacagttggagattttggaga  780
241   P  N  E  F  I  A  T  Q  G  P  L  P  G  T  V  G  D  F  W  R   260

781  atggtgtgggaaaccagagcaaaaacattagtaatgctaacacagtgttttgaaaagga  840
261   M  V  W  E  T  R  A  K  T  L  V  M  L  T  Q  C  F  E  K  G   280

841  cggatcagatgccatcagtattggccagaggacaacaagccagttactgtctttggagat  900
281   R  I  R  C  H  Q  Y  W  P  E  D  N  K  P  V  T  V  F  G  D   300

901  atagtgattacaaagctaatggaggatgttcaaatagattggactatcaggatctgaaa  960
301   I  V  I  T  K  L  M  E  D  V  Q  I  D  W  T  I  R  D  L  K   320

961  attgaaaggcatgggactgagaacagcgccctctaattcactttgtgaagttggttcgagcaagag  1020
321   I  E  R  H  G  D  C  M  T  V  R  Q  C  N  F  T  A  W  P  E   340

1021 catgggttcctgagaacagcgccctctaattcactttgtgaagttggttcgagcaagc  1080
341   H  G  V  P  E  N  S  A  P  L  I  H  F  V  K  L  V  R  A  S   360

1081 agggcacatgacacaccctatgattgttcactgcagtgctgagttgaagaactgga    1140
361   R  A  H  D  T  T  P  M  I  V  H  C  S  A  G  V  G  R  T  G   380
```

FIG. 9B

```
1141  gttttattgctctggaccatttaacacaacatataaatgaccatgatttgtgatata  1200
 381   V  F  I  A  L  D  H  L  T  Q  H  I  N  D  H  D  F  V  D  I   400

1201  tatggactagtagctgaactgagaagtgaaagaatgtgcatggtgcagaatctggcacag  1260
 401   Y  G  L  V  A  E  L  R  S  E  R  M  C  M  V  Q  N  L  A  Q   420

1261  tatatctttttacaccagtgcattctggatctcttatcaataaggaagtaatcagccc    1320
 421   Y  I  F  L  H  Q  C  I  L  D  L  L  S  N  K  G  S  N  Q  P   440

1321  atctgtttgttaactattcagcacttcagaagatggactctttggacgccatggaaggt  1380
 441   I  C  F  V  N  Y  S  A  L  Q  K  M  D  S  L  D  A  M  E  G   460

1381  gatgttgagcttgaatggaagaaaccactatgtaaatattcagaccaaaggatacaatt  1440
 461   D  V  E  L  E  W  E  E  T  T  M  *                            471

1441  ggaagagattttaaatcccagggggccaaagttaccccctcattcttccgaattgaaatg  1500

1501  tgcaaccttaagaaatatctatgcttctctcactgtgccttttccaaacgattgaacat  1560

1561  tttaagactagttcttgaaatagctaatacagaataattatttgttttgtacagaataa  1620
```

FIG. 9C

```
1621  atattatgcatttaaatgcttaagaaaagacatcccatatgttttgaagtcctccata  1680
1681  tttggaataagccaaatagaaattattattatagcattaatgtttcaatgtttcaatgtgaat  1740
1741  tttccctatgtattggatttaatttgaggacaaagttgtaaatgttgattcagtagtg  1800
1801  ttgttttggcttacagggtattgatgtttctgtgttttcttgtgataatttccaggactgtcataatg  1860
1861  atctgtacttccatgtacaccctgtgttttgaatcctctgttttatgagtgctgagata  1920
1921  tcatctcatgatcccgaacagtgaacagtaccccctgacactgcaggattacttggc  1980
1981  ctttatacaacacagtagctcttcaggacacttaggctattaatttcgattgtgt  2040
2041  cttcagtttgagaaccttaaaagaaattaaaagtgcaattgcacacatgaaattacaga  2100
2101  gtaccattctagcaaacctacatttgtaaacttaaaacacaagttttxcccctgtatt  2160
2161  gtatattcaaatatatagtaaatgtatcagagtatttgccattagatgatcaaccta  2220
2221  atattaacaattctgaagagttcttcagcaaaatgtatcaagagtaataaaacactg  2280
```

FIG. 9D

```
2281  tgcgtgtttcaagcttgtaaaccaatgatctgctgctgtggtgccaacagagacttccaa  2340
2341  atggattatgttaaatggccgtcatttccaaggttgattttgagcagtatactt        2400
2401  ggtggaactgaaaacaagaaattaaccatctatagcaaattcaaggtttctttatagaa   2460
2461  aatctttcagcctccatcttattaaatagtgacaatgtggtaagttttgaattatatgaa 2520
2521  ctcatttgtcatagatttcaattaagagtaataatagtattaattatgctctttctatg  2580
2581  ataagaagtatatcttatgcttatttccgctggaacatatatatatgaaatgctatgg   2640
2641  ccaataaaattgaattttaatgaaaaaaaaaaaaaaaaaaaaaaaaaa              2692
```

FIG. 9E

```
S31-14    ------------------IRQKQKEGGTYSPQDAEIIDTKLKLDQLITVADLELKDERLTR---
S31-2     ------------------IRQKQKEGGTYSPQDAEIIDTKLKLDQLITVADLELKDERLTR---
S31-5     ------------------IRQKQKQGGTYSPQDAEIIDTKLKLDQLITVADLELKDERLTRYSSF
S31-63    KSSSYKFATYSERIRQKQKEGGTYSPQDAEIIDTKLKLDQLITVADLELKDERLTRYSSF
S31-III   EKQ---------VTTIRQKQKEGGTYSPQDAEIIDTKLKLDQLITVADLELKDERLTRYSSF
                            *****.*******************************

S31-14    --------------PISKK
S31-2     ----------LLSYRKSIKPISKK
S31-5     FFRRKEIFVIQLLSYRKSIKPISKK
S31-63    FFRRKEIFVIQLLSYRKSIKPISKK
S31-III   FFRRKEIFVIQLLSYRKSIKPISKK
                       *****

```
  1  ggaagtctgggagccagtaccctgtggatacaaaagttccagtgttcccacaaatattgcttttctgatgttcagtcaactagtgca   90
  1   G  R  S  G  S  Q  Y  P  V  D  T  K  V  P  S  V  P  T  N  I  A  F  S  D  V  Q  S  T  S  A   30

91  acattgacatggataagacctgacactatccttggctactttcaaaattacaaatccactcgtgctcaaaatgcaagaa           180
 31   T  L  T  W  I  R  P  D  T  I  L  G  Y  F  Q  N  Y  K  I  T  T  Q  L  R  A  Q  K  C  K  E   60

181  tgggaatccgaagaatgtgttgaatatcaaaaattcaatacctctatgaagctcacttaactgaagagcagtatatggattaagaa    270
 61   W  E  S  E  E  C  V  E  Y  Q  K  I  Q  Y  L  Y  E  A  H  L  T  E  E  T  V  Y  G  L  K  K   90

271  tttagatggtatagattccaagtggctgccagcaccaatgctgcaatgctctaaactctgcctggc                         360
 91   F  R  W  Y  R  F  Q  V  A  A  S  T  N  A  G  Y  G  N  A  S  N  W  I  S  T  K  T  L  P  G  120

361  cctccagatggtcctcctgaaaatgttcatgtagtagcaacatcacctttagcatcagcataagctggatgaacctgctgtcattact  450
121   P  P  D  G  P  P  E  N  V  H  V  V  A  T  S  P  F  S  I  S  I  S  W  S  E  P  A  V  I  T  150

451  ggaccaacatgttatctgattgatgtcaaatcggtagataatgatgaatttaatatatccttcatcaagtcaaatgaagaaataaacc  540
151   G  P  T  C  Y  L  I  D  V  K  S  V  D  N  D  E  F  N  I  S  F  I  K  S  N  E  E  N  K  T  180

541  atagaaattaaagattttagaatatattcacaaggtatttctgtagtgatcactgcatttactgggacattagtgctgcatatgtgaaggg 630
181   I  E  I  K  D  L  E  I  F  T  R  Y  S  V  V  I  T  A  F  T  G  N  I  S  A  A  Y  V  E  G  210

631  aagtcaagtgctgaatgattgttactttagaatcagccccaaggaccaccaacaacatgacattcagaagatacagatgaa        720
211   K  S  S  A  E  M  I  V  T  T  L  E  S  A  P  K  D  P  P  N  N  M  T  F  Q  K  I  P  D  E  240

721  gttacaaaatttcaattaacgttcctcctcctcaacctaatgaaatatccagtatatcaagctcggttaccgaagagatgat         810
241   V  T  K  F  Q  L  T  F  L  P  P  S  Q  P  N  G  N  I  Q  V  Y  Q  A  L  V  Y  R  E  D  D  270

811  cctactgctgtccagattcacaacctcagtattatacagaaaccaacacattcgtcattgcaatgctagaaggactaaaaggtggacat  900
271   P  T  A  V  Q  I  H  N  L  S  I  I  Q  K  T  N  T  F  V  I  A  M  L  E  G  L  K  G  G  H  300
```

```
901   acatacaatatcagtgtttacgcagtcaatagtgctgtggtgcaggtccaaggttccgatgagaataaccatggatatcaaggctccagca   990
301    T  Y  N  I  S  V  Y  A  V  N  S  A  G  P  K  V  P  M  R  I  T  M  D  I  K  A  P  A      330

991   cgaccaaaaaccaaccaaccctatttatgatgccaggaaaactgcttgtgacttcaacaacaattacaatcagaatgccaatatgt        1080
331    R  P  K  T  K  P  T  P  I  Y  D  A  T  G  K  L  L  V  T  S  T  T  I  T  I  R  M  P  I  C 360

1081  tactacagtgatgatcatggaccaataaaaatgtacaagtgcttgtgacagaacaggagctcagcatgatgaaatgtaacaaagtgg      1170
361    Y  Y  S  D  D  H  G  P  I  K  N  V  Q  V  L  V  T  E  T  G  A  Q  H  D  G  N  V  T  K  W 390

1171  totgtgcatatttttaataagcaaggccatatttacaaatgaaggcttcctaccctccatgtacagaggaaggacaaagtttagt        1260
391    Y  D  A  Y  F  N  K  A  R  P  Y  F  T  N  E  G  F  P  N  P  P  C  T  E  G  K  T  K  F  S 420

1261  ggcaatgaagaaatctacatcataggtgctgataatgcatgtatgattcctggcaatgaagacaaaatttgcaatggaccactgaaacca   1350
421    G  N  E  E  I  Y  I  I  G  A  D  N  A  C  M  I  P  G  N  E  D  K  I  C  N  G  P  L  K  P 450

1351  aaaagcaatactattaaattagagctacaaatattatggacaattactgacttctgattattctgacctgttaagacttttaggg        1440
451    K  K  Q  Y  L  F  K  F  R  A  T  N  I  M  G  Q  F  T  D  S  D  Y  S  D  P  V  K  T  L  G 480

1441  gaaggactttcagaagaaccgtagagattcattcttccgtacttgtgtatccttcaataattctccttgaacagctatttttgca        1530
481    E  G  L  S  E  R  T  V  E  I  I  L  S  V  T  L  C  I  L  S  I  I  L  L  G  T  A  I  F  A 510

1531  tttgcaaggattcgacaggaagcagaagaaggtggcacatactctcctcaggatgcagaatattgacactaaattgaagctggatcag    1620
511    F  A  R  I  R  Q  K  Q  K  E  G  G  T  Y  S  P  Q  D  A  E  I  I  D  T  K  L  K  L  D  Q 540

1621  ctcatcacagtggcagacctgaaactgaaggacgagagattaacgcgatactcttcatttttcttagacgcaaggagattttgtcatc   1710
541    L  I  T  V  A  D  L  E  L  K  D  E  R  L  T  R  Y  S  S  F  F  F  R  R  K  E  I  F  V  I 570

1711  cagttacttagttatagaaaatccatcaagcaatgcaagaaatccttcctgcaacatgttgaagagctttgaagaagaactgtgcaccaaccaccta  1800
571    Q  L  L  S  Y  R  K  S  I  K  P  I  S  K  K  S  F  L  Q  H  V  E  E  L  C  T  N  N  N  L 600
```

FIG.12B

```
1801 aagtttcaagaagaatttcggaattaccaaatttcttcaggatcttttcaactgatgctgatctgccttggaatagagcaaaaac  1890
 601  K  F  Q  E  E  F  S  E  L  P  K  F  L  Q  D  L  S  S  T  D  A  D  L  P  W  N  R  A  K  N    630

1891 cgcttccaaacataaaccatataataacaggagtaaagctgatagctgacgctagtgttccaggttcgattatattaatgccagc  1980
 631  R  F  P  N  I  K  P  Y  N  N  N  R  V  K  L  I  A  D  A  S  V  P  G  S  D  Y  I  N  A  S    660

1981 tatatttctggttattatgtccaaatgaattattgctactccaggtccactaccaggaacagttggagatttggagaatggtgtgg  2070
 661  Y  I  S  G  Y  L  C  P  N  E  F  I  A  T  Q  G  P  L  P  G  T  V  G  D  F  W  R  M  V  W    690

2071 gaaaccaggacaaaacattagtaatgctaacacagtgttgaaaaggacggatcagatgccatcagtattggccagaggacaacag  2160
 691  E  T  R  A  K  T  L  V  M  L  T  Q  C  F  E  K  G  R  I  R  C  H  Q  Y  W  P  E  D  N  K    720

2161 ccagttactgtctttggagatatagtgattacaaagctaatgaggatgttcaaatagattggactatcagggatctgaaaattgaaagg  2260
 721  P  V  T  V  F  G  D  I  V  I  T  K  L  M  E  D  V  Q  I  D  W  T  I  R  D  L  K  I  E  R    750

2251 catggggattgcatgactgttcgacagtgtaacttactgccaggagcatgggtgttcctgagaacagcgccctctaattcacttt  2340
 751  H  G  D  C  M  T  V  R  Q  C  N  F  T  A  W  P  E  H  G  V  P  E  N  S  A  P  L  I  H  F    780

2341 gtgaagttggttcgagcaagcaggcacatgaccacactatgattgttcactgcagtgctggagttgaagaactggagttttatt  2430
 781  V  K  L  V  R  A  S  R  A  H  D  T  T  P  M  I  V  H  C  S  A  G  V  G  R  T  G  V  F  I    810

2431 gctctggacattaacacaacatataatgaccatgattttgatatatgactagtcgaactgagagtgctgaactgagctctggatatgaactgagcttcaattcataaaatgatc  2520
 811  A  L  D  H  L  T  Q  H  I  N  D  H  D  F  V  D  I  Y  G  L  V  A  E  L  R  S  E  R  M  C    840

2521 atggtgcagaatctggcacagtatatcttttacaccgtgcattctggatctcttatcaataaggaagtaatcagccatctgtttt  2610
 841  M  V  Q  N  L  A  Q  Y  I  F  L  H  Q  C  I  L  D  L  L  S  N  K  G  S  N  Q  P  I  C  F    870

2611 gttaactattcagcacttcagaagatggactctttggacgccatgaaggtgatgttggcttgaatgggaagaaccactatgtaaata  2700
 871  V  N  Y  S  A  L  Q  K  M  D  S  L  D  A  M  E  G  D  V  E  L  E  W  E  E  T  T  M  *      900
```

FIG.12C

```
2701  ttcagaccaaggatacaattggaagagattttaaatcccagggccaagttaccccctcattcttccgaattgaaatgtgcaacctt  2790
2791  aagaaatatctatgcttctctcactgtgccttccaaacggattgaacatttaagactagttcttgaaaatagctaatacagaataat  2790
2881  tatttgtttgtacagaataaatattatgcatttaaatgcttaagaaaagacatcccatatgtttttgagtcctccatattttggaat  2970
2971  aagccaaatagaaaattattattatattagcattaatgtttccatgtgaatttttccctatgtattggatttaatttgaggacaaagtt  3060
3061  gtaaatgttgattcagtagtgttgtttttggcttacagggtattgatgtttcttgtggataattccaggactgtcataatgatctgtact  3150
3151  tccatgtacaccctgtgtttgaatcctctgtttatgagtgctgagatatcatctcatgatcccgaacagctgaacagtaacccctg  3240
3241  acactgcaggattacttggcctttatacaacacacagtagctcttcagggacactaggctattaatttcgattgtgtcttcagttt  3330
3331  gagaaccttaaaagaaaattaaaagtgcaattgtatgttcaaatatatcagaggtaccattctagcaaacctacattgtaaactttaaac  3420
3421  acaagtttxccccctgtattgtatattcagcaaaatgtatcagaatggattatgttaaatggccgtcattcattcccaggttgatttt  3510
3511  atctgaagggtttcttcagcaaatgtatcagaatggattatgttaaatggccttgtaaccatgatctgctgtgt  3600
3601  ggtgccaacagagacttccaaatggattatgttaaatggccgtcattcattcccaggtgatttggcagtatactggtggaact  3690
3691  gaaaacaagaaattaaccatctatagcaaattcaaggttctcttatagaaaatcttcagcctccatcttattaatagtgacaatgtg  3780
3781  gtaagttttgaattatatgaactcatttgtcatagatttcaattaagatgtaataatagtattaattatgctcttctatgataagagt  3870
3871  atatcttatgcttatttccgctggaacatatatatatgaaatgctatggccaataaaattgaatttaatgaaaaaaaaaaaaaa  3960
3961  aaaaaaaaaaa  3973
```

FIG.12D

```
PTP-S31         GNEDKICNGPLKPKKQYLFKFRATNIMGQFTD.SDYSDPVK
                ::| ||.:|.|:||.|.:|: |||.|.::|:|:
IL2R-beta  188 .QKQEWICLCLETLTPDTQYEFQVRVKPLQGEFTTWSPWSQPLA  228
```

FIG. 13

```
            PSV   PT N IA F SD V QST       SA TLT W IRPDTILGYFQN Y KITTQ LRAQKCKEWESEECVEYQKIQYLYEAHLTEETVYG
GPPDG P PE N VH V VA T SPF               SI SIS W SEPAVITGPTC Y LIDVK SVDNDEFNISFIKSNEENKTIEIKD
APKD P PN N MT F QK I PDEVT              KF QLT F LPPSQPNGNIQV Y QALVY REDDPTAVQIHNLSIIQKTNTFVIAMLEG
       P IK N VQ V LV T ETGAQHD GN VTK W YDAYFNKARP   Y FTNEG FPNPPCTEGKTKFSGNEEIYIIGADNACMIPGNEDKICNGP
       LS P PT N LH L EA N PDTG          VL TVS W ERSTTPDITG   Y RITT PTMGQQGNSLEEVHADQSSCTPDN

S31-FN-4   L K KF RW Y RFQ V AA S T    N AGYGNASNWISTKTLP
S31-FN-3   L E IF TR Y SW I IT A F    TG N ISAAYVEGKSSAEMIVTTLES
S31-FN-2   L K GG HT Y NIS V Y A V     N SAGAGPKVPMRITMDIKAPARPKTKPTP
S31-FN-1   L K PK KQ Y LFK F R A T     N IMGQFTDSDYSDPVKTLGEGLSERTVE
FN-III     L S PG LE Y NVS V Y T V KD D KESVPISDTIIP
```

FIG. 14

```
IGF1R    LHGLKPWTQYAVYVKAVTLTMVENDHIRGAKSEILYIRTNASVPSIPLDVLS
IR       MRGLKPWTQYAIFVKTL-VTFSDERRTYGAKSDIIYVQTDATNPSVPLDPIS
IRR      LASLKPWTQYAVFVRAITLTTEEDSPHQGAQSPIVYLRTLPAAPTVPQDVIS
PTPS31   IKDLEIFTRYSVVITAFT-GNISAAYVEGKSSAEMIVTTLESAPKGPPNNMT
              *  *.*. :    *       .         *        .  :

IGF1R    ---ASNSSSQLIVKWNPPSLPNGNLSYY---IVRWQRQPQDGYLYRHNYCSKD
IR       ---VSNSSSQIILKWKPPSDPNGNITHY---LVFWERQAEDSELFELDYCLKG
IRR      ---TSNSSSHLLVRWKPPTQRNGNLTYY---LVLWQRLAEDGDLYLNDYCHRG
PTPS31   FQKIPDEVTKFQLTFLPPSQPNGNIQVYQALVYREDDPTAVQIHNLSIIQKT
            *: *** . :.*   :      .   :  *:    :

FIG.15
```

PTP-S31: A NOVEL PROTEIN TYROSINE PHOSPHATASE

This is a divisional of application Ser. No. 08/449,609, filed May 24, 1995, now issued as U.S. Pat. No. 5,952,212 which is a divisional of application Ser. No. 08/036,210, filed Mar. 23, 1993, now U.S. Pat. No. 5,585,233, each of which is incorporated herein by reference in its entirety.

1. INTRODUCTION

The invention, in the fields of biochemistry and cell and molecular biology, relates to a novel protein tyrosine phosphatase (PTPase or PTP) protein or glycoprotein, termed PTP-S31, the use of such molecule in pharmaceutical preparations, and pharmaceutical compositions comprising PTP-S31 or functional derivatives thereof. This invention is also directed to nucleic acid molecules encoding the PTP-S31 protein or functional derivative, recombinant expression vectors carrying the nucleic acid molecules, cells containing the recombinant expression vectors, methods for production and identification of PTP-S31 or the DNA coding therefor, antibodies specific for PTP-S31, and methods for screening compounds capable of binding to and inhibiting or stimulating protein tyrosine phosphatase enzymatic activity of PTP-S31.

2. BACKGROUND OF THE INVENTION

Phosphorylation of proteins is a fundamental mechanism for regulating diverse cellular processes. While the majority of protein phosphorylation occurs at serine and threonine residues, phosphorylation at tyrosine residues is attracting a great deal of interest since the discovery that many oncogene products and growth factor receptors possess intrinsic protein tyrosine kinase activity. The importance of protein tyrosine phosphorylation in growth factor signal transduction, cell cycle progression and neoplastic transformation is now well established (Hunter et al., *Ann. Rev. Biochem.* 54:987–930 (1985), Ullrich et al., *Cell* 61: 203–212 (1990), Nurse, *Nature* 344:503–508 (1990), Cantley et al., *Cell* 64:281–302 (1991)).

Biochemical studies have shown that phosphorylation on tyrosine residues of a variety of cellular proteins is a dynamic process involving competing phosphorylation and dephosphorylation reactions. The regulation of protein tyrosine phosphorylation is mediated by the reciprocal actions of protein tyrosine kinases (PTKases or PTKS) and protein tyrosine phosphatases (PTPs). The tyrosine phosphorylation reactions are catalyzed by PTKs. Tyrosine phosphorylated proteins can be specifically is dephosphorylated through the action of PTPS. The level of protein tyrosine phosphorylation of intracellular substances is determined by the balance of PTK and PTP activities. (Hunter, T., *Cell* 58:1013–1016 (1989)).

2.1. PTKs

The protein tyrosine kinases (PTKs; ATP:protein-tyrosine O-phosphotransferase, EC 2.7.1.112) are a large family of proteins that includes many growth factor receptors and potential oncogenes. (Hanks et al., *Science* 241:42–52 (1988)). Many PTKs have been linked to initial signals required for induction or the cell cycle (Weaver et al., *Mol. and Cell. Biol.* 11(9):4415–4422 (1991)). PTKs comprise a discrete family of enzymes having common ancestry with, but major differences from, serine/threonine-specific protein kinases (Hanks et al., supra). The mechanisms leading to changes in activity of PTKs are best understood in the case of receptor-type PTKs having a transmembrane topology (Ullrich et al. (1990) supra). The binding of specific ligands to the extracellular domain of members of receptor-type PTKs is thought to induce their oligomerization leading to an increase in tyrosine kinase activity and activation of the signal transduction pathways (Ullrich et al., (1990) supra). Deregulation of kinase activity through mutation or overexpression is a well-established mechanism for cell transformation (Hunter et al., (1985) supra; Ullrich et al., (1990) supra).

2.2. PTPS

The protein phosphatases are composed of at least two separate and distinct families (Hunter, T.(1989) supra) the protein serine/threonine phosphatases and the protein tyrosine phosphatases (PTPs; protein-tyrosine-phosphate phosphohydrolase, EC 3.13.48)). The PTPs are a family of proteins that have been classified into two subgroups. The first subgroup is made up of the low molecular weight, intracellular enzymes that contain a single conserved catalytic phosphatase domain. All known intracellular type PTPS contain a single conserved catalytic phosphatase domain.; Examples of the first group of PTPs include (1) placental PTP 1B (Charbonneau et al., *Proc. Natl. Acad. Sci. USA* 86:5252–5256 (1989); Chernoff et al., *Proc. Natl. Acad. Sci. USA* 87:2735–2789 (1990)), (2) T-cell PTP (Cool et al. *Proc. Natl. Acad. Sci. USA* 86:5257–5261 (1989)), (3) rat brain PTP (Guan et al., *Proc. Natl. Acad. Sci. USA* 87:1501–1502 (1990)), (4) neuronal phosphatase (STEP) (Lombroso et al., *Proc. Natl. Acad. Sci. USA* 88:7242–7246 (1991)), and (5) cytoplasmic phosphatases that contain a region of homology to cytoskeletal proteins (Guet al., *Proc. Natl. Acad. Sci. USA* 88:5867–57871 (1991); Yang et al., *Proc. Natl. Acad. Sci. USA* 88:5949–5953 (1991)).

The second subgroup is made up of the high molecular weight, receptor-linked PTPs, termed RPTPs. RPTPs consist of (a) an intracellular catalytic region, (b) a single transmembrane segment, and (c) a putative ligand-binding extracellular domain. The structures and sizes of the putative ligand-binding extracellular "reqeptor" domains of RPTPs are quite divergent. In contrast, the intracellular catalytic regions of RPTPs are highly homologous. All RPTPs have two tandemly duplicated catalytic phosphatase homology domains, with the prominent exception of an RPTP termed HPTPβ, which has only one catalytic phosphatase domain. (Tsai et al., *J. Biol. Chem.* 266:10534–10543 (1991)).

One example of RPTPs is a family of proteins termed leukocyte common antigens (LCA) (Ralph, S. J., *EMBO J.* 6:1251–1257 (1987)) which are high molecular weight glycoproteins expressed on the surface of all leukocytes and their hemopoietic progenitors (Thomas, *Ann. Rev. Immunol.* 7:339–369 (1989)). A remarkable degree of similarity exists in the sequences of LCA from several species (Charbonneau et al., *Proc. Natl. Acad. Sci. USA* 85:7182–7186 (1988)). LCA has been referred to in the literature by different names, including T200 (Trowbridge et al., *Eur. J. Immunol.* 6:557–562 (1962)), B220 for the B lymphocyte form (Coffman et al., *Nature* 289:681–683 (1981)), the mouse allotypic marker Ly-5 (Komuro et al., *Immunogenetics* 1:452–456 (1975)), and more recently CD45 (Cobbold et al., *Leucocyte Typing III,* A. J. McMichael et al., eds., pp. 788–803 (1987)).

CD45 appears to play a critical role in T cell activation (reviewed in Weiss A., *Ann. Rev. Genet.* 25:487–510 (1991)). For example, T-cell clones that were chemically mutagenized and selected for their failure to express CD45 had impaired responses to T-cell receptor stimuli (Weaver et al., supra). These T-cell clones were functionally defective in their responses to signals transmitted through the T cell antigen receptor, including cytolysis of appropriate targets, proliferation, and lymphokine production (Weaver et al., supra). Other studies indicate that the PTP activity of CD45 plays a role in the activation of pp $56^{1ck}$, a lymphocyte-specific PTK (Mustelin et al., *Proc. Natl. Acad. Sci. USA* 86:6302–6306 (1989); ostergaard et al., *Proc. Natl. Acad. Sci. USA* 86:8959–8963 (1989)). These authors hypothesized that the phosphatase activity of CD45 activates $pp56^{kk}$ by dephosphorylation of a C-terminal tyrosine residue, which may, in turn, be related to T-cell activation.

Another other example of an RPTP is the leukocyte common antigen related molecule (LAR), initially identified as a homologue of LCA (Streuli et al., *J. Exp. Med.* 168:1523–1530 (1988)). Although the intracellular catalytic region of the LAR molecule contains two catalytic phosphatase homology domains (domain I and domain II), mutational analyses suggested that only domain I had catalytic phosphatase activity, whereas domain II was enzymatically inactive (Streuli et al., *EMBO J.* 9(8):2399–2407 (1990)). Chemically induced LAR mutants having tyrosine at amino acid position 1379 changed to a phenylalanine were temperature-sensitive (Tsai et al., *J. Biol. Chem.* 266(16): 10534–10543 (1991)).

A recently cloned mouse RPTP, designated mRPTPµ, was found to have an extracellular domain that shared some structural motifs with LAR. (Gebbink, M. F. B. G. et al., *FEBS Lett.* 290:123–130 (1991). These authors also cloned a human homologue of RPTPµ and localized the gene on human chromosome 18.

Two Drosophila PTPs, termed DLAR and DPTP, have been predicted based on the sequences of cDNA clones (Streuli et al., *Proc. Natl. Acad. Sci. USA* 86:8698–8702 (1989)). cDNAs coding for another Drosophila RPTP, termed DPTP 99A, have been cloned and characterized (Hariharan et al., *Proc. Natl. Acad. Sci. USA* 88:11266–11270 (1991)).

Other examples of RPTPs include RPTP-α, β, γ, and ζ (Krueger et al., *EMBO J.* 9:3241–3252 (1990), Sap et al. *Proc. Natl. Acad. Sci. USA* 67;;6112–6116 (1990), Kaplan et al., *Proc. Natl. Acad. Sci. USA* 87:7000–7004 (1990), Jirik et al., *FEBS Lett.* 273:239–242 (1990), Mathews et al., *Proc. Natl. Acad. sci. USA* 87:4444–4448 (1990), Ohagi et al., *Nucl. Acids Res.* 18:7159 (1990)). Schlessinger, PCT Publication WO 92/01050 (Jan. 23, 1992) disclosed human RPTP-α, β and γ, and described the nature of the structural homologies among the conserved domains of these three RPTPs and other members of this protein family. The murine RPTP-α has 794 amino acids, whereas the human RPTP-α has 802 amino acids. RPTP-α has an intracellular domain homologous to the catalytic domains of other tyrosine phosphatases. The 142 amino acid extracellular domain (including signal peptide of RPTP-α) has a high serine and threonine content (32%) and 8 potential N-glycosylation sites. cDNA clones have been produced that code for the RPTP-α, and RPTP-α has been expressed from eukaryotic hosts. Northern analysis was used to identify the natural expression of RPTP-α in various cells and tissues. A polyclonal antibody to RPTP-α, produced by immunization with a synthetic peptide of RPTP-α, identifies a 130 kDa protein in cells transfected with a cDNA clone encoding a portion of RPTP-α.

Another RPTP, HePTP (Jirik et al., *FASEB J.* 4:82082 (1990) Abstract 2253) was discovered by screening a cDNA library derived from a hepatoblastoma cell line, HepG2, with a probe encoding the two PTP domains of LCA. The HePTP gene appeared to be expressed in a variety of human and murine cell lines and tissues.

Since the initial purification, sequencing, and cloning of a PTP, additional potential PTPs have been identified at a rapid pace. The number of different PTPs that have been identified is increasing steadily, leading to speculations that this family may be as large as the PTK family (Hunter (1989) supra).

Conserved amino acid sequences designated "consensus sequences" have been identified in the catalytic domains of known PTPS (Krueger et al., *EMBO J.* 9:3241–3252 (1990) and Yi et al., *Mol. Cell. Biol.* 12:836–846 (1992), which are incorporated herein by reference). Yi et al. aligned the catalytic phosphatase domain sequences of the following PTPs: LCA, PTP1B, TCPTP, LAR, DLAR, and HPTPα, HPTPβ, and HPTPγ. This alignment includes the following "consensus sequences" (Yi et al., supra, FIG. 2(A)):

1. K C X X Y W P [SEQ ID NO:1]
2. H<u>C</u>S X G X G <u>R</u>X G [SEQ ID NO:2]

Krueger et al., aligned the catalytic phosphatase domain sequences of PTP1B, TCPTP, LAR, LCA, HPTPα, β, 8, ε and ζ, and DLAR and DPTP. This alignment includes the following "consensus sequences: (Krueger et al., supra, FIG. 7):

1. K C X X Y W P [SEQ ID NO:1]
2. H<u>C</u>S X G X G <u>R</u>X G [SEQ ID NO:2]

It is becoming clear that dephosphorylation of tyrosine residues can by itself function as an important regulatory mechanism. Dephosphorylation of a C-terminal tyrosine residue has been shown to activate tyrosine kinase activity in the src family of tyrosine kinases (Hunter, *T. Cell* 49:1–4 (1987)). Tyrosine dephosphorylation has been suggested to be an obligatory step in the mitotic activation of the maturation-promoting factor (MPF) kinase (Morla et al., *Cell* 58:193–203 (1989)). These observations point out the need in the art for understanding the mechanisms that regulate tyrosine phosphatase activity.

It is clear that further analysis of structure-function relationships among PTPs are needed to gain important understanding of the mechanisms of signal transduction, cell cycle progression and cell growth, and neoplastic transformation. Such understanding will also provide useful agents for regulating these processes and for treating diseases associated with their dysregulation.

3. SUMMARY OF THE INVENTION

The inventors describe herein the identification of a novel PTP, termed PTP S31. This novel PTP differs significantly in structure from previously reported PTPs. Further, several variants of this PTP have been identified. The present invention thus provides a PTP-S31 protein or glycoprotein which is a PTP or contains structural features known to be found in PTPs, as well as variants thereof.

When a PTP-S31 protein or glycoprotein of the present invention is one which occurs in nature, it is substantially free of other proteins or glycoproteins with which it is natively associated. A substantially pure PTP-S31 protein or glycoprotein of the invention may be produced by biochemical purification, by chemical means or by recombinant means in a prokaryotic or eukaryotic host, and is provided substantially free of other proteins with which it is natively associated. The PTP-S31 may have modified amino acids.

The invention is further directed to:

(1) a fragment of a PTP-S31 protein or glycoprotein;
(2) a PTP-S31 protein or glycoprotein having additional amino acids;
(3) a PTP-S31 protein or glycoprotein having substituted amino acids; and (4) a PTP-S31 protein or glycoprotein having any combination of deleted, additional, or substituted amino acids.

In all cases the modified PTP-S31 protein or glycoprotein, or fragment thereof, possesses the desired biological activity.

The invention is further directed to a nucleic acid molecule comprising a nucleotide sequence encoding a PTP-S31 protein according to the invention. The nucleic acid molecule may be cDNA, genomic DNA or RNA. The invention is further directed to a nucleic acid construct in the form of an expression vehicle. Also provided are prokaryotic and eukaryotic host cells containing the expression vehicle.

Also included in the present invention is a process for preparing a PTP-S31 protein or glycoprotein of this invention, comprising:

(a) culturing a host capable of expressing a PTP-S31 protein or glycoprotein under culturing conditions, (b) expressing the PTP-S31 protein or glycoprotein; and (c) recovering the PTP-S31 protein or glycoprotein from the culture.

The invention is also directed to a polyclonal, monoclonal or chimeric antibody specific for a PTP-S31 protein or glycoprotein or for an epitope of a PTP-S31 protein or glycoprotein.

The invention is further directed to a method for detecting the presence, or measuring the quantity, of a PTP-S31 protein or glycoprotein in a sample, preferably a cell or a biological sample from a subject, comprising:

(a) contacting the sample, such as a preparation of cells or an extract thereof, with an antibody specific for an epitope of a PTP-S31 protein or glycoprotein; and (b) detecting the binding of the antibody to sample material, or measuring the quantity of antibody bound, thereby detecting the presence or measuring the quantity of the PTP-S31 protein or glycoprotein.

The invention is also directed to a method for detecting the presence of a nucleic acid encoding a normal or mutant PTP-S31 protein or glycoprotein in a sample, preferably a cell or biological sample of a subject, comprising:

(a) contacting the sample, such as a cell or an extract thereof, with an oligonucleotide probe encoding at least a portion of a normal or mutant PTP-S31 protein or glycoprotein under hybridizing conditions; and (b) measuring the hybridization of the probe to nucleic acid of the cell, thereby detecting the presence of the nucleic acid. The nucleic acid of the sample can be selectively amplified, for example, by using the polymerase chain reaction, prior to assay.

The present invention is also directed to a method for identifying or isolating in a sample, preferably a chemical or biological sample, a compound capable of binding to a PTP-S31 protein or glycoprotein, the method comprising:

(a) attaching a PTP-S31 protein or glycoprotein or the compound-binding portion thereof to a solid phase matrix or carrier;

(b) contacting the sample with the PTP-S31 bound to the solid phase matrix, allowing any compound to bind to said PTP-S31, and washing away any unbound material;

(c) detecting the presence of the compound bound to the solid phase.

For purposes of isolation, the bound compound is subjected to the additional step of (d) eluting the bound compound, thereby isolating the compound.

The invention includes a method for identifying an agent molecule capable of stimulating or inhibiting the enzymatic activity of PTP-S31, comprising:

(a) contacting the agent with a PTP-S31 protein or glycoprotein, or a fragment thereof, which PTP-S31 may be in pure form, in a membrane preparation, or in a whole live or fixed cell;

(b) incubating the mixture of step (a) for a sufficient interval;

(c) measuring the enzymatic activity of the PTP-S31;

(d) comparing the enzymatic activity to that of the PTP-S31 protein or glycoprotein incubated without the agent, thereby determining whether the agent stimulates or inhibits the enzymatic activity.

In addition, the present invention provides methods for identifying agonists or antagonists of PTP-S31 action based on the ability of such agents to modulate interactions between (a) PTP-S31 and its target molecules or (b) PTP-S31 and molecules which regulate its enzymatic activity. Compounds identified by such methods may be useful to treat ,diseases associated with PTP-S31 dysfunction or with disordered signal transduction.

4. DESCRIPTION OF THE FIGURES

FIG. 1 presents the partial cDNA sequence [SEQ ID NO:3] and the deduced amino acid sequence (SEQ ID NO:4) of PTP-S31, which is a PCR fragment.

FIG. 2 shows a comparison of the deduced amino acid sequences of the PTP-S31 PCR fragment [SEQ ID NO:4] shown in FIG. 1 with the amino acid sequence of PTP 1B [SEQ ID NO:5] (Chernoff et al., supra). The GAP alignment method is used (Needleman et al., *J. Mol. Biol.* 48: 443–453 (1970)).

FIGS. 3A–3D present the cDNA sequence [SEQ ID NO:6] and the deduced amino acid sequence [SEQ ID NO:7] of PTP-S31C, a cDNA clone (1.20.4) obtained from an RD cell cDNA library (#1). This partial cDNA sequence includes the cDNA sequence of the PCR fragment shown in FIG. 1.

FIGS. 4A–4B show a comparison of the deduced amino acid sequence of the PTP-S31C cDNA clone shown in FIGS. 3A–3D with the amino acid sequence of PTP 1B. The GAP alignment method is used (Needleman et al., supra).

FIGS. 5A–5B present the cDNA sequence [SEQ ID NO:8] and the deduced amino acid sequence [SEQ ID NO:9] of a PCR fragment obtained with oligonucleotides nos. 223 and 224.

FIGS. 6A–6D show the combined cDNA sequence [SEQ ID NO: 10] and the deduced amino acid sequence [SEQ ID NO:11] of PTP-S31D. This cDNA sequence includes the cDNA sequence of the PCR fragment shown in FIGS. 5A–5B.

FIG. 7 shows a comparison of the amino acid sequence of PTP-S31D (SEQ ID NO:47) and the sequences of PTP 1B (SEQ ID NO:5), the first PTP domain of CD45 [SEQ ID NO:12] (Ralph et al. *EMBO J.* 6: 1251–1257 (1987)) and LAR [SEQ ID NO:13] (Streuli et al *J. Exp. Med.* 168: 1523–1530 (1988)), respectively. The CLUSTAL program is used (Higgins, C. et al., *Multiple Sequence Alignment; CABIOS* (1991).

FIG. 8 shows the results of a PTP enzymatic assay using p-nitrophenyl phosphate (pNP-P) as a substrate. The activity of the glutathione-S-transferase(GST)/PTP-S31D fusion protein is compared with that of the GST/PTP-S31C fusion protein and glutathione-S-transferase (negative control).

FIGS. 9A–9E show the cDNA sequence [SEQ ID NO:14] and the deduced amino acid sequence [SEQ ID NO:15] of the longest PTP-S31D cDNA clone (S31D-63) isolated from a cDNA library (#2) made from human skeletal muscle mRNA. The 5' end of this clone differs from that of the PTP-S31C clone isolated from an RD cDNA library (FIGS. 3A–3D). An arrow indicates the position where this clone differs from PTP-S31C.

FIG. 10 presents a schematic overview of the different types of PTP-S31 clones identified in human skeletal muscle cDNA libraries #2 and #3. Only the 5' ends which differ from the PTP-S31C cDNA clone (FIGS. 3A–3D) are depicted.

FIG. 11 shows the deduced amino acid sequences of PTP-S31 variants found in human skeletal muscle, including S31-14 [SEQ ID NO:16], S31-2 [SEQ ID NO:17], S31-5 [SEQ ID NO:18], S31-63 (SEQ ID NO:19) and S31-III [SEQ ID NO:20].

FIGS. 12A–12D show a partial cDNA sequence [SEQ ID NO:21] and the predicted amino acid sequence [SEQ ID NO:22] of a cDNA clone, PTPS31-RD#2, isolated from an RD λ ZAP II cDNA library (library #14). The putative transmembrane region is underlined.

FIG. 13 shows an alignment of a portion of the amino acid sequences of PTPS31-RD#2 (SEQ ID NO:48) and the interleukin 2 receptor β chain (SEQ ID NO:23). Only the parts of the extracellular domains adjacent to the transmembrane regions are shown.

Figure 8:
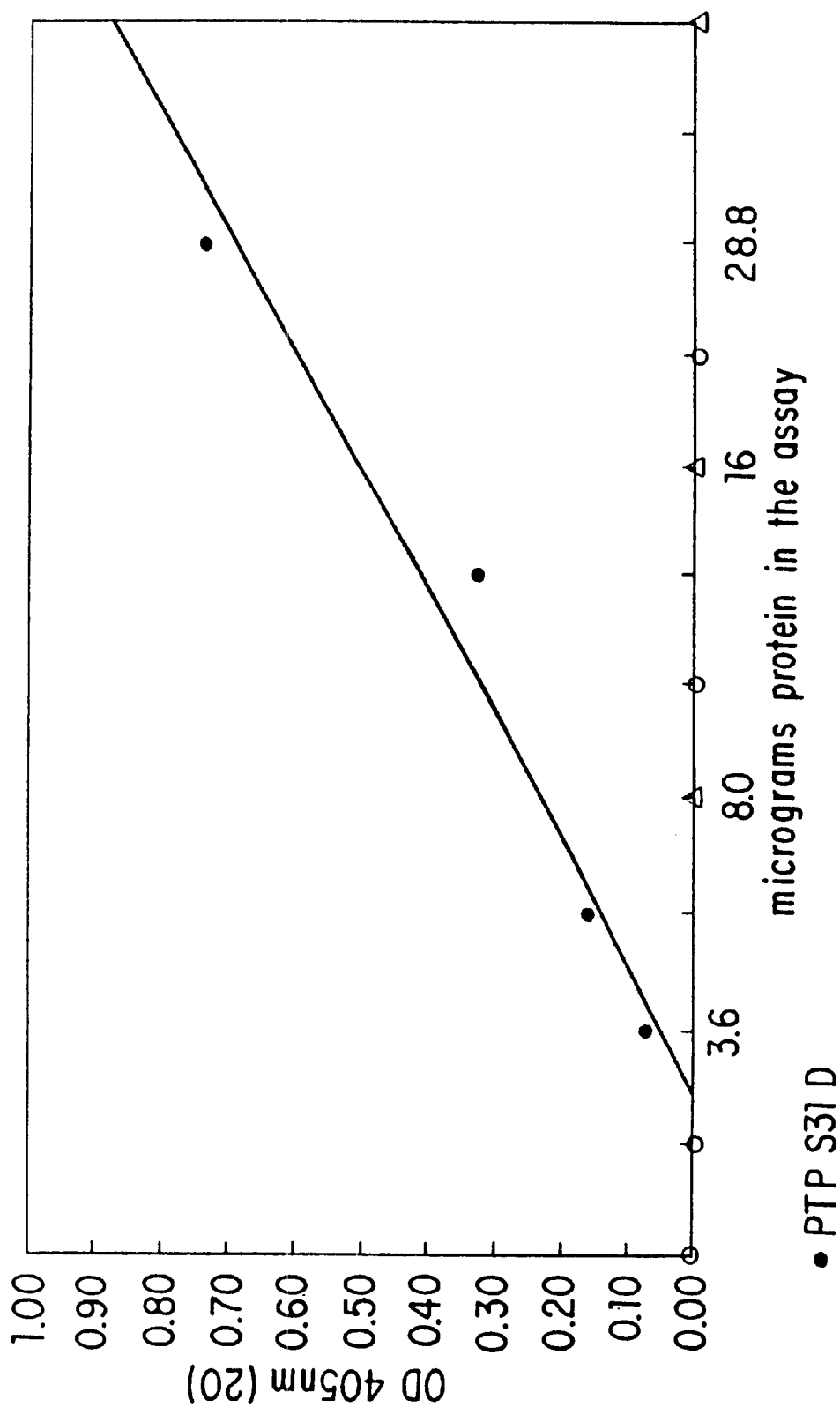

FIG. 14 shows fibronectin type III-like domains of the extracellular regions of PTP-S31. The most C-terminal domain is denoted S31-FN-1 and the most N-terminal domain is S31-FN-4. The FN-like domains are aligned to a type III domain (labeled FN-III) (SEQ ID NO:24) of human fibronectin (Kornblihtt et al., *EMBO J.* 4:1755–1759 (1985)).

FIG. 15 shows an alignment of the amino acid sequence of part of the extacellular region of PTPS31-RD#2 (SEQ ID NO:49–52 respectively, in order of appearance) (designated PTPS31 in the Figure) (SEQ ID NO:53) with the human insulin receptor (IR) (SEQ ID NO:25), the human insulin-like growth factor 1 receptor (IGF1R) (SEQ ID NO:26) and the human insulin-related receptor (IRR) (SEQ ID NO:27).

5. DETAILED DESCRIPTION OF THE INVENTION

Through the use of recombinant DNA methods, the present inventors have identified a novel mammalian protein tyrosine phosphatases (PTP; EC 3.1.3.48), termed PTP-S31, of human origin, and several derivatives thereof. The present inventors have produced cDNA clones coding for the novel protein, and expressed the protein in *E. coli* and in eukaryotic 293 cells.1 Northern analysis has been used to identify the natural expression of the protein in various cells and tissues. They have further produced a polyclonal antibody to the protein by immunization with a recombinant fusion protein including the PTP-S31 variant, PTP-S31D.

5.1. Identification of Agents which Modulate PTP Activity

The PTP-S31 protein or glycoprotein, or derivatives thereof having enzymatic activity, can be used for testing of compounds capable of enhancing or inhibitiing the phosphatase activity. The ability of a compound under testing to modify phosphatase activity can be tested in an in vitro system wherein the test compound is added to a purified PTP-S31 protein or glycoprotein or enzymatically active derivatives thereof, and the effects on enzyme activity measured using standard enzymological procedures well known to those of skill in the art.

Alternatively, the action of a compound on PTP activity can be measured in a whole cell preparation using live or fixed cells, or a fraction derived from live or fixed cells. This method is useful for screening compounds acting on the protein, in particular, on the enzymatic portion of the protein. A test compound is incubated with cells, or with a preparation derived therefrom, which express high amounts of the PTP of this invention, such as transfected COS or NIH-3T3 cells. The amount of cellular phosphotyrosine is measured, using methods well-known in the art (Honegger et al., *Cell* 51:199–209 (1987); Margolis et al., *Cell* 51:1101–1107 (1989)). The results are compared to results obtained in the absence of the test compound, or in the absence or presence of a known activator of PTP. In such studies, the action of the test compound in the presence of an activator tyrosine kinase can also be measured.

A compound which stimulates PTP activity will result in a net decrease in the amount of phosphotyrosine, whereas a compound which inhibits PTP activity will result in a net increase in the amount of phosphotyrosine.

5.2. Treatment of Diseases Associated with PTP Function or Dysfunction

The invention also relates to the use of such identified antagonists or agonists in pharmaceutical compositions intended for treatment of diseases or conditions associated with abnormal expression of a PTP-S31 protein or glycoprotein. Alternatively, the pharmaceutical compositions may be used to treat a disease or condition associated with normal PTP-S31 but one or more deficiencies downstream in the signal transduction pathway or even a condition without any down stream deficiencies. The composition may typically be in a form for systemic or topical injection or infusion and may, as such, be formulated with a suitable carrier for injection or infusion.

The present invention also relates to a method for preventing or treating diseases or conditions involving the activation of PTP-S31, the method comprising administering, to a patient in need thereof, an effective dosage of a PTP-S31 protein or glycoprotein of the invention or an antibody of the invention or a molecule that stimulates or inhibits enzymatic activity of an PTP protein of the invention.

In the case of growth factor receptors which are tyrosine kinases, such as the receptors for epidermal growth (EGF) and for platelet-derived growth factor (PDGF), tyrosine phosphorylation is linked to cell growth and to oncogenic transformation. Activation of a PTP, leading to dephosphorylation would serve as a counterregulatory mechanism to prevent or inhibit growth, and might serve as an endogenous regulatory mechanism against cancer. Thus, mutation or regulation of this receptor/enzyme system may promote susceptibility to cancer.

The insulin receptor is also a tyrosine kinase, and phosphorylation of tyrosine in cells bearing insulin receptors would be associated with normal physiological function associated with insulin. Three specific tyrosine residues in the intracellular portion of the insulin receptor are phosphorylated when insulin binds to the extracellular domain. At the same time, the insulin receptor becomes an active enzyme which can phosphorylate itself or other proteins at tyrosine residues. Phosphorylation of all three specific intracellular tyrosines of the insulin receptor appears to be required for full tyrosine kinase activity. The fully active insulin receptor transmits the signal into the cell (such as skeletal muscle, liver, etc.) by phosphorylating intracellular proteins, which are thereby activated and convey the messages further downstream via the insulin signal transduction pathway. Thus, the well-known physiologic effects of insulin result from a cascade of phosphorylation events.

Insulin signal transduction is controlled tightly by enzymes of the PTP class, which can dephosphorylate, and in the case of the insulin receptor, deactivate, tyrosine kinases. The existence of PTPs with activity towards the insulin receptor can easily be demonstrated. In this setting, then, activation of a PTP would counteract insulin effects, whereas inhibition of the PTP should mimic insulin effects. In fact, treatment of whole cells such as skeletal muscle or adipocytes with pervanadate, which inhibits PTPs, induces an almost full insulin response (Fantus, I. G. et al., *Biochemistry* 28:8864–8871 (1989); Leighton, B. et al., *Biochem. J.* 276:289–292 (1989)). Once the PTP which specifically acts on the insulin receptor is identified, it can be employed in a high throughput screening system and for rational drug design, to identify compounds which, like pervanadate, inhibit the phosphatase and mimic the action of insulin.

Over-activity, or inappropriate activation, of a PTP would be expected to inhibit or totally prevent the action of insulin on cells, leading to diabetes (of an insulin-resistant variety). Thus, susceptibility to diabetes may be associated with PTP dysregulation, and may be diagnosed by measurement of PTP activity, including PTP-S31.

Therefore, the methods of the present invention for identifying normal or mutant PTP-S31 genes, or for measuring the amount or activity of PTP-S31 associated with a cell or tissue, can serve as methods for identifying susceptibility to cancer, diabetes, or other diseases associated with alterations in cellular phosphotyrosine metabolism. In addition, the PTP-S31 protein, functional derivatives thereof, and agents which modulate (activate or inhibit) PTP-S31 enzymatic activity may be used to treat or prevent the development of diseases such as cancer and diabetes.

5.3. Detection and Measurement of PTP-S31 Protein or Nucleic Acid

The present invention provides methods for evaluating the presence and the level of normal or mutant PTP-S31 in a subject. Absence, or more typically, low expression of the PTP-S31, or presence of a mutant PTP-S31, in an individual may serve as an important predictor of susceptibility to oncogenic transformation and the development of cancer. Alternatively, over-expression of PTP-S31 possibly due to a mutant receptor/enzyme system insensitive to negative regulation, or due to overabundance of a stimulatory factor present in the body, may serve as an important predictor of susceptibility to diabetes.

Oligonucleotide probes encoding various portions of the PTP-S31 (see below) are used to test cells from a subject for the presence of DNA or RNA sequences encoding the PTP. A preprobe would be one directed to the nucleic acid sequence encoding at least 4 amino acid residues, and preferably at least 5 amino acid residues, of the PTP-S31 protein or glycoprotein of the present invention. Qualitative or quantitative assays can be performed using such probes. For example, Northern analysis (see Examples, below) is used to measure expression of an PTP mRNA in a cell or tissue preparation.

Such methods can be used even with very small amounts of DNA obtained from an individual, following use of selective amplification techniques. Recombinant DNA methodologies capable of amplifying purified nucleic acid fragments have long been recognized. Typically, such methodologies involve the introduction of the nucleic acid fragment into a DNA or RNA vector, the clonal amplification of the vector, and the recovery of the amplified nucleic acid fragment. Examples of such methodologies are provided by Cohen et al. (U.S. Pat. No. 4,237,224), Sambrook et al., *MOLECULAR CLONING: A LABORATORY MANUAL*, Second Edition, Cold Spring Harbor Press, Cold Spring Harbor, N.Y. (1989), which references are herein incorporated by reference).

An in vitro enzymatic method which is capable of increasing the concentration of such desired nucleic acid molecules is referred to as the "polymerase chain reaction (PCR) (Mullis et al., *Cold spring Harbor Symp. Quant. Biol.* 51:263–273 (1986); Erlich et al., EP 50,424; EP 84,796, EP 258,017, EP 237,362; Mullis, K. EP 201,184; Mullis et al., U.S. Pat. No. 4,683,202; Erlich, H., U.S. Pat. No. 4,582,788; and Saiki et al., U.S. Pat. No. 4,683,194). The PCR provides a method for selectively increasing the concentration of a particular nucleic sequence even when that sequence has not been previously purified and is present only in a single copy in a particular sample. The method can be used to amplify either single- or double-stranded DNA. The essence of the method involves the use of two oligonucleotide probes to serve as primers for the template-dependent, polymerase mediated replication of a desired nucleic acid molecule.

The precise nature of the two oligonucleotide probes of the PCR method is critical to the success of the method. As is well known, a molecule of DNA or RNA possesses directionality, which is conferred through the 5'-3' linkage of the phosphate of the molecule. Sequences of DNA or RNA are linked together through the formation of a phosphodiester bond between the terminal 5' phosphate group of one sequence and the terminal 3' hydroxyl group of a second sequence. Polymerase dependent amplification of a nucleic acid molecule proceeds by the addition of a 5' nucleotide triphosphate to the 3' hydroxyl end of a nucleic acid molecule. Thus, the action of a polymerase extends the 3' end of a nucleic acid molecule. These inherent properties are exploited in the selection of the oligonucleotide probes of the PCR. The oligonucleotide sequences of the probes of the PCR are selected such that they contain sequences identical to, or complementary to, sequences which flank the particular nucleic acid sequence whose amplification is desired.

More specifically, the oligonucleotide sequences of the "first" probe is selected such that it is capable of hybridizing to an oligonucleotide sequence located 3' to the desired sequence, whereas the oligonucleotide sequence of the "second" probe is selected such that it contains an oligonucleotide sequence identical to one present 5' to the desired region. Both probes possess 3' hydroxy groups, and therefore can serve as primers for nucleic acid synthesis.

In the PCR, the reaction conditions are cycled between those conducive to hybridization and nucleic acid polymerization, and those which result in the denaturation of duplex molecules. In the first step of the reaction, the nucleic acids of the sample are transiently heated, and then cooled, in order to denature double-stranded molecules which may be present. The "first" and "second" probes are then added to the sample at a concentration which greatly exceed that of the desired nucleic acid molecule. When the sample is incubated under conditions conducive to hybridization and polymerization, the "first" probe will hybridize to the nucleic acid molecule of the sample at a position 3' to the sequence to be amplified. If the nucleic acid molecule of the sample was initially double-stranded, the "second" probe will hybridize to the complementary strand of the nucleic acid molecule at a position 3' to the sequence which is the complement of the sequence whose amplification is desired. Upon addition of a polymerase, the 3' ends of the "first" and (if the nucleic acid molecule was double-stranded) "second"

probes will be extended. The extension of the "first" probe will result in the synthesis of an oligonucleotide having the exact sequence of the desired nucleic acid. Extension of the "second" probe will result in the synthesis of an oligonucleotide having the exact sequence of the complement of the desired nucleic acid.

The PCR reaction is capable of exponential amplification of specific nucleic acid sequences because the extension product of the "first" probe, of necessity, contains a sequence which is complementary to a sequence of the "second" probe, and thus can serve as a template for the production of an extension product of the "second" probe. Similarly, the extension product of the "second" probe, of necessity, contains a sequence which is complementary to a sequence of the "first" probe, and thus can serve as a template for the production of an extension product of the "first" probe. Thus, by permitting cycles of polymerization, and denaturation, a geometric increase in the concentration of the desired nucleic acid molecule can be achieved. Reviews of the PCR are provided by Mullis, K. B. (*Cold spring Harbor Symp. Quant. Biol.* 51:263–273 (1986)); Saiki et al., *Bio/Technology* 3:1008–1012 (1985)); and Mullis et al., *Meth. Enzymol.* 155:335–350 (1987)).

5.4. PTP-S31 Proteins and Functional Derivatives

In one embodiment, the present invention is directed to a naturally occurring mammalian PTP-S31 protein or glycoprotein. In another embodiment, the invention is directed to a recombinant mammalian PTP-S31 protein or glycoprotein. The preferred PTP-S31 protein or glycoprotein of the present invention is of human origin. The invention provides the naturally occurring molecule substantially free of other proteins with which it is natively associated. "Substantially free of other proteins" indicates that the protein has been purified away from at least 90 percent (on a weight basis), and from even at least 99 percent if desired, of other proteins and glycoproteins with which it is natively associated, and is therefore substantially free of them. That can be achieved by subjecting the cells, tissue or fluids containing the RPTP to standard protein purification techniques such as immunoadsorbent columns bearing monoclonal antibodies reactive against the protein. Other forms of affinity purification can utilize solid-phase substrates which can bind the PTP domain, or a ligand that will bind to the receptor domain. Alternatively, the purification can be achieved by a combination of standard methods, such as ammonium sulfate precipitation, molecular sieve chromatography, and ion exchange chromatography.

In another embodiment, the present invention is directed to a peptide having an amino acid sequence corresponding to PTP-S31 or at least 9 contiguous amino acids thereof, more preferably at least 10, 15 20 or 30 contiguous amino acids thereof.

It will be understood that the mammalian PTP-S31 of the present invention can be biochemically purified from a variety of cell or tissue sources. For preparation of naturally occurring PTP-S31, mammalian skeletal muscle, especially of human origin, is preferred.

Alternatively, because the nucleic acid molecule encoding PTP-S31 can be isolated or synthesized, the polypeptide can be synthesized substantially free of other proteins or glycoproteins with which it is natively associated in a prokaryotic organism or in a non-mammalian eukaryotic organism, if desired. As intended by the present invention, a recombinant PTP-S31 molecule produced in mammalian cells, such as transfected cos, NIH-3T3, CHO, or 293 cells, etc., for example, is either a naturally occurring protein sequence or a functional derivative thereof. Where a naturally occurring protein is produced by recombinant means, it is provided substantially free of the other proteins and glycoproteins with which it is natively associated.

Alternatively, methods are well known for the synthesis polypeptides of desired sequence on solid phase supports and their subsequent separation from the support.

In a further embodiment, the invention provides "functional derivatives" of PTP-S31. By "functional derivative" is meant a "fragment," "variant," "analog," or "chemical derivative" of the PTP-S31, which terms are defined below. A functional derivative retains at least a portion of the function of the. PTP-S31, such as binding to a specific antibody or phosphatase enzymatic activity which permits its utility in accordance with the present invention.

A "fragment" of PTP-S31 refers to any subset of the molecule, that is, a shorter peptide. The term "fragment" is used to indicate a polypeptide which is derived from a PTP-S31 protein having a naturally occurring protein sequence by appropriately modifying the DNA sequence encoding the PTP-S31 protein, resulting in deletion of one or more amino acids at one or more sites of the C-terminal, N-terminal, and within the native sequence. Fragments of a PTP-S31 protein or glycoprotein are useful for screening for compounds that are antagonists or agonists (as defined below). It is understood that such fragments of a PTP-S31 protein or glycoprotein may retain characterizing portion(s) of the native PTP-S31. In particular, such fragments should retain one or more biological activities or functions which are characteristic for the intact PTP-S31 protein or glycoprotein. Examples, which are not intended to be in any way limiting to the scope of the invention claimed, of PTP-S31 fragments are: a) the catalytic domain; b) regions of the PTP-S31 protein or glycoprotein which interact with other molecules in the intact cell; c) regulatory parts of PTP-S31.

A "variant" of PTP-S31 refers to a molecule substantially similar to either the entire peptide or a fragment thereof. Variant peptides may be conveniently prepared by direct chemical synthesis of the variant peptide, using methods well known in the art.

Alternatively, amino acid sequence variants of the peptide can be prepared by mutations in the DNA which encodes the synthesized peptide. Such variants include, for example, deletions from, or insertions or substitutions of, residues within the amino acid sequence. Any combination of deletion, insertion, and substitution may also be made to arrive at the final constructs provided that the final construct possesses the desired activity. Obviously, the mutations that will be made in the DNA encoding the variant peptide must not alter the reading frame and preferably will not create complementary regions that could produce secondary mRNA structure (see European Patent Publication No. EP 75,444).

In a further aspect, the invention provides a PTP-S31 protein or glycoprotein having additional amino acids that is derived from a naturally occurring PTP-S31 protein or glycoprotein by appropriately modifying the DNA sequence encoding the protein, resulting in addition of one or more amino acids at one or more sites of the C-terminal, N-terminal, and within the native sequence. It is understood that such a PTP-S31 protein or glycoprotein having additional amino acids may retain characterizing portion(s) of the native PTP-S31 protein or glycoprotein. In particular, such a PTP-S31 protein or glycoprotein with additional amino acids should retain one or more biological activities or functions which are characteristic of the PTP-S31 protein or glycoprotein, examples of which include: (a) the catalytic activity; (b) the substrate specificity; (c) interaction with other molecules in the intact cell; (d) regulatory functions. These examples are not intended to be in any way limiting to the scope of the invention claimed.

In a further aspect, the invention provides a PTP-S31 protein or glycoprotein having substituted amino acids that is derived from a naturally occurring PTP-S31 protein or glycoprotein by appropriately modifying or mutating the DNA sequence encoding the protein, resulting in substitution of one or more amino acids at one or more sites of the C-terminal, N-terminal, and within the native amino acid sequence. It is understood that such a protein having substituted amino acids may retain characterizing portion(s) of PTP-S31, and should preferably retain one or more biological activities or functions which are characteristic for the intact PTP-S31 protein or glycoprotein, for example: (a) the catalytic activity; (b) the substrate specificity; (c) interaction with other molecules in the intact cell; d) regulatory functions. These examples are not intended to be in any way limiting to the scope of the invention claimed.

Any combination of deletion, insertion, and substitution may also be made to arrive at the final construct of a PTP-S31 functional derivative, provided that the final construct possesses the desired activity or function present in the intact PTP-S31 protein or glycoprotein, for example: (a) the catalytic activity; (b) substrate specificity; (c) interaction with other molecules in vitro and in vivo; (d) regulatory functions. Only one of such activities or functions needs to be retained after any combination of deletion, insertion, and substitution. These examples are not intended to be in any way limiting to the scope of the invention claimed. Obviously, the modifications or mutations that will be made in the DNA encoding the PTP-S31 protein must not alter the reading frame and preferably will not create complementary regions that could produce secondary mRNA structure (see European Patent Publication No. EP 75,444). At the genetic level, these variants ordinarily are prepared by site-directed mutagenesis (as exemplified by Adelman et al., *DNA* 2:183 (1983)) of nucleotides in the DNA encoding the peptide molecule, thereby producing DNA encoding the variant, and thereafter expressing the DNA in recombinant cell culture (see below). The variants typically exhibit the same qualitative biological activity as the nonvariant peptide.

An "analog" of PTP-S31 refers to a non-natural molecule substantially similar to either the entire molecule or a fragment thereof.

A "chemical derivative" of PTP-S31 contains additional chemical moieties not normally a part of the peptide. Covalent modifications o the peptide are included within the scope of this invention. Such modifications may be introduced into the molecule by reacting targeted amino acid residues of the peptide with an organic derivatizing agent that is capable of reacting with selected side chains or terminal residues.

Cysteinyl residues most commonly are reacted with α-haloacetates (and corresponding amines) such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylprocarbonate at pH 5.5–7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine ε-amino group.

Tyrosyl residues are well-known sites for chemical modification, in particular for introduction of spectral labels into tyrosyl residues by reaction with aromatic diazonium compounds or tetranitromethane. Most commonly, N-acetylimidizol and tetranitromethane are used to form O-acetyl tyrosyl species and 3-nitro derivatives, respectively.

Carboxyl side groups (aspartyl or glutamyl) are selectively modified by reaction with carbodiimides (R'—N—C—N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Derivatization with bifunctional agents is useful for cross-linking the peptide to a water-insoluble support matrix or other macromolecular carriers. Commonly used cross-linking agents include, e.g., 1-1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3dithiobis(succinimidyl-propionate), and bifunctional maleimides such as bis-N-maleimido-1,8-octane. Derivatizing agents such as methyl-3-[(p-azidophenyl)dithio]propioimidate intermediates that are capable of forming crosslinks in the presence of light. Alternatively, reactive water-insoluble matrices such as cyanogen bromide-activated carbohydrates and the reactive substrates described in U.S Pat. Nos. 3,969,287; 3,691,016; 4,195,128; 4,247,642, 4,229,537; and 4,330,440 are employed for protein immobilization.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecule Properties,* W.H. Freeman & Co., Francisco, pp. 79–86 (1983)), acetylation of the N-terminal and, in some instances, amidation of the C-terminal carboxyl groups.

Such derivatized moieties may improve the solubility, absorption, biological half life, and the like. The moieties may alternatively eliminate or attenuate any undesirable side effect of the protein and the like. Moieties capable-of mediating such effects are disclosed, for example, in *Remington's Pharmaceutical Sciences,* 16th ed., Hack Publishing Co., Easton, Pa. (1980).

5.5. Cheimeric PTP-S31 Molecules

In a further aspect, the invention provides so-called chimeric molecules which are made up of other PTPs in which one or more specific amino acid sequences are replaced with homologous sequence(s) from another PTP protein or glycoprotein. Chimeric molecules may include, for example, a receptor-type PTP (RPTP) protein or glycoprotein having a ligand-binding extracellular domain that is grafted onto a portion of a PTP-S31 protein or glycoprotein. Other chimeric molecules included within the scope of the present invention include PTPs in which the catalytic phosphatase domain has been replaced with the phosphatase domain from PTP-S31. In this case, the preferred number of amino acids is between 220 and 260.

"Homologous sequences" are defined as sequences in two or more PTPs which are similarly positioned in the primary sequence and which may exhibit sequence homology. It should be emphasized that "homologous sequences" should not be limited to cases with high degree of homology. Chimeric molecules are important tools for elucidating structure-function relationships and for identifying specific compounds (drugs). Therefore, the most useful chimeras are often, but not always, molecules in which a certain portion of one molecules has been replaced with the similarly positioned, but divergent, sequence from another, otherwise homologous, molecule. Thus, the exchanged portions will quite often represent the parts of the molecules where they differ the most.

5.6. Antibodies Specific for PTP-S31 and Their Uses in Detecting or Measuring PTP-s31

This invention is also directed to an antibody specific for an epitope of a PTP-S31 protein or glycoprotein, most preferably of human PTP-S31, and the use of such antibody to detect the presence of, or measure the quantity or concentration of the PTP-S31 protein or glycoprotein in a cell, a cell or tissue extract, or a biological fluid.

The term "antibody" is meant to include polyclonal antibodies, monoclonal antibodies (mAbs), chimeric antibodies, and anti-idiotypic (anti-Id) antibodies.

Polyclonal antibodies are heterogeneous populations of antibody molecules derived from the sera of animals immunized with an antigen.

Monoclonal antibodies are a substantially homogeneous population of antibodies to specific antigens. MAbs may be obtained by methods known to those skilled in the art. See, for example Kohler and Milstein *Nature* 256:495–497 (1975) and U.S. Pat. No. 4,376,110. Such antibodies may be of any immunoglobulin class including IgG, IgM, IgE, IgA, and IgD, and any subclass thereof. The hybridoma producing the mAbs of this invention may be cultivated in vitro or in vivo. Production of the high titers of mAbs in in vivo production makes this the presently preferred method of production. Briefly, cells from the individual hybridomas are injected intraperitoneally into pristane-primed BALB/c mice to produce ascites fluid with high concentrations of the desired mAbs. MAbs of isotype IgM or IgG may be purified from such ascites fluids, or from culture supernatants, using column chromatography methods well known to those of skill in the art.

Chimeric antibodies are molecules, different portions of which are derived from different animal species, such as those having variable region derived from a murine mAb and a human immunoglobulin constant region. Chimeric antibodies and methods for their production are known in the art (Cabilly et al., *Proc. Natl. Acad. Sci. USA* 81:3273–3277 (1984); Morrison et al., *Proc. Natl. Acad. Sci. USA* 81:6851–6855 (1984); Boulianne et al., *Nature* 312:643–646 (1984); Neuberger et al., *Nature* 314:268–270 (1985); Taniguchi et al., European Patent Application 171496 (Feb. 19, 1985); Morrison et al., European Patent Application 173494 (Mar. 5, 1986); Neuberger et al., PCT Application WO86/01533 (Mar. 13, 1986); Kudo et al., European Patent Application 184187 published Jun. 11, 1986); Morrison et al., European Patent Application 173494 (published Mar. 5, 1986); Sahagan et al., *J. Immunol.* 137:1066–1074 (1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988)). These references are hereby incorporated by reference.

An anti-idiotypic (anti-Id) antibody is an antibody which recognizes unique determinants generally associated with the antigen-binding site of an antibody. An anti-Id antibody can prepared by immunizing an animal of the same species and genetic type (e.g., mouse strain) as the source of the mAb with the mAb to which an anti-Id antibody is being prepared. The immunized animal will recognize and respond to the idiotypic determinants of the immunizing antibody by producing an antibody to these idiotypic determinants (the anti-Id antibody).

The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

Accordingly, mAbs generated against PTP-S31 may be used to induce anti-Id antibodies in suitable animals, such as BALB/c mice. Spleen cells from such immunized mice are used to produce anti-Id hybridomas secreting anti-Id mAbs. Further, the anti-Id mAbs can be coupled to a carrier such as keyhole limpet hemocyanin (KLH) and used to immunize additional BALB/c mice. Sera from these mice will contain anti-anti-Id antibodies that have the binding properties of the final mAb specific for a PTP-S31 epitope.

The anti-Id mAbs thus have their idiotypic epitopes, or "idiotopes" structurally similar to the epitope being evaluated, such as PTP-S31.

The term "antibody" is also meant to include both intact molecules as well as fragments thereof, such as, for example, Fab and F(ab')$_2$, which are capable of binding antigen. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)).

It will be appreciated that Fab and F(ab')$_2$ and other fragments of the antibodies useful in the present invention may be used for the detection and quantitation of PTP-S31 according to the methods disclosed herein for intact antibody molecules. Such fragments are typically produced by proteolytic cleavage, using enzymes such as papain (to produce Fab fragments) or pepsin (to produce F(ab')$_2$ fragments).

An antibody is said to be "capable of binding" a molecule if it is capable of specifically reacting with the molecule to thereby bind the molecule to the antibody. The term "epitope" is meant to refer to that portion of any molecule capable of being bound by an antibody which can also be recognized by that antibody. Epitopes or "antigenic determinants" usually consist of chemically active surface groupings of molecules such as amino acids or sugar side chains and have specific three dimensional structural characteristics as well as specific charge characteristics.

An "antigen" is a molecule or a portion of a molecule capable of being bound by an antibody which is additionally capable of inducing an animal to produce antibody capable of binding to an epitope of that antigen. An antigen may have one, or more than one epitope. The specific reaction referred to above is meant to indicate that the antigen will react, in a highly selective manner, with its corresponding antibody and not with the multitude of other antibodies which may be evoked by other antigens.

The antibodies, or fragments of antibodies, useful in the present invention may be used to quantitatively detect the presence of cells which express PTP-S31. This can be accomplished by immunofluorescence techniques employing a fluorescently labeled antibody (see below) coupled with light microscopic, flow cytometric, of fluorimetric detection.

The antibodies (or fragments thereof) useful in the present invention may be employed histologically, as in immunofluorescence of immunoelectron microscopy, for in situ detection of PTP-S31. In situ detection may be accomplished by removing a histological specimen from a patient, and providing a labeled antibody of the present invention to such a specimen. The antibody (or fragment) is preferably provided by applying or by overlaying the labeled antibody (or fragment) to a biological sample. Through the use of such a procedure, it is possible to determine not only the presence of the PTP but also its distribution on the examined tissue. Using the present invention, those of ordinary skill will readily perceive that any of a wide variety of histological methods (such as staining procedures) can be modified in order to achieve such in situ detection. Such assays for PTP-S31 typically comprises incubating a biological sample, such as a biological fluid, a tissue extract, freshly harvested cells such a lymphocytes or leucocytes, or cells which have been incubated in tissue culture, in the presence of a detectably labeled antibody capable of identifying PTP-S31, and detecting the antibody by any of a number of techniques well-known in the art.

The biological sample may be treated with a solid phase support such as nitrocellulose, or other solid support which is capable of immobilizing cells, cell particles or soluble proteins. The support may then be washed with suitable buffers followed by treatment with the detectably labeled PTP-S31-specific antibody. The solid phase support may then be washed with the buffer a second time to remove unbound antibody. The amount of bound label on said solid support may then be detected by conventional means.

By "solid phase support" is intended any support capable of binding antigen or antibodies. Well-known supports, or carriers, include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-PTP-S31 antibody may be determined according to well known methods. Those skilled in the art will be able to determine operative and optimal assay conditions for each determination by employing routine experimentation.

Other such steps as washing, stirring, shaking, filtering and the like may be added to the assays as is customary or necessary for the particular situation.

One of the ways in which the PTP-S31-specific antibody can be detectably labeled is by linking the same to an enzyme and use in an enzyme immunoassay (EIA). This enzyme, in turn, when later exposed to an appropriate substrate, will react with the substrate in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, α-glycerophosphate dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection may also be accomplished by visual comparison of the extent of enzymatic reaction of a substrate in comparison with similarly prepared standards.

Detection may be accomplished using any of a variety of other immunoassays. For example, by radioactively labeling the antibodies or antibody fragments, it is possible to detect RPTP through the use of a radioimmunoassay (RIA) (see, for example, Work, T. S. et al., *Laboratory Techniques and Biochemistry in Molecular Biology*, North Holland Publishing Company, New York, 1978, which is incorporated by reference herein). The radioactive isotope can be detected by such means as the use of a gamma counter, or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labelling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethyl enetriaminepentaacetic acid (DTPA) or ethylenediaminetetraacetic acid (EDTA).

The antibody also can be detestably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

The antibody molecules of the present invention may be adapted for utilization in an immunometric assay, also known as a "two-site" or "sandwich" assay. In a typical immunometric assay, a quantity of unlabeled antibody (or fragment of antibody) is bound to a solid support and a quantity of detectably labeled soluble antibody is added to permit detection and/or quantitation of the ternary complex formed between solid-phase antibody, antigen, and labeled antibody.

Typical, and preferred, immunometric assays include "forward" assays in which the antibody bound to the solid phase is first contacted with the sample being tested to extract the antigen from the sample by formation of a binary solid phase antibody-antigen complex. After a suitable incubation period, the solid support is washed to remove the residue of the fluid sample, including unreacted antigen, if any, and then contacted with the solution containing an unknown quantity of labeled antibody (which functions as a "reporter molecule"). After a second incubation period to permit the labeled antibody to complex with the antigen bound to the solid support through the unlabeled antibody, the solid support is washed a second time to remove the unreacted labeled antibody.

In another type of "sandwich" assay, which may also be useful with the antigens of the present invention, the so-called "simultaneous" and "reverse" assays are used. A simultaneous assay involves a single incubation step as the antibody bound to the solid support and labeled antibody are both added to the sample being tested at the same time. After the incubation is completed, the solid support is washed to remove the residue of fluid sample and uncomplexed labeled antibody. The presence of labeled antibody associated with the solid support is then determined as it would be in a conventional "forward" sandwich assay.

In the "reverse" assay, stepwise addition first of a solution of labeled antibody to the fluid sample followed by the addition of unlabeled antibody bound to a solid support after a suitable incubation period is utilized. After a second incubation, the solid phase is washed in conventional fashion to free it of the residue of the sample being tested and the solution of unreacted labeled antibody. The determination of labeled antibody associated with a solid support is then determined as in the "simultaneous" and "forward" assays.

The presence of normally functioning PTP-S31 in a subject can also be tested using direct enzymatic assays, preferably for the tyrosine phosphatase activity. Such biochemical measurements can be performed in vitro, using purified enzymes, allowing precise measurements of enzyme activity, or with membrane preparations, or whole cells, where the net phosphotyrosine level is determined.

5.7. Nucliec Acid Molecule Encoding PTP-S31

In additional embodiments of the present invention, a DNA sequence encoding a PTP-S31 molecule and methods for expressing the DNA sequence are provided. One of ordinary skill in the art will know how to identify and clone additional PTP molecules, of human or other mammalian species, which have sequence homology to the PTP-S31 protein and functional derivatives described herein, using the genetic sequences and oligonucleotides of the present invention without undue experimentation.

In one embodiment, the present invention is directed to an isolated nucleic acid molecule encoding a polypeptide having the amino acid sequence of PTP-S31, or having at least 9 contiguous amino acids thereof preferably at least 10, 15, 20 or 30 contiguous amino acids. In a preferred embodiment, the isolated nucleic acid encodes a polypeptide having the amino acid sequence SEQ ID NO:4 or a mutant or species variant thereof. In another preferred embodiment, the isolated nucleic acid sequence comprises SEQ ID NO:3, or at least 27 contiguous nucleotides thereof, preferably at least 30, 35, 40 or 50 nucleotides thereof.

Manipulation of the genetic constructs of the present invention allows the grafting of a particular ligand-binding receptor domain and transmembrane domain of an RPTP to a catalytic portion of PTP-S31 resulting in chimeric molecules. Non-limiting examples of such chimeric molecules include a PTP wherein the receptor is an epidermal growth factor receptor, a fibroblast growth factor receptor, and the like. Also contemplated are PTP-PTP chimeras, for example, between PFP-S31 and PTPα or PTPε. Genetically engineered chimeric receptors are known in the art (see, for example, Riedel, H. et al., *Nature* 324:628–670 (1986)).

Genetic constructs encoding-PTP-S31, functional derivatives thereof, and chimeric molecules such as those described above, can be used in gene therapy. An abnormal or dysfunctional PTP-S31, which results in disease, may be replaced by infusion of cells of the desired lineage (such as hemopoietic cells, for example) transfected with DNA encoding normal PTP-S31. Alternatively, or additionally, cells carrying a chimeric RPTP having a receptor to a ligand of choice (e.g. EGF) can be used for such gene therapy.

The recombinant DNA molecules of the present invention can be produced through any of a variety of means, such as, for example, DNA or RNA synthesis, or more preferably, by application of recombinant DNA techniques. Techniques for synthesizing such molecules are disclosed by, for example, Wu, R., et al. (*Prog. Nucl. Acid. Res. Molec. Biol.* 21:101–141 (1978)). Procedures for constructing recombinant molecules in accordance with the above-described method are disclosed by Sambrook et al. (supra).

The 3' terminus of the recombinant molecule of this invention is preferably treated to render it unsuitable for polymerization. Such treatment may be accomplished by blocking the terminus by chemical means, or by modifying the terminal bases such that they sterically interfere with polymerase action. In a preferred embodiment, such treatment is accomplished by immobilizing the 3' terminus, such as by coupling it to a solid support (such as, for example, glass, plastic, latex, etc.). The support may be of any form (i.e. a sheet, rod, sphere, ovoid, etc.). Procedures for such immobilization are well known to those of ordinary skill. In the most preferred embodiment, the 3' end of the recombinant molecule is covalently bound to the solid support. A spacer region may be used to extend the probe outward from the solid support as long as (1) it will not sterically hinder any function or characteristic of the recombinant molecule, and (2) the sequence of the spacer region does not participate in the hybridization or polymerization reactions of the assay. It is typically desirable to immobilize several, and preferably, a large number of such recombinant molecule to the support.

Oligonucleotides representing a portion of PTP-S31 are useful for screening for the presence of genes encoding such proteins and for the cloning of PTP-S31 genes. Techniques for synthesizing such oligonucleotides are disclosed by, for example, Wu, R., et al., *Prog. Nucl. Acid. Res. Molec. Biol.* 21:101–141 (1978)).

Protein molecules are fragmented as with cyanogen bromide, or with proteases such as papain, chymotrypsin, trypsin, etc. (Oike, Y., et al., *J. Biol. Chem.* 257:9751–9758 (1982); Liu, C., et al., *Int. J. Pept. Protein Res.* 21:209–215 (1983)). Because the genetic code is degenerate, more than one codon may be used to encode a particular amino acid (Watson, J. D., In: *Molecular Biology of the Gene,* 4th Ed., Benjamin/Cummings Publishing Co., Inc., Menlo Park, Calif. (1987)). Using the genetic code, one or more different oligonucleotides can be identified, each of which would be capable of encoding the amino acid. The probability that a particular oligonucleotide will, in fact, constitute the actual XXX-encoding sequence can be estimated by considering abnormal base pairing relationships and the frequency with which a particular codon is actually used (to encode a particular amino acid) in eukaryotic cells. Such "codon usage rules" are disclosed by Lethe, R., et al., *J. Molec. Biol.* 183:1–12 (1985). Using the "codon usage rules" of Lathe, a single oligonucleotide, or a set of oligonucleotides, that contains a theoretical "most probable" nucleotide sequence capable of encoding an PTP-S31 sequence is identified.

Although occasionally an amino acid sequence may be encoded by only a single oligonucleotide, frequently the amino acid sequence may be encoded by any of a set of similar oligonucleotides. Importantly, whereas all of the members of this set contain oligonucleotides which are capable of encoding the peptide fragment and, thus, potentially contain the same oligonucleotide sequence as the gene which encodes the peptide fragment, only one member of the set contains the nucleotide sequence that is identical to the nucleotide sequence of the gene. Because this member is present within the set, and is capable of hybridizing to DNA even in the presence of the other members of the set, it is possible to employ the unfractionated set of oligonucleotides in the same manner in which one would employ a single oligonucleotide to clone the gene that encodes the peptide.

The oligonucleotide, or set of oligonucleotides, containing the theoretical "most probable" sequence capable of encoding a PTP-S31 fragment is used to identify the sequence of a complementary oligonucleotide or set of oligonucleotides which is capable of hybridizing to the "most probable" sequence, or set of sequences. An oligonucleotide containing such a complementary sequence can be employed as a probe to identify and isolate the PTP-S31 (sambrook et al., supra).

A suitable oligonucleotide, or set of oligonucleotides, which is capable of encoding a fragment of an PTP-S31 gene (or which is complementary to such an oligonucleotide, or set of oligonucleotides) is identified (using the above-described procedure), synthesized, and hybridized by means well known in the art, against a DNA or, more preferably, a cDNA preparation derived from cells which are capable of expressing the PTP-S31 gene. Single stranded oligonucleotide molecules complementary to the "most probable" PTP-S31 peptide-encoding sequences can be synthesized using procedures which are well known to those of ordinary skill in the art (Belagaje et al., *J. Biol. chem. Mechanisms in the Control of Gene Expression;* Nierlich et al., Eds., Acad. Press, NY (1976); Wu et al., *Prog. Nucl. Acid Res. Molec. Biol.* 21:101–141 (1978); Khorana, R. G., *Science* 203:614–625 (1979)). Additionally, DNA synthesis may be achieved through the use of automated synthesizers. Techniques of nucleic acid hybridization are disclosed by Sambrook et al. (supra), and by Haymes et al. (In: *Nucleic Acid Hybridization, A Practical Approach,* IRL Press, Washington, D.C. (1985)), which references are herein incorporated by reference. Techniques such as, or similar to, those described above have successfully enabled the cloning of genes for human aldehyde dehydrogenases (Hsu et al., *Proc. Natl. Acad. Sci. USA* 82:3771–3775 (1985), fibronectin (Suzuki et al.*EMBO J.* 4:2519–2524 (1985), the human estrogen receptor gene (Walter et al., *Proc. Natl. Acad. Sci. USA* 82:7889–7893 (1985)), tissue-type plasminogen activator (Pennica et al., *Nature* 301:214–221 (1983)), and human term placental alkaline phosphatase complementary DNA (Dam et al., *Proc. Natl. Acad. Sci. USA* 82:715–8719 (1985)).

In an alternative way of cloning the PTP-S31 gene, a library of expression vectors is prepared by cloning DNA or, more preferably, cDNA (from a cell capable of expressing PTP-S31) into an expression vector. The library is then screened for members capable of expressing a protein which binds to an anti-PTP-S31 antibody, and which has a nucleotide sequence that is capable of encoding polypeptides that have the same amino acid sequence as PTP-S31, or fragments thereof. In this embodiment, DNA, or more preferably cDNA, is extracted and purified from a cell which is capable of expressing PTP-S31 protein. The purified cDNA is fragmented (by shearing, endonuclease digestion, etc.) to produce a pool of DNA or cDNA fragments. DNA or cDNA fragments from this pool are then cloned into an expression vector in order to produce a genomic library of expression vectors whose members each contain a unique cloned DNA or cDNA fragment.

An "expression vector" is a vector which (due to the presence of appropriate transcriptional and/or translation control sequences) is capable of expression a DNA (or cDNA) molecule which has been cloned into the vector and of thereby producing a polypeptide or protein. Expression of the cloned sequences occurs when the expression vector is introduced into an appropriate host cell. If a prokaryotic expression vector is employed, then the appropriate host cell would be any prokaryotic cell capable of expressing the cloned sequences. Similarly, if a eukaryotic expression vector is employed, then the appropriate host cell would be any eukaryotic cell capable of expressing the cloned sequences. Importantly, since eukaryotic DNA may contain intervening sequences, and since such sequences cannot be correctly processed in prokaryotic cells, it is preferable to employ cDNA from a cell which is capable of expressing PTP-S31 in order to produce a prokaryotic genomic expression vector library. Procedures for preparing cDNA and for producing a genomic library are disclosed by Sambrook et al. (supra).

A DNA sequence encoding PTP-S31 or its functional derivatives, may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulations are disclosed by Sambrook et al., supra, and are well known in the art.

A nucleic acid molecule, such as DNA, is said to be "capable of expressing" a polypeptide if it contains nucleotide sequences which contain transcriptional and translational regulatory information and such sequences are "operably linked" to nucleotide sequences which encode the polypeptide. An operable linkage is a linkage in which the regulatory DNA sequences and the DNA sequence sought to be expressed are connected in such a way as to permit gene expression. The precise nature of the regulatory regions needed for gene expression may vary from organism to organism, but shall in general include a promoter region which, in prokaryotes, contains both the promoter (which directs the initiation of RNA transcription) as well as the DNA is sequences which, when transcribed into RNA, will signal the initiation of protein synthesis. Such regions will normally include those 5'-non-coding sequences involved with initiation of transcription and translation, such as the TATA box, capping sequence, CAAT sequence, and the like.

If desired, the non-coding region 3' to the gene sequence coding for the protein may be obtained by the above-described methods. This region may be retained for its transcriptional termination regulatory sequences, such as termination and polyadenylation. Thus, by retaining the 3'-region naturally contiguous to the DNA sequence coding for the protein, the transcriptional termination signals may be provided. Where the transcriptional termination signals are not satisfactorily functional in the expression host cell, then a 3' region functional in the host cell may be substituted.

Two DNA sequences (such as a promoter region sequence and a PTP-S31-encoding sequence) are said to be operably linked if the nature of the linkage between the two DNA sequences does not (1) result in the introduction of a frame-shift mutation, (2) interfere with the ability of the promoter region sequence to direct the transcription of the R-PTP gene sequence, or (3) interfere with the ability of the R-PTP gene sequence to be transcribed by the promoter region sequence. A promoter region would be operably linked to a DNA sequence if the promoter were capable of effecting transcription of that DNA sequence. Thus, to express the protein, transcriptional and translational signals recognized by an appropriate host are necessary.

A promoter is a double-stranded DNA or RNA sequence which is capable of binding RNA polymerase and promoting the transcription of an "operably linked" nucleic acid sequence. As used herein, a "promoter sequence" is the sequence of the promoter which is found on that strand of the DNA or RNA which is transcribed by the RNA polymerase. A "promoter sequence complement" is a nucleic acid molecule whose sequence is the complement of a "promoter sequence." Hence, upon extension of a primer DNA or RNA adjacent to a single-stranded "promoter sequence complement" or of a "promoter sequence," a double-stranded molecule is created which will contain a functional promoter, if that extension proceeds towards the "promoter sequence" or the "promoter sequence complement." This functional promoter will direct the transcription of a nucleic acid sequence which is operably linked to that strand of the double-stranded molecule which contains the "promoter sequence".

Certain RNA polymerases exhibit a high specificity for such promoters. The RNA polymerases of the bacteriophages T7, T3 and SP-6 are especially well characterized, and exhibit high promoter specificity. The promoter sequences which are specific for each of these RNA polymerases also direct the polymerase to transcribe only one strand of the two strands of a duplex DNA template. The selection for which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner which either permits both sequences to be transcribed onto the same RNA transcript, or permits an RNA transcript, begun in one sequence to be extended into the second sequence. Thus, two sequences, such as a promoter sequence and any other "second" sequence of DNA or RNA are operably linked if transcription commencing in the promoter sequence will produce an RNA transcript of the operably linked second sequence. In order to be "operably linked" it is not necessary that two sequences be immediately adjacent to one another.

The promoter sequences of the present invention may be either prokaryotic, eukaryotic or viral. Suitable promoters are repressible, or, more preferably, constitutive. Examples of suitable prokaryotic promoters include promoters capable of recognizing the T4 (Malik, S., et al., *J. Biol. Chem.* 263:1174–1181 (1984); Rosenberg, A. H., et al., *Gene* 59:191–200 (1987); Shinedling, S., et al., *J. Molec. Biol.* 195:471–480 (1987); Hu, M., et al., *Gene* 42:21–30 (1986)), T3, Sp6, and T7 (Chamberlin, M., et al., *Nature* 228:227–231 (1970); Bailey, J. N., et al., *Proc. Natl. Acad. Sci. USA* 80:2814–2818 (1983); Davanloo, P., et al., *Proc. Natl. Acad. Sci. USA* 81:2035–2039 (1984)) polymerases; the $P_R$ and $P_L$ promoters of bacteriophage lambda (*The Bacteriophage Lambda,* Hershey, A. D., ed., Cold Spring Harbor Press, Cold Spring Harbor, N.Y. (1973); Lambda II, Hendrix, R. W., ed., Cold Spring Harbor Press, Cold Spring Harbor, N.Y. (1980)); the trp, recA, heat shock, and lacZ promoters of *E. coli;* the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of Bacillus (Gryczan, T. J., in: *The Molecular Biology of the Bacilli,* Academic Press, Inc., NY (1982)); Streptomyces promoters (Ward, J. M., et al., *Mol. Gen. Genet.* 203:468–478 (1986)); the int promoter of bacteriophage lambda; the bla promoter of the β-lactamase gene of pBR322, and the CAT promoter of the chloramphenicol acetyl transferase gene of pPR325, etc. Prokaryotic promoters are reviewed by Glick, B. R. (*J. Ind. Microbiol.* 1:277–282 (1987)); Cenatiempo, Y. (Biochimie 68:505–516 (1986)); Watson, J. D., et al., in *Molecular Biology of the Gene,* Fourth Edition, Benjamin Cummins, Menlo Park, Calif. (1987)); and Gottesman, S. (*Ann. Rev. Genet.* 18:415–442 (1984)). Preferred eukaryotic promoters include the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)) ; the SV40 early promoter (Benoist, C., et al., *Nature (London)* 290:304–310 (1981)); and the yeast gal4 gene promoter (Johnston, S. A., et al., *Proc. Natl. Acad. Sci. USA* 79:6971–6975 (1982); Silver, P. A., et al., *Proc. Natl. Acad. Sci. USA* 81:5951–5955 (1984)). All of the above listed references are incorporated by reference herein.

Strong promoters are preferred. Examples of such referred promoters are those which recognize the T3, SP6 and T7 polymerases, the PL promoter and the promoter of the mouse metallothionein I gene. A most preferred promoter for eukaryotic expression of PTP-S31 is an SV40 promoter such as that driving transcription in the pLSV vector (Livneh, E., et al., *J. Biol. Chem.* 261:12490–12497 (1986)). The sequences of such polymerase recognition sites are disclosed by Watson, J. D., et al. (in: *Molecular Biology of the Gene,* 4th ed., Benjamin/Cummings Publishing Co., Inc., Menlo Park, Calif. (1987)).

Having now generally described the invention, the same will be more readily understood through reference to the following example which is provided by way of illustration, and is not intended to be limiting of the present invention, unless specified.

6. EXAMPLE

Identification of a Novel PTP Using the Polymerase Chain Reaction

To identify novel PTPs in insulin-sensitive tissues, the present inventors employed the PCR technique. First strand cDNA from skeletal muscle was used as template and degenerate oligonucleotides corresponding to highly conserved regions were used as primers. A number of already characterized PTPs were identified (such as RPTPα, RPTPβ, RPTPγ, PTP 1B, T cell PTP, MEG1) using the approach described below. In addition, a novel PTP, named PTP-S31, was discovered.

Total RNA was isolated from human skeletal muscle by the guanidinium thiocyanate/CsCl procedure (Chirgwin et al., *Biochem.* 18:5293–5299 (1979)). Poly(A)⁺ RNA was isolated on an oligo(dT) cellulose column (Aviv et al.; *Proc. Natl. Acad. Sci. USA* 58:1408–1412 (1972)). First strand cDNA was synthesized from 2 µg poly(A)⁺ RNA using oligo(dT) priming and Moloney Murine Leukemia Virus RNase H⁻ Reverse Transcriptase from GIBCO BRL (Gaithersburg, Md. USA) in accordance with the manufacturer's recommendations.

cDNA corresponding to PTPs expressed in-skeletal muscle were isolated after PCR (Saiki et al., *Science* 239:487–491 (1988)). The human skeletal muscle first strand cDNA from above (corresponding to about 50 ng) was amplified with the following set of mixed degenerative oligonucleotide primers using the Gene Amp kit (Perkin Elmer Cetus, Norwalk, Conn., USA).

Sense primer (oligonucleotide no. 58):

5' A(CT)TT(CT)TGG(ACG)(AG)(AG)ATG(AG)T(TCGA)TGG 3' [SEQ ID NO:28]

which corresponds to the PTP amino acid consensus sequence: F W X M X W (SEQ ID NO:46)

Anti-sense primer (oligonucleotide no:57):

5' CC(TCGA)A(CT)(AGT)CC(ATC)GC(AG)CT(GA)CAGTG 3' [SEQ ID NO:29]

which corresponds to the PTP amino acid consensus sequence: HCSAG(S/I/V)G [SEQ ID NO:41].

Each PCR cycle comprised a denaturation step at 94° C. for 1 minute, an annealing step at 37° C. for 2 minutes, and an extension step at 72° C. for 2 minutes. Thirty to 40 cycles were carried out. The reaction products were subjected to agarose gel electrophoresis. The fragments of the expected size (based on the structure of already described PTPs) were isolated, subcloned using the TA cloning system (Invitrogen, San Diego, Calif.) and sequenced by the enzymatic chain termination method described by Sanger et al., *Proc. Natl. Acad. Sci. USA* 74:5463–5467 (1977)), (Sequenase, U.S. Biochemicals) using standard techniques (Ausubel et al., eds., *Current Protocols in Molecular Biology*, John Wiley & Sons, New York, 1988).

The partial DNA sequence and the deduced amino acid sequence of a PCR fragment, termed PTP-S31, is shown in FIG. 1.

The deduced amino acid sequence of PTP-S31 is compared with PTP 1B (Chernoff et al., supra) in FIG. 2 using the GAP alignment method (Needleman et al., supra).

PTP-S31 is clearly homologous to other known PTPs, but, surprisingly, has a feature not yet described for this class of enzymes, as analyzed by the University of Wisconsin, Genetics Computer Group program. This unique feature of PTP-S31 is shown below in comparison with the consensus sequences of the previously described known PTPs (the difference is underlined):

PTP-S31: R C X X Y W P [SEQ ID NO:30]
Consensus: K C X X Y W P [SEQ ID NO:1]

7. EXAMPLE cDNA Cloning of a Member of the PTP-S31 Subfamily mRNA was prepared from the rhabdomyosarcoma cell line RD (ATCC #CCL 136) as described above in Section 6. A cDNA library (library # 1) was constructed using the methods described by Okayama and Berg (*Mol. Cell. Biol.* 2:161–170 (1982); *Mol. Cell. Biol.* 3:280–289 (1983)).

The pCDVI-PL vector was used for preparation of the primer fragment (Noma et al., *Nature* 319:640–646 (1986). A short synthetic adapter was used as second strand primer (Boel et al., *BioTechniques* 11:26–28 (1991)). *E. coli* DH5α (Gibco BRL, Gaithersburg, Md., USA) was used for transformation (Inuoue, H. et al., *Gene* 96:23–28 (1990)). After transformation, the cells were plated onto LB plates (containing 50 µg ampicillin/ml) at a density of 15,000–20,000 colonies per plate.

Nittocellulose replica filters (Schleicher & Schuell, BA85) were screened with standard colony hybridization technique (Sambrook, J. et al., *Molecular Cloning: A Laboratory Manual*, 2nd Edition, Cold Spring Harbor Press, Cold Spring Harbor, N.Y. (1989)). The following oligonucleotide (#185) was synthesized, labeled at the 5' end using $T_4$ polynucleotide kinase and $[\gamma-^{32}P]$ATP (Amersham) and used for screening of the cDNA library:

5' CCA TCA GTA TTG GCC AGA GG 3' [SEQ ID NO:31]

This oligonucleotide corresponds to the amino acid sequence His-Gln-Tyr-Trp-Pro-Glu (SEQ ID NO:42) of the PTP-S31 PCR fragment described in Section 6. Ten pmoles of the labeled oligonucleotide in 50 ml of hybridization solution (6×SSC, 5×Denhardt's solution, 0.05% SDS (Ausubel et al., supra) were added to replica nitrocellulose filters and allowed to hybridize at 42° C. for 3 hours. Then the filters were washed in 6×SSC, 0.05% SDS three times at room temperature, once at 42° C. and finally once at 48° C. One positive colony (clone 1.20.4) was identified by autoradiography, isolated and sequenced by standard techniques ((Sambrook et al., supra).

The nucleotide sequence of this clone, now denoted PTP-S31C [SEQ ID NO:6] and the deduced amino acid sequence [SEQ ID NO:7] are shown in FIGS. 3A–3D. This sequence includes the sequence of the PCR fragment from above and thus confirms the identity of the isolated cDNA clone. The size of this clone PTP-S31C is about 2300 bp. It contains two in-frame, putative methionine initiator codons followed by an open reading frame encoding a protein of about 39 kDa. The first ATG conforms with a consensus translation initiation sequence (Kozak, M. *Nucleic Acids Research* 15: 8125–8148 (1984)). Furthermore, the distance from the 5' end of the PTP domain (N(K/R)XXXNR) (SEQ ID NO:43) to the initiator codon is similar to that of other PTPS, e.g., PTP 1B (Chernoff et al., supra) and PEP (Matthews et al., supra). However, there is no in-frame stop codon 5' of the first ATG. It is, therefore, possible that PTP-S31C is not a full-length clone.

PTP-S31C contains most of the conserved amino acid residues found in other PTPs; the amino acid sequence is about 45% identical to previously described PTPs. PTP-S31 lacks a signal peptide and a transmembrane region and might therefore belong to the class of small, intracellular PTPs. Unexpectedly, however, the deduced amino acid sequence around the catalytically essential cysteine residue differed markedly from the consensus sequence: HCSXGXGRXG [SEQ ID NO:32]. It is especially noteworthy that the arginine in position 6 C-terminal from the active site cysteine in other PTPs is replaced with phenylalanine in PTP-S31C. This arginine residue has been found to be conserved in all PTPs described, including PTPs which lack many other features common to most PTPs, for example, cdc25 (Sahdu et al., supra) and the tyro-sine/serine phosphatase encoded by vaccinia virus (Guan et al., supra).

In addition, the remainder of the C terminus aligns only poorly with known PTPs. An alignment of PTP 1B (Chernoff et al., supra) and PTP-S31C is shown in FIGS. 4A–4B.

8. EXAMPLE

Identification of PTP-S31D, an Alternative Form of the Novel PTP

The findings disclosed in Section 7, which appeared somewhat puzzling at first to the present inventors, were subjected to a careful inspection of the sequence around the active site cysteine. This analysis revealed, in a different reading frame, a motif which is commonly seen in the C-terminal part of PTP domains: QYIFXXXXXXD (SEQ ID NO:44) (Krueger et al., *EMBO J*. 9: 3241–3252 (1990)).

To analyze if this was a cloning artifact or a very unusual form of alternative splicing, two sets of PCR primers were designed (two primers on each side of the active site cysteine) as follows:

Primer Set #1
Sense primer (oligonucleotide no. 223)
    5' GACGGATCCGATGCCATCAGTATTGG 3' [SEQ ID NO:33]
Anti-sense primer (oligonucleotide no. 224)
    5' TGGTCTAGATATTTACATAGTGGTT 3' [SEQ ID NO:34]
Primer Set #2
Sense primer (oligonucleotide no. 185)
    5' CCATCAGTATTGGCCAGAGG 3' [SEQ ID NO:35]
Anti-sense primer (oligonucleotide no. 225)
    5' CAAGCTCAACATCACCTTCCA 3' [SEQ ID NO:36]

PCR on PTP-S31C cDNA yielded a band of around 450 bp with primer set #1 and about 430 bp with primer set #2. If a deletion or an alternative splicing event had taken place it should be possible to detect an additional band by PCR directly on first strand cDNA from the RD cell line and/or skeletal muscle. The expected size of this band would be 430/450 bp plus the distance normally seen in PTPs between the active site cysteine and the QYIF-motif, i.e., around 130 bp.

mRNA and 1st strand cDNA was prepared from the rhabdomyosarcoma cell line RD (American Tissue Type Collection CCL 136) and human skeletal muscle as described in Section 6. About 50 ng of first strand cDNA were used with the above primers. Each PCR cycle comprised a denaturation step at 94° C. for 1 minute, an annealing step at 37° C. for 2 minutes, and an extension step at 72° C. for 2 minutes. Thirty to 40 cycles were carried out. The PCR fragments were analyzed by standard agarose gel electrophoresis (Ausubel et al., supra). Primer set # 1 gave rise to two bands of the predicted sizes using cDNA from the RD cell line as template. Primer set # 2 gave rise to two bands of the predicted sizes in the RD cell line as wells as in skeletal muscle cDNA.

Both bands from the RD cell line obtained with primer set #1 were cloned and sequenced. As expected, it was found that the lower band corresponds to the PTP S31C sequence. The upper band also has a sequence identical to the PTP S31C sequence but with a 133 bp insertion (FIGS. 5A–5B). The upper band obtained with primer set #2 using skeletal muscle cDNA was sequenced directly using the anti-sense primer oligonucleotide no. 225. Identical sequences were found in the RD cell line and skeletal muscle. The deduced amino acid sequence of this region now shows the usual features of PTPs including the HCSXGXGR (SEQ ID NO:45) sequence and is in frame with the 5' end of PTP S31C. This novel form of PTP was designated PTP S31D. The combined sequence of PTP-S31C and PTP-S31D is shown in FIGS. 6A–6D.

FIG. 7 shows an alignment of PTP S31D with the first PTP domains of CD45 (Ralph et al., supra) and LAR (Streuli et al., supra), respectively, and with the PTP domain of PTP 1B (Chernoff et al., supra). The CLUSTAL program was used (Higgins et al., supra).

9. EXAMPLE

Insertion of the S31D Fragment into the PTP-S31C

The following three basic steps were employed:
1. A BspHI site was introduced at the first ATG in PTP-S31C.
2. This BspHI site was used to transfer the coding region of PTP-S31C into the vector pSP72 (Promega).
3. The S31D sequence was introduced into the PTP-S31 sequence.

Step 1
To facilitate the introduction of the PTP-S31 sequence into different cloning vectors we introduced a BamHI and a BspHI site (using PCR) upstream of the first Met in the sequence of PTP-S31C:
Sense primer (oligonucleotide no. 202: BamHI/BspHI):
    5' CGGGATCCATCATGAGAATGAGGCCAATAAGC 3 [SEQ ID NO:37]
Anti-sense primer (oligonucleotide no. 203: XbaI):
    5' GCTCTAGAGCTTGTAATCACTATATCTCCA 3' [SEQ ID NO:38]

About 100 ng of plasmid DNA from PTP-S31C (clone 1.20.4) were used as template. Each PCR cycle comprise a denaturation step at 94° C. for 1 minute, an annealing step at 50° C. for 2 minutes, and an extension step at 72° C. for 2 minutes. Ten cycles were performed. The PCR fragments were analyzed by agarose gel electrophoresis, digested with BamHI and AlwNI and a 470 bp fragment was isolated using standard techniques (Ausubel et al., supra). This fragment corresponds to the 5' end of PTP-S31C and contains the coding region of PTP-S31 starting with the first methionine.

Step 2
Using standard techniques a 940 bp fragment was isolated from the original PTP-S31C clone (1.20.4) by digesting with AlwNI and EcoRV. This fragment is combined with the PCR fragment isolated in Step 1 and ligated into the pSP72 vector (Promega) which is digested with BamHI and EcoRV. The resulting plasmid is termed pSP-S31C.

Step 3
The upper band (about 580 bp including the S31D sequence) from the PCR described in Section 8 (Primer set #1) was cloned into the pBluescript KS+ vector (Stratagene, La Jolla, Calif.) using convenient restriction sites (BamHI/XbaI) which were included in the primers (oligonucleotides no. 223 and 224, respectively). The resulting plasmid was in turn digested with DraIII and NcoI giving rise to a 330 bp fragment spanning the S31D sequence which was inserted in the plasmid pSP-S31 C (Step 2) digested with the same enzymes (PraIII/NcoI). The resulting plasmid is termed pSP-S31D.

10. EXAMPLE

Analysis of PTP Enzymatic Activity of PTP-S31D 10.1. Change of the Prokaryotic Enzymatic Vector pGEX To accommodate a cDNA fragment from PTP S31D (see below) the cloning sites of the pGEX2T vector (Pharmacia, Uppsala, Sweden) were changed using standard techniques (*Current Protocols in Molecular Biology*, eds. F. M. Ausubel et al., John Wiley & Sons, New York, 1988). The pGEX2T vector was digested with the restriction enzymes BamHI and EcoRI and isolated. The following oligonucleotides were ligated into the digested pGEX2T vector.

5' GATCTCCGAATTCCATGGATCCAGGC-
CTCTAGAAGCTTAC 3' [SEQ ID NO:39]
3' AGGCTTAAGGTACCTAGGTCCG-
GAGATCTTCGAATGTTAA 5' [SEQ ID NO:40]
thereby giving rise to the vector pGEX-αK2 with the following cloning sites:
5' EcoRI, NcoI, BamHI, StuI, XbaI, HindIII 3'

10.2. Introduction of the PTP-S31D Coding Region into nGEX-αK2

The plasmid pSP-S31D (Section 9) was digested with BamHI and EcoRV and inserted in the pcDNA I vector (Invitrogen) which was digested with the same enzymes. The resulting plasmid, pc-S31D, was in turn digested with BspHI and XbaI, giving rise to a fragment of about 1500 bp. The PTP-S31D fragment was subsequently ligated into the pGEX-αK2 (cut with NcoI and XbaI). The resulting plasmid was termed p16 (pGEX-αK2/PTP-S31D) and used in the expression studies described below. p16 encodes a fusion protein of glutathione-S-transferase and PTP-S31D (starting with the first methionine) and contains further about 500 bp of the 3' untranslated region of PTP-S31C (and PTP-S31D).

An identical strategy was used to introduce the PTP-S31C into pGEX-αK2, except that pSP-S31C was used to produce the pcDNA I based plasmid: pc-S31C. The resulting plasmid was termed p17 (pGEX-αK2/PTP-S31C).

10.3. Expression of GST-PTP S31 Fusion Protein in *E. Coli*

The pGEX-αK2/PTP-S31D vector construct, p16, and the PGEX-αK2/PTP-S31C vector construct, p17, which encode fusion proteins of glutathione S-transferase (GST) and PTP-S31D or PTP-S31C, respectively (Smith et al., *Proc. Natl. Acad. Sci. USA* 83:87–3–8707 (1988)) were introduced into the *E. coli*, strain DH5α (Cat. No. 8263SA, Bethesda Research Laboratories, Gaithersburg, Md.) and SURE™ (Cat. No. 200294, Stratagene, La Jolla, Calif. 92037).

Overnight cultures of the transformed *E. coli* were grown in LB medium and diluted 1:10 in fresh medium (45 ml overnight culture plus 405 ml LB medium with ampicillin) and grown for 1 hour at 37° C. Isopropyl-1-thio-β-D-galactopyranoside (IPTG) was added to a final concentration of 0.2 mM (DH5α) and 5 mM (SURE) and the cultures were incubated for a further 4 hours. A volume of 400 ml from each culture was centrifuged at 4° C. for 10 minutes at 5000 rpm in a Sorvall GS3 rotor. The pellets were frozen in liquid nitrogen, then thawed in 3 ml of lysis buffer (0.03 M Tris HCl, pH 8.0, 2.5 mM EDTA, 10 μg/ml aprotinin, 1 mM phenylmethylsulfonyl fluoride (PMSF), 1% (v/v) 2-mercaptoethanol) and sonicated on ice (M.S.E. Ultrasonic Disintegrator—100 W Model (cat. no. 7100): 3 cycles of 30 seconds, maximum setting). After sonication, the lysates were centrifuged and the supernatant filtered through a 0.45 μm filter (Millipore). Controls were: (1) pGEX-αK2 with and without IPTG; and (2) p16 and p17 without addition of IPTG. The GST-PTP-S31D and GST-PTP-S31C fusion proteins as well as GST were isolated as soluble proteins by glutathione-Sepharose 4B affinity chromatography (Cat. No. 17-0756-01, Pharmacia, Uppsala, Sweden) according to the manufacturer's instructions using 150 μl glutathione-Sepharose 4B per milliliter of the sonicated and sterile-filtered bacterial lysates and incubating with slow rotation for 1 hour at 4° C. The Sepharose beads were washed 3 times in phosphate buffered saline (PBS) and finally resuspended in 250 μl lysis buffer (see above). Expression of the GST/PTP-S31D and GST/PTP-S31C fusion proteins, respectively, as well as the glutathione-S-transferase was verified by sodium dodecylsulfate (SDS) polyacrylamide gel electrophoresis (PAGE) using standard techniques (Ausubel et al., supra). Various amounts of the suspension of glutathione-Sepharose beads with GST-PTP-S31D, GST-PTP-S31C, and GST (control) were analyzed for enzymatic activity as described below.

10.4. Analysis of Enzymatic Activity of the GST-PTP-S31D Fusion Protein

The activity of PTP-S31D towards the substrate p-nitrophenyl phosphate (pNP-P) was measured essentially as described by Tonks et al., *J. Biol. Chem.* 263:6731–6737 (1988)). Increasing amounts of the glutathione-Sepharose beads with GST/PTP-S31D, GST/PTP-S31C and GST, respectively, from above were incubated with 25 mM pNP-P at room temperature in a reaction mixture containing 50 mM 2-(N-morpholino) ethane sulfonic acid (MES) pH 5.5, 10 mM dithiothreitol, and 5 mM ethylenediamine tetraacetic acid (EDTA). The reaction was stopped by addition of equal volumes of 0.4 M NaOH. After centrifugation, the supernatants were transferred to microtiter plates and the absorbance at 405 nm was read with a Dynatech MR5000 reader.

In this phosphatase assay only the GST/PTP-S31D fusion protein showed activity (FIG. 8).

11. EXAMPLE

Northern Blot Analysis of PTP-S31

Total RNA was isolated from several human tissues (spleen, placenta, lung, kidney, colon, liver and from two sources of normal skeletal muscle as well as diabetic skeletal muscle) and cell lines (KG1 (ATCC CCL 246); MOLT-4 (ATCC CRL 1582); Raji (ATCC CCL86); K-562 (ATCC CCL 243); NEG01; Hep G2 (HB 8065); Ea.hy (obtained from Dr. Cora-Jean S. Edgell, University of North Carolina, Chapel Hill, N.C.); A673 ATCC CRL 1598); and RD (ATCC CCL 136)) by the acid guanidium thiocyanate-phenol-chloroform extraction procedure as described by Puissant et al., *BioTechniques* 8:148–149 (1990)).

Poly(A)$^+$ RNA was isolated on an oligo(dT) column (Aviv et al., *Proc. Natl. Acad. Sci. USA* 69:1408–1412 (1972)). Two μg poly(A)$^+$ RNA were loaded in the lanes, separated in an agarose-formaldehyde gel and blotted onto nylon filters (Stratagene, La Jolla) using standard techniques (Ausubel et al., supra). The filters were hybridized with the PTP-S31 PCR fragment (described in Section 6) labeled with [$\alpha^{32}$ P]dATP. The $^{32}$P-labeling was done with the Random Primers DNA Labeling System (Cat. no. 8187SA, Bethesda Research Laboratories, Gaithersburg, Md. 20877, USA) according to the manufacturer's instructions. Subsequently, the filters were washed under stringent conditions and applied to X-ray films.

Analysis of the Northern blots showed a broad range of transcripts of PTP-S31 (from about 2.1 to 2.8 kb) in one of the sources of skeletal muscle poly(A)$^+$ RNA, whereas the expression was barely detectable in the other sample of normal skeletal muscle. The broad band in this Northern blot might indicate the existence of several forms of mRNA (e.g., alternative splicing) derived from the same gene. Expression of PTP-S31 was also demonstrated in skeletal muscle of a patient with type II diabetes.

Surprisingly, the size of the major transcript in the RD cell line is about 4.4 kb. Additionally, a relatively broad but weaker band (2.1–2.4 kb), as well as a weak band of around 6 kb, are found in the RD cell line. A long exposure of the Northern blot with skeletal muscle RNA shows that there is a minor transcript of about 4.4 kb, as in the RD cell line. In lung tissue, a weak signal is found at about 8 kb. Using Northern blotting, none of the other tissues or cell lines showed measurable expression levels of PTP-S31. However, with the sensitive PCR technique, PTP-S31 was found to be expressed in the following tissues and cell lines: liver (pregnancy); placenta; skeletal muscle; kidney; peripheral blood lymphocytes; HepG2 cells (ATCC CCL 86) (almost exclusively in the PTP S31C form), RD cells (ATCC CCL 136); A673 cells (ATCC CRL 1598); IM9 cells (ATCC CCL 159); CEM cells (ATCC CCL 119); U937 cells (ATCC CRL 1593); A549 cells (ATCC CCL 185); and KLE cells (ATCC CRL 1622).

12. EXAMPLE

Cloning of Additional Subtypes of PTP-S31

Due to the observed size difference between the major transcripts of PTP-S31 in the RD cell line and skeletal muscle, further experiments were conducted involving cDNA cloning of PTP-S31 from the two sources of normal skeletal muscle showing low and high expression levels, respectively (based on the northern blot analysis described in Section 11).

Poly (A)+ RNA was isolated from the two sources of normal human skeletal muscle as described in Section 11, above. Using 5 µg of these poly (A)+ RNA preparations, two λ ZAP II cDNA libraries were prepared according to the manufacturer's instructions (Stratagene, La Jolla, Calif.). The library constructed from the RNA with low expression levels of PTP-S31 was termed library #2. The library constructed from RNA with high expression levels of PTP-S31 was termed library #3. A total of 2×10⁶ plaques were screened from each library using standard filter hybridization techniques (Ausubel et al., supra). Duplicate Hybond N+ (Amersham) filters were hybridized with the same ³²P-labeled PCR fragment as that used in Section 11, above.

The ³²P-labeling was done with the Random Primers DNA Labeling System (Cat. no. 8187SA, Bethesda Research Laboratories, Gaithersburg, Md. 20877, USA) according to the manufacturer's instructions. The filters were washed at high stringency (0.1×SSC, 0.05% SDS). Subsequently, the filters Were applied to X-ray films.

Three positive clones were identified from library #2, isolated, subjected to in vivo excision according to the manufacturer s instructions and analyzed by sequencing. From library #3 a total of nine positive clones were isolated and analyzed.

Figure 10:
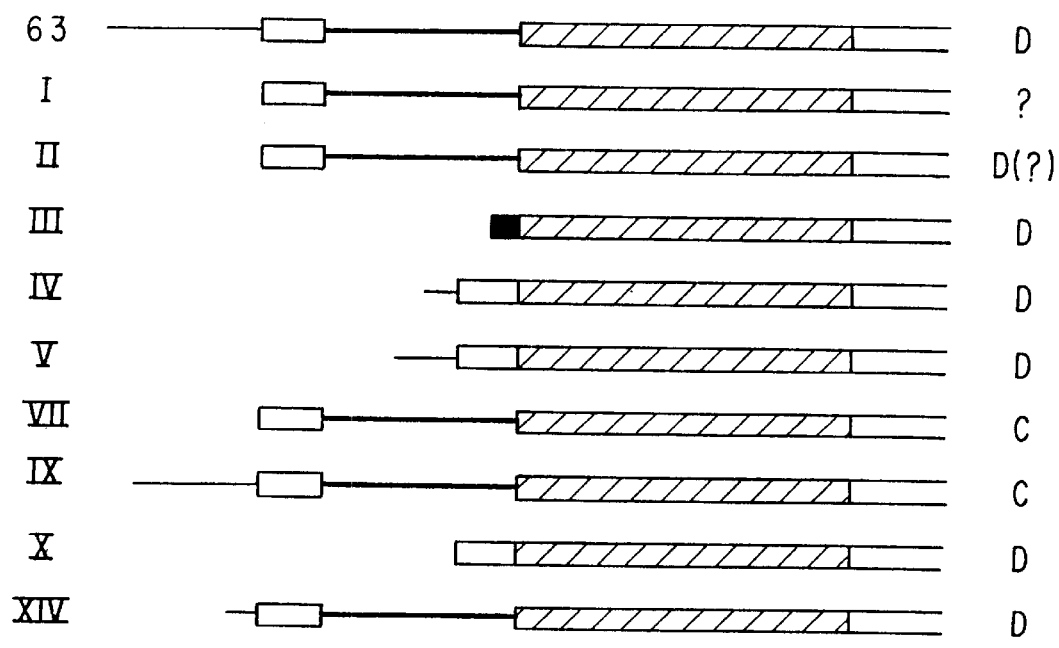

The longest clone (S31D-63) was isolated from cDNA library #2; its nucleotide sequence and predicted amino acid sequence is shown in FIGS. 9A–9E. Surprisingly, neither this clone nor any of the other clones analyzed contained the 5' end of the PTP-S31C clone (clone 1.20.4) isolated from the RD cDNA library (library #1). Instead, all clones from the skeletal muscle cDNA libraries contained 5' ends which are not similar to any known sequence. None of the clones appeared to be full-length since there was no in-frame ATG triplet upstream from the nucleotide where these clones differ from clone 1.20.4. The various forms identified are schematically shown in FIG. 10.

Isolation of additional, partial clones from library #3 showed further variants of PTP-S31 which most likely resulted from alternative splicing. The deduced amino acid sequences of these variants are shown in FIG. 11.

A new cDNA library (library #14.) was constructed from poly(A)+ RNA from the RD cell line using the λ ZAP II cDNA cloning procedure (Stratagene, La Jolla, Calif.) as described above. A total of 1×10⁶ plaques were screened using standard filter hybridization techniques (Ausubel et al., supra). Duplicate Hybond N (Amersham) filters were hybridized with the same 32P-labeled PCR fragment as that used in Section 11, above. The 32P labeling was done with the Random Primers DNA Labeling System (Cat. No. 8187SA, Bethesda Research Laboratories, Gaithersburg, Md.) according to the manufacturer's instructions. The filters were washed at high stringency (0.1×SSC, 0.05% SDS) and subsequently applied to X-ray films. From library #14, a total of 7 positive clones were isolated, subjected to in vivo excision according to manufacturer's instructions and analyzed.

Two of the clones from library #14 are identical to clone 1.20.4, except that they are a few bases shorter at the 5' end (i.e., both are PTP-S31C). Five clones were found to be similar to clone S31D-63 from above, but they differed at the 5' ends. The longest two of these clones were characterized by sequencing. Clone S31-RD#2 corresponds to the D form of PTP S31, whereas clone S31-RD#6, which is about 250 base pairs shorter than clone S31-RD#2 at the 5' end, corresponds to the C form. Otherwise both clones are identical. Partial nucleotide (SEQ ID NO:21) and predicted amino acid sequences (SEQ ID NO:22) of PTP-S31 RD#2 are shown in FIGS. 12A–12D. Surprisingly, this form of PTP-S31 contained a transmembrane domain. Therefore, PTP-S31 may exist both as an intracellular and as a receptor-type PTP.

It is noteworthy that, until now, only one mammalian transmembrane PTP, RPTPβ, has been found to contain a single PTPase domain (Krueger et al., supra). Like RPTP#, PTPS31-RD#2 has only one PTPase domain.

Furthermore, the amino acid sequence of PTPS31-RD#2 adjacent to the putative transmembrane region shares similarity with the interleukin 2 receptor β chain and other cytokine receptors (Miyajama et al., *Annu. Rev. Immunol.* 10:295–3331 (1992). This region also shares some homology with fibronectin type III (FN-III) domains (Patthy, L., *Cell* 61:13–14 (1990)).

Some of the structural features common to fibronectin type III-like domains can be seen in the extracellular domain of PTPS31-RD#2. In the amino acid sequence [SEQ ID NO:22) presented in FIGS. 12A–12D, a total of four FN-III like domains can be identified (see FIG. 14). The domains are designated S31-FN-1 (the most C-terminal and therefore adjacent to the transmembrane region) to S31-FN-4 (the most N-terminal). These FN-III like domains contain a relatively high number of cysteine residues. This is in contrast to the FN-III-like domains of LAR (Streuli et al., supra) and cytokipe receptors (Patthy, supra). Also, an otherwise highly conserved tryptophan residue is replaced in S31-FN-2 with a phenylalanine residue. Further, the demarcations between individual FN-III domains are not nearly as well-conserved as in RPTPβ.

There are several potential sites for N-linked glycosylation in the extracellular domain of PTP-S31.

Surprisingly, a stretch of about 100 amino acids or PTPS31-RD#2 shows a relatively high sequence similarity to a portion of the a subunit of the insulin receptor (FIG. 15). The similarity of PTPS31-RD#2 to the insulin receptor as well as to cytokihe receptors indicates that the transmembrane form of PTP-S31 may be regulated by hormones or cytokines. Alternatively, the FN-III-like domains may indicate that PTP-S31 is involved in cell-cell interactions.

13. EXAMPLE

Detection and Measurement of PTP-S31 Protein in a Cell 13.1. Production of Antibodies with Specificity for PTP-S31D Antiserum with specificity for PTP-S31D was produced by standard techniques (Hudson, L. et al., *Practical Immunology*, 3rd Edition, Blackwell, Oxford, 1989). In brief, 200 μg of the GST-PTP S31D fusion protein (see Section 10) in 200 μl phosphate buffered saline were combined with an equal volume of Freund's complete adjuvant (Sigma, Cat. No. F5881) and injected intracutaneously into two New Zealand rabbits. Each rabbit received 100 μg of the fusion protein. Two weeks after the first injection, booster injections without Freund's adjuvant were administered. After 2 more weeks, 20 ml of blood were obtained from each rabbit and allowed to clot at room temperature for 1 hour in glass tubes. The clots were centrifuged after loosening from the tube, and aliquots of the serum were transferred to fresh tubes and stored at −20° C. until use.

To remove the antibodies which are specific for glutathione S-transferase (GST), the serum was passed over a glutathione-Sepharose 4B column which has been saturated with glutathione S-transferase using the procedure described in Section 10. The pGEX-αK2 construct was used to produce the GST protein. The serum was passed over the column three times to ensure complete removal of the anti-GST antibodies. The efficiency of the removal was assessed by Western blotting as described below.

13.2. Detection and Measurement of PTP-S31D in a Cell Line

The anti-PTP-S31D antibody can be used to detect the expression of PTP-S31 in mammalian cells. Standard immunofluorescence techniques provide information about expression of this protein in specific cell lines and tissues. Even more importantly, this antibody preparation can be used to determine the quantity of the protein in cell lines and tissues. As an example of the latter application of the anti-PTP S31 antibody, the detection of PTP-S31 in the RD cell line (ATCC CCL 136) is described below. It should be emphasized that this Example is not in any way intended to be limiting as to the use of the antibody, which can be used for detection of PTP-S31 in other cells and tissues as well. Likewise, the antibody preparation can be useful in purification of naturally occurring or recombinant PTP S31 and for establishing other types of detection assays.

Using standard techniques, the RD cell line is cultured in Eagle's minimal essential medium (Cat. No. 041-022570, GIBCO Life Technologies Ltd., Paisley, Scotland) with twice the normal concentrations of amino acids and vitamins with Hanks' balanced salt solution and 10% fetal calf serum (FCS) (GIBCO-BRL).

The cells are washed twice in phosphate buffered saline (PBS) and the supernatant removed. The cells from one tissue culture plate (10 cm diameter) are lysed in 800 Al of a Triton X-100 lysis buffer (20 mM HEPES pH 7.5, 50 mM NaCl, 10% glycerol, 1.0% Triton X-100, 1.5 mM $MgCl_2$, 4 mM ethylene glycol-bis(β-aminoethylethyl ether) N,N,N',N'-tetraacetate (EGTA; Sigma ED2SS), 10 μg/ml aprotinin, 1 mM phenylmethylsulfonyl fluoride (PMSF)). The lysate is centrifuged and the supernatant transferred to fresh tubes in aliquots for storage at −80° C. until use.

For testing, 1–50 μl of this lysate is mixed with 25 μl SDS sample buffer (62.5 mM Tris HCl, pH 7.0, 3.0% (v/v) SDS, 10% (v/v) glycerol, 10% 2-mercaptoethanol, and 0.05% (w/v) bromophenol blue), boiled for 5 minutes, separated by 7.5% SDS-polyacrylamide gel electrophoresis and blotted onto nitrocellulose using standard techniques (Burnette, W. N., *Anal. Biochem.* 112:195–201 (1981)).

A standard curve for the quantitative determination of PTP-S31D is generated by using defined amounts of purified *E. coli*-produced GST-PTP-S31D fusion protein from above in parallel with the RD cell lysates.

The nitrocellulose filters are incubated for 30 minutes with 2 grams milk powder (Carnation, Non-Fat Dry Milk, Carnation, Los Angeles, Calif.) per liter PBS to block nonspecific binding, washed once in PBS containing 0.02% (v/v) Tween-20 (Sigma, P1379) (PBS-Tween) and 0.2% (w/v) gelatin (BioRad Cat. No. 170-6537, Richmond, Calif.), washed 3 times in PBS-Tween and finally incubated for 4 hr with a 1:200 dilution (in PBS-Tween) of the anti-PTP-S31D antiserum preparation described above. After three washings in PBS-Tween, the filters are incubated with horseradish peroxidase-conjugated goat anti-rabbit IgG (Cat. No. 170-6525, BioRad). The filters are washed three times in PBS-Tween and the amount of rabbit antibody bound, which indicates the amount of PTP-S31D, is determined by the enhanced chemiluminescence (ECL) technique according to the manufacturer's instructions (Cat. No. RPN 2106, Amersham, UK). Comparison of the signals obtained from the RD cell line with the standard curve obtained with the E. coli-produced GST-PTP S31D fusion protein allows determination of the amount of PTP-S31D produced by the RD cell line.

14. EXAMPLE

Identification of an Agent that Stimulates or Inhibits Enzymatic Activity of PTP-S31

Two different sources of PTP-S31 protein are used for the evaluation of potential modulators of the enzymatic activity:
1. The GST-PTP-S31D (and C) fusion proteins as described in Section 10;
2. PTP-S31 transiently expressed in 293 cells as described below.

The cDNA containing the entire coding region of PTP-S31 (C or D) or a functional portion thereof, is inserted into the mammalian expression vector pcDNA I (Cat. No. V490-20, Invitrogen, San Diego) using standard techniques (Ausubel et al., supra). The 293 cell transient expression system described by Gorman et al., *Virology* 171:377–385 (1989) is used to produce enzymatically active PTP-S31D. Using standard techniques, the 293 cells are cultured in Dulbecco s Modified Eagle Medium (Cat. No. a041-02430, GIBCO, Life Technologies Ltd., Paisley, Scotland) supplemented with 10% FCS in an atmosphere of 5% $CO_2$ at 37° C.

Ten μg of the plasmid construct PTP-S31D/pcDNA I (or PTP-S31C/pcDNA I) are mixed with 0.5 ml 0.25M $CaCl_2$ and 0.5 ml 2×BBS (50 mM N,N-bis(2-hydroxyethyl)-2-aminoethane-sulfonic acid (BES), 280 mM NaCl, 1.5 mM $Na_2HPO_4$) and used for transfection of $1.5 \times 10^6$ 293 cells in a 10 cm Petri dish as described by Chen et al., *Mol. Cell. Biol.* 7:2745–2752 (1987). The cells are incubated 24 hr at 37° C. under 3% $CO_2$ after the addition of the Ca-phosphate-DNA precipitate, then washed once in DMEM supplemented with 10% FCS and incubated in fresh medium for additional 24 hours at 37° C. under.5% $CO_2$. The medium is removed and the cells lysed in 1.0 ml of lysis buffer (20 mM HEPES, pH 7.5, 150 mM NaCl, 10% glycerol, 1.0% Triton X-100, 1.5 mM $MgCl_2$, 4 mM EGTA, 10 μg/ml aprotinin, 1 mM PMSF). The cell lysates are centrifuged at 2500×g for 2 minutes at 4° C. The supernatant is removed and 100 μl aliquots are quick-frozen in liquid nitrogen and stored at −70° C. until use.

The PTP-S31 in the lysate may be partially purified using conventional chromatographic techniques such as anion exchange chromatography and gel filtrations.

Three different substrates are used for the evaluation of potential modulators of the PTP-S31 phosphatase activity:
(1) p-nitrophenyl phosphate (pNP-P; Sigma 104-0);
(2) $^{32}$P-labeled Raytide (Oncogene Science Inc., Manhasset, N.Y.);

(3) $^{32}$P-labeled bovine myelin basic protein (MBP).

Substances which either decrease or increase the activity of PTP-S31 against one or more of these substrates are analyzed further.

14.1. Labeling of Raytide and Myelin Basic Protein with $^{32}$P

The activity towards $^{32}$P-labeled Raytide™ of the GST/PTP-S31D (and C) fusion proteins (Section 10) as well as of the complete and preferably, semipurified, PTP-S31D protein or glycoprotein, or a functional part thereof expressed in 293 cells, is measured essentially as described by Krueger et al. (*EMBO J.* 9:3241–3252 (1990)). The synthetic peptide Raytide is labeled with $^{32}$P using the tyrosine kinase p60$^{c-arc}$ according to the manufacturer's instructions (Oncogene Science) with minor modifications. In brief, 2 µl of p60$^{c-arc}$ are mixed with 20 µl Raytide (1 mg/ml) and 108 µl of kinase buffer (50 mM HEPES, pH 7.5 containing 10 mM MgCl$_2$, 0.2% (v/v) β-mercaptoethanol, 30 µM ATP and 50 µCi [γ-$^{32}$P]ATP). The mixture is incubated at 37° C. for 16 hours, and the reaction is stopped by addition of 500 µl of 20% (w/v) trichloroacetic acid (TCA) in 20 mM NaH$_2$PO$_4$ and 100 µl of 5 mg/ml of acetylated bovine serum albumin. The mixture is centrifuged, the precipitate is washed three times in 20% TCA/20 mM NaH$_2$PO$_4$ and is finally redissolved in 0.2 M Tris-HCl pH 8.0.

Myelin basic protein (Sigma) is labeled using a procedure similar to that used for Raytide (Guan et al., *Nature* 350:359–362 (1991)). Thirty µg of MBP is labeled in a 60 µl reaction volume containing the following components: 50 mM HEPES buffer, pH 7.5, 10 mM MgCl$_2$, 0.067% β-mercaptoethanol, 0.05 mM ATP including 150 µCi (γ-$^{32}$P) ATP and 4 Units p43$^{v-abl}$ kinase (oncogene Science). The mixture is incubated for 60 minutes at 30° C., and the reaction is stopped by addition of ice-cold TCA to a final concentration of 20%. After 30 minutes on ice, the precipitate is washed three times in 20% TCA and redissolved in 100 µl H$_2$O.

14.2. Assessment of PTP Activity Using the Substrate pNP-P

The activity of the GST/PTP-S31D fusion protein towards pNP-P is measured as described in Section 10, above. The substances to be analyzed for their ability to stimulate or inhibit phosphatase activity are added to the GST/PTP-S31D fusion protein 5 minutes prior to the addition of pNP-P. A similar procedure is used for PTP-S31D expressed in 293 cells, where the PTP-S31D/293 cell lysate is used directly.

Table I, below, shows the effect of several agents on PTP activity of the GST/PTP-S31 fusion protein bound to glutathione-Sepharose beads as described in Section 10. The indicated concentrations of the agents are the final concentrations in the reaction mixture after addition of the substrate, pNP-P. The phosphatase assay mixture contained 50 mM 2-(N-Morpholino)ethane sulfonic acid (MES) pH 5.5, 10 mM dithiothreitol, 25 mM pNP-P and 2 µl of the GST/PTP-S31-Sepharose suspension. When testing orthovanadate, poly(Glu/Tyr) 4:1 and poly-L-lysine, 5 mM EDTA was included in the assay mixture. The reaction was carried out at room temperature and stopped after 30 minutes by addition of equal volumes of 0.4M NaOH. After centrifugation, the supernatants were transferred to microtiter plates and the absorbance at 405 nm read with a Dynatech MR5000 plate reader. For comparison, Table I includes published data of the activity of PTPB and LAR using Raytide as a substrate (Itoh et al (*J. Biol. Chem.* 267: 12356–12363 (1992)).

TABLE I

EFFECTS OF VARIOUS AGENTS ON PTP ACTIVITY

| Agent | Conc (mM) | PTP Activity (% of control) | | |
|---|---|---|---|---|
| | | S31D | PTPβ | LAR |
| MgCl$_2$ | 1 | 123 | 90 | 119 |
| | 10 | 140 | 141 | 56 |
| MnCl$_2$ | 1 | 110 | 85 | 72 |
| | 10 | 140 | 64 | 30 |
| ZnCl$_2$ | 0.1 | 68 | 18 | 90 |
| | 1 | 13 | 3 | 120 |
| | 10 | 9 | 0 | 6 |
| Ortho-vanadate | 0.1 | 64 | 33 | 59 |
| | 1 | 23 | 6 | 25 |
| | (µg/ml) | | | |
| Poly (Glu/Tyr) | 1 | 84 | 97 | 103 |
| | 10 | 85 | 85 | 97 |
| | 100 | 77 | 61 | 96 |
| Poly-L-Lysine | 1 | 156 | 239 | 123 |
| | 10 | 172 | 653 | 230 |
| | 100 | 192 | 125 | 247 |

It should be emphasized that the above Example is not intended in any way limit the scope of the invention.

14.3. Assessment of PTP Activity Using the Substrates Raytide or MBP

Five µl 10×PTP buffer (250 mM-HEPES, pH 7.3, 50 mM EDTA, 100 mM dithiothreitol) are mixed with (a) 5 µl $^{32}$P-labeled Raytide or MBP (corresponding to 10–20×10$^4$ cpm), b) 5, 10 and 25 µl, respectively, of the PTP-S31D/293 cell lysate, or 0.5, 1 and 5 µl of the suspension of the GST-PTPS31D fusion protein bound to glutathione-Sepharose beads (see Section 10) and (c) H$_2$O to a final volume of 50 µl. The reaction is stopped after 30 minutes at 37° C. When using Raytide, the reaction is stopped by addition of 0.75 ml acidic charcoal mixture (Krueger et al., *EMBO J.* 9:3241–3252 (1990)): 0.9M HCl, 90 mM sodium pyrophosphate, 2 mM NaH$_2$PO$_4$, 4% (v/v) Norit A (Sigma)). After mixing and centrifugation, 400 µl of the supernatant are removed and the amount of radioactivity measured. When using MBP, the reaction is stopped with 20% TCA (final volume). The amount of $^{32}$P in the supernatant is then measured.

The substances to be analyzed for modulatory activities are added to the PTP-S31/293 cell lysate 5 minutes prior to initiation of the assays.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

SEQUENCE LISTING

<160> NUMBER OF SEQ ID NOS: 53

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (3)..(4)
<223> OTHER INFORMATION: Variable amino acid

<400> SEQUENCE: 1

Lys Cys Xaa Xaa Tyr Trp Pro
 1               5

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (4)
<223> OTHER INFORMATION: Variable amino acid
<221> NAME/KEY: MOD_RES
<222> LOCATION: (6)
<223> OTHER INFORMATION: Variable amino acid
<221> NAME/KEY: MOD_RES
<222> LOCATION: (9)
<223> OTHER INFORMATION: Variable amino acid

<400> SEQUENCE: 2

His Cys Ser Xaa Gly Xaa Gly Arg Xaa Gly
 1               5                  10

<210> SEQ ID NO 3
<211> LENGTH: 321
<212> TYPE: DNA
<213> ORGANISM: Artificial Sequence
<220> FEATURE:
<223> OTHER INFORMATION: Description of Artificial Sequence: PTP-S31
<221> NAME/KEY: CDS
<222> LOCATION: (1)..(321)

<400> SEQUENCE: 3 gaa acc aga gca aaa aca tta gta atg cta aca cag tgt ttt gaa aaa        48
Glu Thr Arg Ala Lys Thr Leu Val Met Leu Thr Gln Cys Phe Glu Lys
 1               5                  10                  15 gga cgg atc aga tgc cat cag tat tgg cca gag gac aac aag cca gtt        96
Gly Arg Ile Arg Cys His Gln Tyr Trp Pro Glu Asp Asn Lys Pro Val
                20                  25                  30 act gtc ttt gga gat ata gtg att aca aag cta atg gag gat gtt caa       144
Thr Val Phe Gly Asp Ile Val Ile Thr Lys Leu Met Glu Asp Val Gln
            35                  40                  45 ata gat tgg act atc agg gat ctg aaa att gaa agg cat ggg gat tgc       192
Ile Asp Trp Thr Ile Arg Asp Leu Lys Ile Glu Arg His Gly Asp Cys
        50                  55                  60 atg act gtt cga cag tgt aac ttt act gcc tgg cca gag cat ggg gtt       240
Met Thr Val Arg Gln Cys Asn Phe Thr Ala Trp Pro Glu His Gly Val
 65                  70                  75                  80 cct gag aac agc gcc cct cta att cac ttt gtg aag ttg gtt cga gca       288
Pro Glu Asn Ser Ala Pro Leu Ile His Phe Val Lys Leu Val Arg Ala
                 85                  90                  95

```
agc agg gca cat gac acc aca cct atg att gtt                    321
Ser Arg Ala His Asp Thr Thr Pro Met Ile Val
        100                 105
```

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: PTP-S31

<400> SEQUENCE: 4

```
Glu Thr Arg Ala Lys Thr Leu Val Met Leu Thr Gln Cys Phe Glu Lys
 1               5                  10                  15

Gly Arg Ile Arg Cys His Gln Tyr Trp Pro Glu Asp Asn Lys Pro Val
            20                  25                  30

Thr Val Phe Gly Asp Ile Val Ile Thr Lys Leu Met Glu Asp Val Gln
        35                  40                  45

Ile Asp Trp Thr Ile Arg Asp Leu Lys Ile Glu Arg His Gly Asp Cys
    50                  55                  60

Met Thr Val Arg Gln Cys Asn Phe Thr Ala Trp Pro Glu His Gly Val
 65                  70                  75                  80

Pro Glu Asn Ser Ala Pro Leu Ile His Phe Val Lys Leu Val Arg Ala
                85                  90                  95

Ser Arg Ala His Asp Thr Thr Pro Met Ile Val
            100                 105
```

<210> SEQ ID NO 5
<211> LENGTH: 385
<212> TYPE: PRT
<213> ORGANISM: Artificial Sequence
<220> FEATURE:
<223> OTHER INFORMATION: Description of Artificial Sequence: PTP 1B

<400> SEQUENCE: 5

```
Met Glu Met Glu Lys Glu Phe Glu Gln Ile Asp Lys Ser Gly Ser Trp
 1               5                  10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
 65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175
```

```
Thr Thr Trp Pro Asp Phe Gly Val Pro Glu Ser Pro Ala Ser Phe Leu
        180                 185                 190
Asn Phe Leu Phe Lys Val Arg Glu Ser Gly Ser Leu Ser Pro Glu His
        195                 200                 205
Gly Pro Val Val His Cys Ser Ala Gly Ile Gly Arg Ser Gly Thr
        210                 215                 220
Phe Cys Leu Ala Asp Thr Cys Leu Leu Leu Met Asp Lys Arg Lys Asp
225                 230                 235                 240
Pro Ser Ser Val Asp Ile Lys Lys Val Leu Leu Glu Met Arg Lys Phe
                245                 250                 255
Arg Met Gly Leu Ile Gln Thr Ala Asp Gln Leu Arg Phe Ser Tyr Leu
                260                 265                 270
Ala Val Ile Glu Gly Ala Lys Phe Ile Met Gly Asp Ser Ser Val Gln
            275                 280                 285
Asp Gln Trp Lys Glu Leu Ser His Glu Asp Leu Glu Pro Pro Pro Glu
        290                 295                 300
His Ile Pro Pro Pro Arg Pro Pro Lys Arg Ile Leu Glu Pro His
305                 310                 315                 320
Asn Gly Lys Cys Arg Glu Phe Phe Pro Asn His Gln Trp Val Lys Glu
                325                 330                 335
Glu Thr Gln Glu Asp Lys Asp Cys Pro Ile Lys Glu Glu Lys Gly Ser
            340                 345                 350
Pro Leu Asn Ala Ala Pro Tyr Gly Ile Glu Ser Met Ser Gln Asp Thr
        355                 360                 365
Glu Val Arg Ser Arg Val Val Gly Gly Ser Leu Arg Gly Ala Gln Ala
        370                 375                 380
Ala
385

<210> SEQ ID NO 6
<211> LENGTH: 2173
<212> TYPE: DNA
<213> ORGANISM: Artificial Sequence
<220> FEATURE:
<223> OTHER INFORMATION: Description of Artificial Sequence: PTP-S31C
<221> NAME/KEY: modified_base
<222> LOCATION: (1)..(1630)
<223> OTHER INFORMATION: n = unknown nucleotide
<221> NAME/KEY: CDS
<222> LOCATION: (65)..(1066)

<400> SEQUENCE: 6
tattttagct tgggaagtaa tacggggata tttaaactcc ttggggtttg aaaaccatgt    60 catt atg aga atg agg cca ata agc aag aaa tcc ttc ctg caa cat gtt   109
     Met Arg Met Arg Pro Ile Ser Lys Lys Ser Phe Leu Gln His Val
     1               5                   10                  15 gaa gag ctt tgc aca aac aac aac cta aag ttt caa gaa gaa ttt tcg   157
Glu Glu Leu Cys Thr Asn Asn Asn Leu Lys Phe Gln Glu Glu Phe Ser
                20                  25                  30 gaa tta cca aaa ttt ctt cag gat ctt tct tca act gat gct gat ctg   205
Glu Leu Pro Lys Phe Leu Gln Asp Leu Ser Ser Thr Asp Ala Asp Leu
            35                  40                  45 cct tgg aat aga gca aaa aac cgc ttc cca aac ata aaa cca tat aat   253
Pro Trp Asn Arg Ala Lys Asn Arg Phe Pro Asn Ile Lys Pro Tyr Asn
        50                  55                  60 aat aac aga gta aag ctg ata gct gac gct agt gtt cca ggt tcg gat   301
Asn Asn Arg Val Lys Leu Ile Ala Asp Ala Ser Val Pro Gly Ser Asp
    65                  70                  75
```

-continued

| | |
|---|---|
| tat att aat gcc agc tat att tct ggt tat tta tgt cca aat gaa ttt<br>Tyr Ile Asn Ala Ser Tyr Ile Ser Gly Tyr Leu Cys Pro Asn Glu Phe<br>80                        85                     90                    95 | 349 |
| att gct act caa ggt cca cta cca gga aca gtt gga gat ttt tgg aga<br>Ile Ala Thr Gln Gly Pro Leu Pro Gly Thr Val Gly Asp Phe Trp Arg<br>100                       105                   110 | 397 |
| atg gtg tgg gaa acc aga gca aaa aca tta gta atg cta aca cag tgt<br>Met Val Trp Glu Thr Arg Ala Lys Thr Leu Val Met Leu Thr Gln Cys<br>115                    120                   125 | 445 |
| ttt gaa aaa gga cgg atc aga tgc cat cag tat tgg cca gag gac aac<br>Phe Glu Lys Gly Arg Ile Arg Cys His Gln Tyr Trp Pro Glu Asp Asn<br>130                   135                   140 | 493 |
| aag cca gtt act gtc ttt gga gat ata gtg att aca aag cta atg gag<br>Lys Pro Val Thr Val Phe Gly Asp Ile Val Ile Thr Lys Leu Met Glu<br>145                    150                   155 | 541 |
| gat gtt caa ata gat tgg act atc agg gat ctg aaa att gaa agg cat<br>Asp Val Gln Ile Asp Trp Thr Ile Arg Asp Leu Lys Ile Glu Arg His<br>160                   165                 170               175 | 589 |
| ggg gat tgc atg act gtt cga cag tgt aac ttt act gcc tgg cca gag<br>Gly Asp Cys Met Thr Val Arg Gln Cys Asn Phe Thr Ala Trp Pro Glu<br>180                   185                   190 | 637 |
| cat ggg gtt cct gag aac agc gcc cct cta att cac ttt gtg aag ttg<br>His Gly Val Pro Glu Asn Ser Ala Pro Leu Ile His Phe Val Lys Leu<br>195                    200                   205 | 685 |
| gtt cga gca agc agg gca cat gac acc aca cct atg att gtt cac tgc<br>Val Arg Ala Ser Arg Ala His Asp Thr Thr Pro Met Ile Val His Cys<br>210                   215                   220 | 733 |
| agg cac agt ata tct ttt tac acc agt gca ttc tgg atc tct tat caa<br>Arg His Ser Ile Ser Phe Tyr Thr Ser Ala Phe Trp Ile Ser Tyr Gln<br>225                    230                   235 | 781 |
| ata agg gaa gta atc agc cca tct gtt ttg tta act att cag cac ttc<br>Ile Arg Glu Val Ile Ser Pro Ser Val Leu Leu Thr Ile Gln His Phe<br>240                   245                 250               255 | 829 |
| aga aga tgg act ctt tgg acg cca tgg aag gtg atg ttg agc ttg aat<br>Arg Arg Trp Thr Leu Trp Thr Pro Trp Lys Val Met Leu Ser Leu Asn<br>260                   265                   270 | 877 |
| ggg aag aaa cca cta tgt aaa tat tca gac caa agg ata caa ttg gaa<br>Gly Lys Lys Pro Leu Cys Lys Tyr Ser Asp Gln Arg Ile Gln Leu Glu<br>275                    280                   285 | 925 |
| gag att ttt aaa tcc cag ggg cca aag tta ccc cct cat tct tcc gaa<br>Glu Ile Phe Lys Ser Gln Gly Pro Lys Leu Pro Pro His Ser Ser Glu<br>290                    295                   300 | 973 |
| ttg aaa tgt gca acc tta aag aaa tat cta tgc ttc tct cac tgt gcc<br>Leu Lys Cys Ala Thr Leu Lys Lys Tyr Leu Cys Phe Ser His Cys Ala<br>305                    310                   315 | 1021 |
| ttt cca aac gga ttg aac att tta aga cta gtt ctt gaa aat agc<br>Phe Pro Asn Gly Leu Asn Ile Leu Arg Leu Val Leu Glu Asn Ser<br>320                   325                   330 | 1066 |
| taatacagaa taattatttg ttttgtacag aataaatatt atgcatttta aatgcttaag | 1126 |
| aaaagacatc ccatatgttt ttgaagtcct ccatattttg gaataagcca aatagaaaat | 1186 |
| tattattata ttagcattaa tgtttcaatg tgaattttcc ctatgtattg gatttaattt | 1246 |
| tgaggacaaa agttgtaaat gttgattcag tagtgttgtt ttggcttaca gggtattgat | 1306 |
| gtttcttgtg gataatttcc aggactgtca taatgatctg tacttccatg tacacccctg | 1366 |
| tgttttgaat cctctgtttt atgagtgctg agatatcatc tcatgatccc gaacagctga | 1426 |
| acagtaaccc cctgacactg cagggattac ttggccttta tacaacacac agtagctctt | 1486 |
| cagggacact tagggctatt taatttcgat tgtgtcttca gtttgagaac cttaaaagaa | 1546 |

-continued

```
aattaaaagt gcaattgcac acatgaaatt acagagtacc attctagcaa acctacattt    1606
gtaaacttta aaacacaagt tttncccct gtattgtata ttcaaatata tagtaaatgt      1666
atcagagtat ttgcccatta gatatgatca acctaatatt aacaattctg aagagtttct    1726
tcagcaaaaa tgtatcaaga gtaataaaaa cactgtgcgt gtttcaagct tgtaaaccaa    1786
tgatctgctg ctgtggtgcc aacagagact tccaaatgga ttatgttaaa tggccgtcat    1846
ttcatttccc aaggttgatt ttgagcagta tacttggtgg aactgaaaac aaagaaatta    1906
accatctata gcaaattcaa ggtttcttta tagaaaatct ttcagcctcc atcttattaa    1966
atagtgacaa tgtggtaagt tttgaattat atgaactcat tttgtcatag atttcaatta    2026
agagtaataa atagtattaa ttatgctctt ctatgataag aagtatatct tatgcttatt    2086
tccgctggaa catatatata tatgaaatgc tatggccaat aaaattgaat tttaatgaaa    2146
aaaaaaaaaa aaaaaaaaa aaaaaaa                                          2173
```

<210> SEQ ID NO 7
<211> LENGTH: 334
<212> TYPE: PRT
<213> ORGANISM: Artificial Sequence
<220> FEATURE:
<223> OTHER INFORMATION: Description of Artificial Sequence: PTP-S31C

<400> SEQUENCE: 7

```
Met Arg Met Arg Pro Ile Ser Lys Lys Ser Phe Leu Gln His Val Glu
  1               5                  10                  15

Glu Leu Cys Thr Asn Asn Leu Lys Phe Gln Glu Glu Phe Ser Glu
             20                  25                  30

Leu Pro Lys Phe Leu Gln Asp Leu Ser Ser Thr Asp Ala Asp Leu Pro
         35                  40                  45

Trp Asn Arg Ala Lys Asn Arg Phe Pro Asn Ile Lys Pro Tyr Asn Asn
     50                  55                  60

Asn Arg Val Lys Leu Ile Ala Asp Ala Ser Val Pro Gly Ser Asp Tyr
 65                  70                  75                  80

Ile Asn Ala Ser Tyr Ile Ser Gly Tyr Leu Cys Pro Asn Glu Phe Ile
                 85                  90                  95

Ala Thr Gln Gly Pro Leu Pro Gly Thr Val Gly Asp Phe Trp Arg Met
            100                 105                 110

Val Trp Glu Thr Arg Ala Lys Thr Leu Val Met Leu Thr Gln Cys Phe
        115                 120                 125

Glu Lys Gly Arg Ile Arg Cys His Gln Tyr Trp Pro Glu Asp Asn Lys
    130                 135                 140

Pro Val Thr Val Phe Gly Asp Ile Val Ile Thr Lys Leu Met Glu Asp
145                 150                 155                 160

Val Gln Ile Asp Trp Thr Ile Arg Asp Leu Lys Ile Glu Arg His Gly
                165                 170                 175

Asp Cys Met Thr Val Arg Gln Cys Asn Phe Thr Ala Trp Pro Glu His
            180                 185                 190

Gly Val Pro Glu Asn Ser Ala Pro Leu Ile His Phe Val Lys Leu Val
        195                 200                 205

Arg Ala Ser Arg Ala His Asp Thr Thr Pro Met Ile Val His Cys Arg
    210                 215                 220

His Ser Ile Ser Phe Tyr Thr Ser Ala Phe Trp Ile Ser Tyr Gln Ile
225                 230                 235                 240

Arg Glu Val Ile Ser Pro Ser Val Leu Leu Thr Ile Gln His Phe Arg
                245                 250                 255
```

```
Arg Trp Thr Leu Trp Thr Pro Trp Lys Val Met Leu Ser Leu Asn Gly
            260                 265                 270

Lys Lys Pro Leu Cys Lys Tyr Ser Asp Gln Arg Ile Gln Leu Glu Glu
        275                 280                 285

Ile Phe Lys Ser Gln Gly Pro Lys Leu Pro Pro His Ser Ser Glu Leu
        290                 295                 300

Lys Cys Ala Thr Leu Lys Lys Tyr Leu Cys Phe Ser His Cys Ala Phe
305                 310                 315                 320

Pro Asn Gly Leu Asn Ile Leu Arg Leu Val Leu Glu Asn Ser
                325                 330

<210> SEQ ID NO 8
<211> LENGTH: 532
<212> TYPE: DNA
<213> ORGANISM: Artificial Sequence
<220> FEATURE:
<223> OTHER INFORMATION: Description of Artificial Sequence: PCR
      fragment
<221> NAME/KEY: CDS
<222> LOCATION: (3)..(530)

<400> SEQUENCE: 8 ac aac aag cca gtt act gtc ttt gga gat ata gtg att aca aag cta        47
   Asn Lys Pro Val Thr Val Phe Gly Asp Ile Val Ile Thr Lys Leu
   1               5                   10                  15 atg gag gat gtt caa ata gat tgg act atc agg gat ctg aaa att gaa       95
Met Glu Asp Val Gln Ile Asp Trp Thr Ile Arg Asp Leu Lys Ile Glu
            20                  25                  30 agg cat ggg gat tgc atg act gtt cga cag tgt aac ttt act gcc tgg      143
Arg His Gly Asp Cys Met Thr Val Arg Gln Cys Asn Phe Thr Ala Trp
        35                  40                  45 cca gag cat ggg gtt cct gag aac agc gcc cct cta att cac ttt gtg      191
Pro Glu His Gly Val Pro Glu Asn Ser Ala Pro Leu Ile His Phe Val
    50                  55                  60 aag ttg gtt cga gca agc agg gca cat gac acc aca cct atg att gtt      239
Lys Leu Val Arg Ala Ser Arg Ala His Asp Thr Thr Pro Met Ile Val
65                  70                  75 cac tgc agt gct gga gtt gga aga act gga gtt ttt att gct ctg gac      287
His Cys Ser Ala Gly Val Gly Arg Thr Gly Val Phe Ile Ala Leu Asp
80                  85                  90                  95 cat tta aca caa cat ata aat gac cat gat ttt gtg gat ata tat gga      335
His Leu Thr Gln His Ile Asn Asp His Asp Phe Val Asp Ile Tyr Gly
                100                 105                 110 cta gta gct gaa ctg aga agt gaa aga atg tgc atg gtg cag aat ctg      383
Leu Val Ala Glu Leu Arg Ser Glu Arg Met Cys Met Val Gln Asn Leu
            115                 120                 125 gca cag tat atc ttt tta cac cag tgc att ctg gat ctc tta tca aat      431
Ala Gln Tyr Ile Phe Leu His Gln Cys Ile Leu Asp Leu Leu Ser Asn
        130                 135                 140 aag gga agt aat cag ccc atc tgt ttt gtt aac tat tca gca ctt cag      479
Lys Gly Ser Asn Gln Pro Ile Cys Phe Val Asn Tyr Ser Ala Leu Gln
145                 150                 155 aag atg gac tct ttg gac gcc atg gaa ggt gat gtt gag ctt gaa tgg      527
Lys Met Asp Ser Leu Asp Ala Met Glu Gly Asp Val Glu Leu Glu Trp
160                 165                 170                 175 gaa ga                                                               532
Glu

<210> SEQ ID NO 9
<211> LENGTH: 176
<212> TYPE: PRT
```

-continued

<213> ORGANISM: Artificial Sequence
<220> FEATURE:
<223> OTHER INFORMATION: Description of Artificial Sequence: amino acid
      sequence encoded by PCR fragment

<400> SEQUENCE: 9

Asn Lys Pro Val Thr Val Phe Gly Asp Ile Val Ile Thr Lys Leu Met
 1               5                  10                  15

Glu Asp Val Gln Ile Asp Trp Thr Ile Arg Asp Leu Lys Ile Glu Arg
                20                  25                  30

His Gly Asp Cys Met Thr Val Arg Gln Cys Asn Phe Thr Ala Trp Pro
            35                  40                  45

Glu His Gly Val Pro Glu Asn Ser Ala Pro Leu Ile His Phe Val Lys
        50                  55                  60

Leu Val Arg Ala Ser Arg Ala His Asp Thr Thr Pro Met Ile Val His
65                  70                  75                  80

Cys Ser Ala Gly Val Gly Arg Thr Gly Val Phe Ile Ala Leu Asp His
                85                  90                  95

Leu Thr Gln His Ile Asn Asp His Asp Phe Val Asp Ile Tyr Gly Leu
                100                 105                 110

Val Ala Glu Leu Arg Ser Glu Arg Met Cys Met Val Gln Asn Leu Ala
            115                 120                 125

Gln Tyr Ile Phe Leu His Gln Cys Ile Leu Asp Leu Leu Ser Asn Lys
    130                 135                 140

Gly Ser Asn Gln Pro Ile Cys Phe Val Asn Tyr Ser Ala Leu Gln Lys
145                 150                 155                 160

Met Asp Ser Leu Asp Ala Met Glu Gly Asp Val Glu Leu Glu Trp Glu
                165                 170                 175

<210> SEQ ID NO 10
<211> LENGTH: 2309
<212> TYPE: DNA
<213> ORGANISM: Artificial Sequence
<220> FEATURE:
<223> OTHER INFORMATION: Description of Artificial Sequence: PTP-S31D
<221> NAME/KEY: modified_base
<222> LOCATION: (1)..(2309)
<223> OTHER INFORMATION: n = unknown nucleotide
<221> NAME/KEY: CDS
<222> LOCATION: (65)..(1030)

<400> SEQUENCE: 10
tattttagct tgggaagtaa tacggggata tttaaactcc ttggggtttg aaaaccatgt        60 catt atg aga atg agg cca ata agc aag aaa tcc ttc ctg caa cat gtt       109
     Met Arg Met Arg Pro Ile Ser Lys Lys Ser Phe Leu Gln His Val
      1               5                  10                  15 gaa gag ctt tgc aca aac aac aac cta aag ttt caa gaa gaa ttt tcg        157
Glu Glu Leu Cys Thr Asn Asn Asn Leu Lys Phe Gln Glu Glu Phe Ser
                20                  25                  30 gaa tta cca aaa ttt ctt cag gat ctt tct tca act gat gct gat ctg        205
Glu Leu Pro Lys Phe Leu Gln Asp Leu Ser Ser Thr Asp Ala Asp Leu
            35                  40                  45 cct tgg aat aga gca aaa aac cgc ttc cca aac ata aaa cca tat aat        253
Pro Trp Asn Arg Ala Lys Asn Arg Phe Pro Asn Ile Lys Pro Tyr Asn
        50                  55                  60 aat aac aga gta aag ctg ata gct gac gct agt gtt cca ggt tcg gat        301
Asn Asn Arg Val Lys Leu Ile Ala Asp Ala Ser Val Pro Gly Ser Asp
65                  70                  75

-continued

| | | |
|---|---|---|
| tat att aat gcc agc tat att tct ggt tat tta tgt cca aat gaa ttt<br>Tyr Ile Asn Ala Ser Tyr Ile Ser Gly Tyr Leu Cys Pro Asn Glu Phe<br>80                          85                          90                        95 | 349 |
| att gct act caa ggt cca cta cca gga aca gtt gga gat ttt tgg aga<br>Ile Ala Thr Gln Gly Pro Leu Pro Gly Thr Val Gly Asp Phe Trp Arg<br>                        100                        105                        110 | 397 |
| atg gtg tgg gaa acc aga gca aaa aca tta gta atg cta aca cag tgt<br>Met Val Trp Glu Thr Arg Ala Lys Thr Leu Val Met Leu Thr Gln Cys<br>                115                        120                        125 | 445 |
| ttt gaa aaa gga cgg atc aga tgc cat cag tat tgg cca gag gac aac<br>Phe Glu Lys Gly Arg Ile Arg Cys His Gln Tyr Trp Pro Glu Asp Asn<br>130                          135                        140 | 493 |
| aag cca gtt act gtc ttt gga gat ata gtg att aca aag cta atg gag<br>Lys Pro Val Thr Val Phe Gly Asp Ile Val Ile Thr Lys Leu Met Glu<br>      145                        150                        155 | 541 |
| gat gtt caa ata gat tgg act atc agg gat ctg aaa att gaa agg cat<br>Asp Val Gln Ile Asp Trp Thr Ile Arg Asp Leu Lys Ile Glu Arg His<br>160                          165                        170                        175 | 589 |
| ggg gat tgc atg act gtt cga cag tgt aac ttt act gcc tgg cca gag<br>Gly Asp Cys Met Thr Val Arg Gln Cys Asn Phe Thr Ala Trp Pro Glu<br>                    180                        185                        190 | 637 |
| cat ggg gtt cct gag aac agc gcc cct cta att cac ttt gtg aag ttg<br>His Gly Val Pro Glu Asn Ser Ala Pro Leu Ile His Phe Val Lys Leu<br>                195                        200                        205 | 685 |
| gtt cga gca agc agg gca cat gac acc aca cct atg att gtt cac tgc<br>Val Arg Ala Ser Arg Ala His Asp Thr Thr Pro Met Ile Val His Cys<br>210                          215                        220 | 733 |
| agt gct gga gtt gga aga act gga gtt ttt att gct ctg gac cat tta<br>Ser Ala Gly Val Gly Arg Thr Gly Val Phe Ile Ala Leu Asp His Leu<br>      225                        230                        235 | 781 |
| aca caa cat ata aat gac cat gat ttt gtg gat ata tat gga cta gta<br>Thr Gln His Ile Asn Asp His Asp Phe Val Asp Ile Tyr Gly Leu Val<br>240                          245                        250                        255 | 829 |
| gct gaa ctg aga agt gaa aga atg tgc atg gtg cag aat ctg gca cag<br>Ala Glu Leu Arg Ser Glu Arg Met Cys Met Val Gln Asn Leu Ala Gln<br>                    260                        265                        270 | 877 |
| tat atc ttt tta cac cag tgc att ctg gat ctc tta tca aat aag gga<br>Tyr Ile Phe Leu His Gln Cys Ile Leu Asp Leu Leu Ser Asn Lys Gly<br>                275                        280                        285 | 925 |
| agt aat cag ccc atc tgt ttt gtt aac tat tca gca ctt cag aag atg<br>Ser Asn Gln Pro Ile Cys Phe Val Asn Tyr Ser Ala Leu Gln Lys Met<br>              290                        295                        300 | 973 |
| gac tct ttg gac gcc atg gaa ggt gat gtt gag ctt gaa tgg gaa gaa<br>Asp Ser Leu Asp Ala Met Glu Gly Asp Val Glu Leu Glu Trp Glu Glu<br>305                          310                        315 | 1021 |
| acc act atg taaatattca gaccaaagga tacaattgga agagattttt<br>Thr Thr Met<br>320 | 1070 |
| aaatcccagg ggccaaagtt accccctcat tcttccgaat tgaaatgtgc aaccttaaag | 1130 |
| aaatatctat gcttctctca ctgtgccttt ccaaacggat tgaacatttt aagactagtt | 1190 |
| cttgaaaata gctaatacag aataattatt tgttttgtac agaataaata ttatgcattt | 1250 |
| taaatgctta agaaaagaca tcccatatgt ttttgaagtc ctccatattt tggaataagc | 1310 |
| caaatagaaa attattatta tattagcatt aatgtttcaa tgtgaatttt ccctatgtat | 1370 |
| tggatttaat tttgaggaca aaagttgtaa atgttgattc agtagtgttg ttttggctta | 1430 |
| cagggtattg atgtttcttg tggataattt ccaggactgt cataatgatc tgtacttcca | 1490 |
| tgtacacccc tgtgttttga atcctctgtt ttatgagtgc tgagatatca tctcatgatc | 1550 |

-continued

```
ccgaacagct gaacagtaac cccctgacac tgcagggatt acttggcctt tatacaacac    1610
acagtagctc ttcagggaca cttagggcta tttaatttcg attgtgtctt cagtttgaga    1670
accttaaaag aaaattaaaa gtgcaattgc acacatgaaa ttacagagta ccattctagc    1730
aaacctacat ttgtaaactt taaaacacaa gttttncccc ctgtattgta tattcaaata    1790
tatagtaaat gtatcagagt atttgcccat tagatatgat caacctaata ttaacaattc    1850
tgaagagttt cttcagcaaa aatgtatcaa gagtaataaa aacactgtgc gtgtttcaag    1910
cttgtaaacc aatgatctgc tgctgtggtg ccaacagaga cttccaaatg gattatgtta    1970
aatggccgtc atttcatttc ccaaggttga ttttgagcag tatacttggt ggaactgaaa    2030
acaaagaaat taaccatcta tagcaaattc aaggtttctt tatagaaaat ctttcagcct    2090
ccatcttatt aaatagtgac aatgtggtaa gttttgaatt atatgaactc attttgtcat    2150
agatttcaat taagagtaat aaatagtatt aattatgctc ttctatgata agaagtatat    2210
cttatgctta tttccgctgg aacatatata tatatgaaat gctatggcca ataaaattga    2270
attttaatga aaaaaaaaa aaaaaaaaaa aaaaaaaa                             2309
```

<210> SEQ ID NO 11
<211> LENGTH: 322
<212> TYPE: PRT
<213> ORGANISM: Artificial Sequence
<220> FEATURE:
<223> OTHER INFORMATION: Description of Artificial Sequence: PTP-S31D

<400> SEQUENCE: 11

```
Met Arg Met Arg Pro Ile Ser Lys Lys Ser Phe Leu Gln His Val Glu
 1               5                  10                  15

Glu Leu Cys Thr Asn Asn Leu Lys Phe Gln Glu Glu Phe Ser Glu
                20                  25                  30

Leu Pro Lys Phe Leu Gln Asp Leu Ser Ser Thr Asp Ala Asp Leu Pro
            35                  40                  45

Trp Asn Arg Ala Lys Asn Arg Phe Pro Asn Ile Lys Pro Tyr Asn Asn
        50                  55                  60

Asn Arg Val Lys Leu Ile Ala Asp Ala Ser Val Pro Gly Ser Asp Tyr
    65                  70                  75                  80

Ile Asn Ala Ser Tyr Ile Ser Gly Tyr Leu Cys Pro Asn Glu Phe Ile
                85                  90                  95

Ala Thr Gln Gly Pro Leu Pro Gly Thr Val Gly Asp Phe Trp Arg Met
            100                 105                 110

Val Trp Glu Thr Arg Ala Lys Thr Leu Val Met Leu Thr Gln Cys Phe
        115                 120                 125

Glu Lys Gly Arg Ile Arg Cys His Gln Tyr Trp Pro Glu Asp Asn Lys
    130                 135                 140

Pro Val Thr Val Phe Gly Asp Ile Val Ile Thr Lys Leu Met Glu Asp
145                 150                 155                 160

Val Gln Ile Asp Trp Thr Ile Arg Asp Leu Lys Ile Glu Arg His Gly
                165                 170                 175

Asp Cys Met Thr Val Arg Gln Cys Asn Phe Thr Ala Trp Pro Glu His
            180                 185                 190

Gly Val Pro Glu Asn Ser Ala Pro Leu Ile His Phe Val Lys Leu Val
        195                 200                 205

Arg Ala Ser Arg Ala His Asp Thr Thr Pro Met Ile Val His Cys Ser
    210                 215                 220
```

-continued

Ala Gly Val Gly Arg Thr Gly Val Phe Ile Ala Leu Asp His Leu Thr
225                 230                 235                 240

Gln His Ile Asn Asp His Asp Phe Val Asp Ile Tyr Gly Leu Val Ala
            245                 250                 255

Glu Leu Arg Ser Glu Arg Met Cys Met Val Gln Asn Leu Ala Gln Tyr
            260                 265                 270

Ile Phe Leu His Gln Cys Ile Leu Asp Leu Leu Ser Asn Lys Gly Ser
            275                 280                 285

Asn Gln Pro Ile Cys Phe Val Asn Tyr Ser Ala Leu Gln Lys Met Asp
        290                 295                 300

Ser Leu Asp Ala Met Glu Gly Asp Val Glu Leu Glu Trp Glu Glu Thr
305                 310                 315                 320

Thr Met

<210> SEQ ID NO 12
<211> LENGTH: 292
<212> TYPE: PRT
<213> ORGANISM: Artificial Sequence
<220> FEATURE:
<223> OTHER INFORMATION: Description of Artificial Sequence: CD45

<400> SEQUENCE: 12

Met Asn Val Glu Pro Ile His Ala Asp Ile Leu Leu Glu Thr Tyr Lys
1               5                   10                  15

Arg Lys Ile Ala Asp Glu Gly Arg Leu Phe Leu Ala Glu Phe Gln Ser
            20                  25                  30

Ile Pro Arg Val Phe Ser Lys Phe Pro Ile Lys Glu Ala Arg Lys Pro
        35                  40                  45

Phe Asn Gln Asn Lys Asn Arg Tyr Val Asp Ile Leu Pro Tyr Asp Tyr
    50                  55                  60

Asn Arg Val Glu Leu Ser Glu Ile Asn Gly Asp Ala Gly Ser Asn Tyr
65                  70                  75                  80

Ile Asn Ala Ser Tyr Ile Asp Gly Phe Lys Glu Pro Arg Lys Tyr Ile
                85                  90                  95

Ala Ala Gln Gly Pro Arg Asp Glu Thr Val Asp Asp Phe Trp Arg Met
            100                 105                 110

Ile Trp Glu Gln Lys Ala Thr Val Ile Val Met Val Thr Arg Cys Glu
        115                 120                 125

Glu Gly Asn Arg Asn Lys Cys Ala Glu Tyr Trp Pro Ser Met Glu Glu
    130                 135                 140

Gly Thr Arg Ala Phe Gly Asp Val Val Lys Ile Asn Gln His Lys
145                 150                 155                 160

Arg Cys Pro Asp Tyr Ile Ile Gln Lys Leu Asn Ile Val Asn Lys Lys
                165                 170                 175

Glu Lys Ala Thr Gly Arg Glu Val Thr His Ile Gln Phe Thr Ser Trp
            180                 185                 190

Pro Asp His Gly Val Pro Glu Asp Pro His Leu Leu Leu Lys Leu Arg
        195                 200                 205

Arg Arg Val Asn Ala Phe Ser Asn Phe Phe Ser Gly Pro Ile Val Val
    210                 215                 220

His Cys Ser Ala Gly Val Gly Arg Thr Gly Thr Tyr Ile Gly Ile Asp
225                 230                 235                 240

Ala Met Leu Glu Gly Leu Glu Ala Glu Asn Lys Val Asp Val Tyr Gly
                245                 250                 255

```
Tyr Val Lys Leu Arg Arg Gln Arg Cys Leu Met Val Gln Val Glu
            260                 265                 270

Ala Gln Tyr Ile Leu Ile His Gln Ala Leu Val Glu Tyr Asn Gln Phe
        275                 280                 285

Gly Glu Thr Glu
    290

<210> SEQ ID NO 13
<211> LENGTH: 289
<212> TYPE: PRT
<213> ORGANISM: Artificial Sequence
<220> FEATURE:
<223> OTHER INFORMATION: Description of Artificial Sequence: LAR

<400> SEQUENCE: 13

Met Arg Asp His Pro Pro Ile Pro Ile Thr Asp Leu Ala Asp Asn Ile
 1               5                  10                  15

Glu Arg Leu Lys Ala Asn Asp Gly Leu Lys Phe Ser Gln Glu Tyr Glu
            20                  25                  30

Ser Ile Asp Pro Gly Gln Gln Phe Thr Trp Glu Asn Ser Asn Leu Glu
        35                  40                  45

Val Asn Lys Pro Lys Asn Arg Tyr Ala Asn Val Ile Ala Tyr Asp His
    50                  55                  60

Ser Arg Val Ile Leu Thr Ser Ile Asp Gly Val Pro Gly Ser Asp Tyr
65                  70                  75                  80

Ile Asn Ala Asn Tyr Ile Asp Gly Tyr Arg Lys Gln Asn Ala Tyr Ile
                85                  90                  95

Ala Thr Gln Gly Pro Leu Pro Glu Thr Met Gly Asp Phe Trp Arg Met
            100                 105                 110

Val Trp Glu Gln Arg Thr Ala Thr Val Val Met Met Thr Arg Leu Glu
        115                 120                 125

Glu Lys Ser Arg Val Lys Cys Asp Gln Tyr Trp Pro Ala Arg Gly Thr
130                 135                 140

Glu Thr Cys Gly Leu Ile Gln Val Thr Leu Leu Asp Thr Val Glu Leu
145                 150                 155                 160

Ala Thr Tyr Thr Val Arg Thr Phe Ala Leu His Lys Ser Gly Ser Ser
                165                 170                 175

Glu Lys Arg Glu Leu Arg Gln Phe Gln Phe Met Ala Trp Pro Asp His
            180                 185                 190

Gly Val Pro Glu Tyr Pro Thr Pro Ile Leu Ala Phe Leu Arg Arg Val
        195                 200                 205

Lys Ala Cys Asn Pro Leu Asp Ala Gly Pro Met Val Val His Cys Ser
    210                 215                 220

Ala Gly Val Gly Arg Thr Gly Cys Phe Ile Val Ile Asp Ala Met Leu
225                 230                 235                 240

Glu Arg Met Lys His Glu Lys Thr Val Asp Ile Tyr Gly His Val Thr
                245                 250                 255

Cys Met Arg Ser Gln Arg Asn Tyr Met Val Gln Thr Glu Asp Gln Tyr
            260                 265                 270

Val Phe Ile His Glu Ala Leu Leu Glu Ala Ala Thr Cys Gly His Thr
        275                 280                 285

Glu

<210> SEQ ID NO 14
<211> LENGTH: 2692
<212> TYPE: DNA
```

```
<213> ORGANISM: Homo sapiens
<220> FEATURE:
<221> NAME/KEY: modified_base
<222> LOCATION: (1)..(2692)
<223> OTHER INFORMATION: n = unknown nucleotide
<221> NAME/KEY: CDS
<222> LOCATION: (92..139, 259..1414)

<400> SEQUENCE: 14
gccttcgtca actaattctt cttaaattta gaacttcatc ccaataactt attagaaaaa      60
aaagaaagta gaataggttc tatggaatta a aac aag aaa aag aag tcg agt       112
                                   Asn Lys Lys Lys Lys Ser Ser
                                    1               5 agc tat aaa ttt gca aca tat tca gag aggtgatttt aacaaggaaa            159
Ser Tyr Lys Phe Ala Thr Tyr Ser Glu
         10                  15 ttatttgact aaatgtcttt acttaaaaag aaaactaaac ctaattttat atactttgtg    219
tgaaactccc ttcttggact ttactccgct tgttttaga att cga cag aag cag       273
                                              Ile Arg Gln Lys Gln
                                                           20 aaa gaa ggt ggc aca tac tct cct cag gat gca gaa att att gac act      321
Lys Glu Gly Gly Thr Tyr Ser Pro Gln Asp Ala Glu Ile Ile Asp Thr
                25                  30                  35 aaa ttg aag ctg gat cag ctc atc aca gtg gca gac ctg gaa ctg aag      369
Lys Leu Lys Leu Asp Gln Leu Ile Thr Val Ala Asp Leu Glu Leu Lys
        40                  45                  50 gac gag aga tta acg cga tac tct tca ttt ttc ttt aga cgc aag gag      417
Asp Glu Arg Leu Thr Arg Tyr Ser Ser Phe Phe Phe Arg Arg Lys Glu
55                  60                  65 att ttt gtc atc cag tta ctt agt tat aga aaa tcc atc aag cca ata      465
Ile Phe Val Ile Gln Leu Leu Ser Tyr Arg Lys Ser Ile Lys Pro Ile
 70                  75                  80                  85 agc aag aaa tcc ttc ctg caa cat gtt gaa gag ctt tgc aca aac aac      513
Ser Lys Lys Ser Phe Leu Gln His Val Glu Glu Leu Cys Thr Asn Asn
                90                  95                 100 aac cta aag ttt caa gaa gaa ttt tcg gaa tta cca aaa ttt ctt cag      561
Asn Leu Lys Phe Gln Glu Glu Phe Ser Glu Leu Pro Lys Phe Leu Gln
            105                 110                 115 gat ctt tct tca act gat gct gat ctg cct tgg aat aga gca aaa aac      609
Asp Leu Ser Ser Thr Asp Ala Asp Leu Pro Trp Asn Arg Ala Lys Asn
        120                 125                 130 cgc ttc cca aac ata aaa cca tat aat aat aac aga gta aag ctg ata      657
Arg Phe Pro Asn Ile Lys Pro Tyr Asn Asn Asn Arg Val Lys Leu Ile
    135                 140                 145 gct gac gct agt gtt cca ggt tcg gat tat att aat gcc agc tat att      705
Ala Asp Ala Ser Val Pro Gly Ser Asp Tyr Ile Asn Ala Ser Tyr Ile
150                 155                 160                 165 tct ggt tat tta tgt cca aat gaa ttt att gct act caa ggt cca cta      753
Ser Gly Tyr Leu Cys Pro Asn Glu Phe Ile Ala Thr Gln Gly Pro Leu
                170                 175                 180 cca gga aca gtt gga gat ttt tgg aga atg gtg tgg gaa acc aga gca      801
Pro Gly Thr Val Gly Asp Phe Trp Arg Met Val Trp Glu Thr Arg Ala
            185                 190                 195 aaa aca tta gta atg cta aca cag tgt ttt gaa aaa gga cgg atc aga      849
Lys Thr Leu Val Met Leu Thr Gln Cys Phe Glu Lys Gly Arg Ile Arg
        200                 205                 210 tgc cat cag tat tgg cca gag gac aac aag cca gtt act gtc ttt gga      897
Cys His Gln Tyr Trp Pro Glu Asp Asn Lys Pro Val Thr Val Phe Gly
    215                 220                 225
```

```
gat ata gtg att aca aag cta atg gag gat gtt caa ata gat tgg act      945
Asp Ile Val Ile Thr Lys Leu Met Glu Asp Val Gln Ile Asp Trp Thr
230                 235                 240                 245 atc agg gat ctg aaa att gaa agg cat ggg gat tgc atg act gtt cga      993
Ile Arg Asp Leu Lys Ile Glu Arg His Gly Asp Cys Met Thr Val Arg
                250                 255                 260 cag tgt aac ttt act gcc tgg cca gag cat ggg gtt cct gag aac agc     1041
Gln Cys Asn Phe Thr Ala Trp Pro Glu His Gly Val Pro Glu Asn Ser
            265                 270                 275 gcc cct cta att cac ttt gtg aag ttg gtt cga gca agc agg gca cat     1089
Ala Pro Leu Ile His Phe Val Lys Leu Val Arg Ala Ser Arg Ala His
        280                 285                 290 gac acc aca cct atg att gtt cac tgc agt gct gga gtt gga aga act     1137
Asp Thr Thr Pro Met Ile Val His Cys Ser Ala Gly Val Gly Arg Thr
    295                 300                 305 gga gtt ttt att gct ctg gac cat tta aca caa cat ata aat gac cat     1185
Gly Val Phe Ile Ala Leu Asp His Leu Thr Gln His Ile Asn Asp His
310                 315                 320                 325 gat ttt gtg gat ata tat gga cta gta gct gaa ctg aga agt gaa aga     1233
Asp Phe Val Asp Ile Tyr Gly Leu Val Ala Glu Leu Arg Ser Glu Arg
                330                 335                 340 atg tgc atg gtg cag aat ctg gca cag tat atc ttt tta cac cag tgc     1281
Met Cys Met Val Gln Asn Leu Ala Gln Tyr Ile Phe Leu His Gln Cys
            345                 350                 355 att ctg gat ctc tta tca aat aag gga agt aat cag ccc atc tgt ttt     1329
Ile Leu Asp Leu Leu Ser Asn Lys Gly Ser Asn Gln Pro Ile Cys Phe
        360                 365                 370 gtt aac tat tca gca ctt cag aag atg gac tct ttg gac gcc atg gaa     1377
Val Asn Tyr Ser Ala Leu Gln Lys Met Asp Ser Leu Asp Ala Met Glu
    375                 380                 385 ggt gat gtt gag ctt gaa tgg gaa gaa acc act atg taaatattca          1423
Gly Asp Val Glu Leu Glu Trp Glu Glu Thr Thr Met
390                 395                 400 gaccaaagga tacaattgga agagattttt aaatcccagg ggccaaagtt accccctcat   1483
tcttccgaat tgaaatgtgc aaccttaaag aaatatctat gcttctctca ctgtgccttt   1543
ccaaacggat tgaacatttt aagactagtt cttgaaaata gctaatacag aataattatt   1603
tgttttgtac agaataaata ttatgcattt taaatgctta agaaaagaca tcccatatgt   1663
ttttgaagtc ctccatattt tggaataagc caaatagaaa attattatta tattagcatt   1723
aatgtttcaa tgtgaatttt ccctatgtat tggatttaat tttgaggaca aaagttgtaa   1783
atgttgattc agtagtgttg ttttggctta cagggtattg atgtttcttg tggataattt   1843
ccaggactgt cataatgatc tgtacttcca tgtacacccc tgtgttttga atcctctgtt   1903
ttatgagtgc tgagatatca tctcatgatc ccgaacagct gaacagtaac cccctgacac   1963
tgcagggatt acttggcctt tatacaacac acagtagctc ttcagggaca cttagggcta   2023
tttaatttcg attgtgtctt cagtttgaga accttaaaag aaaattaaaa gtgcaattgc   2083
acacatgaaa ttacagagta ccattctagc aaacctacat tgtaaactt taaaacacaa    2143 gtttttnccc ctgtattgta tattcaaata tatagtaaat gtatcagagt atttgcccat   2203
tagatatgat caacctaata ttaacaattc tgaagagttt cttcagcaaa aatgtatcaa   2263
gagtaataaa aacactgtgc gtgtttcaag cttgtaaacc aatgatctgc tgctgtggtg   2323
ccaacagaga cttccaaatg gattatgtta aatggccgtc atttcatttc ccaaggttga   2383
ttttgagcag tatacttggt ggaactgaaa acaaagaaat taaccatcta tagcaaattc   2443
aaggtttctt tatagaaaat ctttcagcct ccatcttatt aaatagtgac aatgtggtaa   2503
```

-continued

```
gttttgaatt atatgaactc attttgtcat agatttcaat taagagtaat aaatagtatt    2563
aattatgctc ttctatgata agaagtatat cttatgctta tttccgctgg aacatatata    2623
tatatgaaat gctatggcca ataaaattga attttaatga aaaaaaaaaa aaaaaaaaa     2683 aaaaaaaaa                                                            2692
```

<210> SEQ ID NO 15
<211> LENGTH: 401
<212> TYPE: PRT
<213> ORGANISM: Homo sapiens

<400> SEQUENCE: 15

```
Asn Lys Lys Lys Ser Ser Tyr Lys Phe Ala Thr Tyr Ser Glu
 1               5                  10                  15

Ile Arg Gln Lys Gln Lys Glu Gly Gly Thr Tyr Ser Pro Gln Asp Ala
                20                  25                  30

Glu Ile Ile Asp Thr Lys Leu Lys Leu Asp Gln Leu Ile Thr Val Ala
             35                  40                  45

Asp Leu Glu Leu Lys Asp Glu Arg Leu Thr Arg Tyr Ser Ser Phe Phe
         50                  55                  60

Phe Arg Arg Lys Glu Ile Phe Val Ile Gln Leu Leu Ser Tyr Arg Lys
     65                  70                  75                  80

Ser Ile Lys Pro Ile Ser Lys Lys Ser Phe Leu Gln His Val Glu Glu
                 85                  90                  95

Leu Cys Thr Asn Asn Leu Lys Phe Gln Glu Glu Phe Ser Glu Leu
            100                 105                 110

Pro Lys Phe Leu Gln Asp Leu Ser Ser Thr Asp Ala Asp Leu Pro Trp
        115                 120                 125

Asn Arg Ala Lys Asn Arg Phe Pro Asn Ile Lys Pro Tyr Asn Asn Asn
    130                 135                 140

Arg Val Lys Leu Ile Ala Asp Ala Ser Val Pro Gly Ser Asp Tyr Ile
145                 150                 155                 160

Asn Ala Ser Tyr Ile Ser Gly Tyr Leu Cys Pro Asn Glu Phe Ile Ala
                165                 170                 175

Thr Gln Gly Pro Leu Pro Gly Thr Val Gly Asp Phe Trp Arg Met Val
            180                 185                 190

Trp Glu Thr Arg Ala Lys Thr Leu Val Met Leu Thr Gln Cys Phe Glu
        195                 200                 205

Lys Gly Arg Ile Arg Cys His Gln Tyr Trp Pro Glu Asp Asn Lys Pro
    210                 215                 220

Val Thr Val Phe Gly Asp Ile Val Ile Thr Lys Leu Met Glu Asp Val
225                 230                 235                 240

Gln Ile Asp Trp Thr Ile Arg Asp Leu Lys Ile Glu Arg His Gly Asp
                245                 250                 255

Cys Met Thr Val Arg Gln Cys Asn Phe Thr Ala Trp Pro Glu His Gly
            260                 265                 270

Val Pro Glu Asn Ser Ala Pro Leu Ile His Phe Val Lys Leu Val Arg
        275                 280                 285

Ala Ser Arg Ala His Asp Thr Thr Pro Met Ile Val His Cys Ser Ala
    290                 295                 300

Gly Val Gly Arg Thr Gly Val Phe Ile Ala Leu Asp His Leu Thr Gln
305                 310                 315                 320

His Ile Asn Asp His Asp Phe Val Asp Ile Tyr Gly Leu Val Ala Glu
                325                 330                 335
```

```
Leu Arg Ser Glu Arg Met Cys Met Val Gln Asn Leu Ala Gln Tyr Ile
            340                 345                 350

Phe Leu His Gln Cys Ile Leu Asp Leu Leu Ser Asn Lys Gly Ser Asn
            355                 360                 365

Gln Pro Ile Cys Phe Val Asn Tyr Ser Ala Leu Gln Lys Met Asp Ser
            370                 375                 380

Leu Asp Ala Met Glu Gly Asp Val Glu Leu Glu Trp Glu Glu Thr Thr
385                 390                 395                 400

Met

<210> SEQ ID NO 16
<211> LENGTH: 48
<212> TYPE: PRT
<213> ORGANISM: Homo sapiens

<400> SEQUENCE: 16

Ile Arg Gln Lys Gln Lys Glu Gly Gly Thr Tyr Ser Pro Gln Asp Ala
1               5                   10                  15

Glu Ile Ile Asp Thr Lys Leu Lys Leu Asp Gln Leu Ile Thr Val Ala
            20                  25                  30

Asp Leu Glu Leu Lys Asp Glu Arg Leu Thr Arg Pro Ile Ser Lys Lys
        35                  40                  45

<210> SEQ ID NO 17
<211> LENGTH: 57
<212> TYPE: PRT
<213> ORGANISM: Homo sapiens

<400> SEQUENCE: 17

Ile Arg Gln Lys Gln Lys Glu Gly Gly Thr Tyr Ser Pro Gln Asp Ala
1               5                   10                  15

Glu Ile Ile Asp Thr Lys Leu Lys Leu Asp Gln Leu Ile Thr Val Ala
            20                  25                  30

Asp Leu Glu Leu Lys Asp Glu Arg Leu Thr Arg Leu Leu Ser Tyr Arg
        35                  40                  45

Lys Ser Ile Lys Pro Ile Ser Lys Lys
    50                  55

<210> SEQ ID NO 18
<211> LENGTH: 72
<212> TYPE: PRT
<213> ORGANISM: Homo sapiens

<400> SEQUENCE: 18

Ile Arg Gln Lys Gln Lys Gln Gly Gly Thr Tyr Ser Pro Gln Asp Ala
1               5                   10                  15

Glu Ile Ile Asp Thr Lys Leu Lys Leu Asp Gln Leu Ile Thr Val Ala
            20                  25                  30

Asp Leu Glu Leu Lys Asp Glu Arg Leu Thr Arg Tyr Ser Ser Phe Phe
        35                  40                  45

Phe Arg Arg Lys Glu Ile Phe Val Ile Gln Leu Leu Ser Tyr Arg Lys
    50                  55                  60

Ser Ile Lys Pro Ile Ser Lys Lys
65                  70

<210> SEQ ID NO 19
<211> LENGTH: 85
<212> TYPE: PRT
<213> ORGANISM: Homo sapiens
```

```
<400> SEQUENCE: 19

Lys Ser Ser Tyr Lys Phe Ala Thr Tyr Ser Glu Arg Ile Arg Gln
 1               5                  10                  15

Lys Gln Lys Glu Gly Gly Thr Tyr Ser Pro Gln Asp Ala Glu Ile Ile
             20                  25                  30

Asp Thr Lys Leu Lys Leu Asp Gln Leu Ile Thr Val Ala Asp Leu Glu
             35                  40                  45

Leu Lys Asp Glu Arg Leu Thr Arg Tyr Ser Ser Phe Phe Arg Arg
 50                  55                  60

Lys Glu Ile Phe Val Ile Gln Leu Leu Ser Tyr Arg Lys Ser Ile Lys
 65                  70                  75                  80

Pro Ile Ser Lys Lys
             85

<210> SEQ ID NO 20
<211> LENGTH: 78
<212> TYPE: PRT
<213> ORGANISM: Homo sapiens

<400> SEQUENCE: 20

Glu Lys Gln Val Thr Thr Ile Arg Gln Lys Gln Lys Glu Gly Gly Thr
 1               5                  10                  15

Tyr Ser Pro Gln Asp Ala Glu Ile Ile Asp Thr Lys Leu Lys Leu Asp
             20                  25                  30

Gln Leu Ile Thr Val Ala Asp Leu Glu Leu Lys Asp Glu Arg Leu Thr
             35                  40                  45

Arg Tyr Ser Ser Phe Phe Arg Arg Lys Glu Ile Phe Val Ile Gln
 50                  55                  60

Leu Leu Ser Tyr Arg Lys Ser Ile Lys Pro Ile Ser Lys Lys
 65                  70                  75

<210> SEQ ID NO 21
<211> LENGTH: 3973
<212> TYPE: DNA
<213> ORGANISM: Artificial Sequence
<220> FEATURE:
<223> OTHER INFORMATION: Description of Artificial Sequence: PTPS31-RD#2
<221> NAME/KEY: modified_base
<222> LOCATION: (1)..(3973)
<223> OTHER INFORMATION: n = unknown nucleotide
<221> NAME/KEY: CDS
<222> LOCATION: (1)..(2694)

<400> SEQUENCE: 21 gga agg tct ggg agc cag tac cct gtg gat aca aaa gtt ccc agt gtt      48
Gly Arg Ser Gly Ser Gln Tyr Pro Val Asp Thr Lys Val Pro Ser Val
 1               5                  10                  15 ccc aca aat att gct ttt tct gat gtt cag tca act agt gca aca ttg      96
Pro Thr Asn Ile Ala Phe Ser Asp Val Gln Ser Thr Ser Ala Thr Leu
             20                  25                  30 aca tgg ata aga cct gac act atc ctt ggc tac ttt caa aat tac aaa     144
Thr Trp Ile Arg Pro Asp Thr Ile Leu Gly Tyr Phe Gln Asn Tyr Lys
             35                  40                  45 att acc act caa ctt cgt gct caa aaa tgc aaa gaa tgg gaa tcc gaa     192
Ile Thr Thr Gln Leu Arg Ala Gln Lys Cys Lys Glu Trp Glu Ser Glu
 50                  55                  60 gaa tgt gtt gaa tat caa aaa att caa tac ctc tat gaa gct cac tta     240
Glu Cys Val Glu Tyr Gln Lys Ile Gln Tyr Leu Tyr Glu Ala His Leu
 65                  70                  75                  80
```

```
act gaa gag aca gta tat gga tta aag aaa ttt aga tgg tat aga ttc    288
Thr Glu Glu Thr Val Tyr Gly Leu Lys Lys Phe Arg Trp Tyr Arg Phe
                 85                  90                  95 caa gtg gct gcc agc acc aat gct ggc tat ggc aat gct tca aac tgg    336
Gln Val Ala Ala Ser Thr Asn Ala Gly Tyr Gly Asn Ala Ser Asn Trp
            100                 105                 110 att tct aca aaa act ctg cct ggc cct cca gat ggt cct cct gaa aat    384
Ile Ser Thr Lys Thr Leu Pro Gly Pro Pro Asp Gly Pro Pro Glu Asn
        115                 120                 125 gtt cat gta gta gca aca tca cct ttt agc atc agc ata agc tgg agt    432
Val His Val Val Ala Thr Ser Pro Phe Ser Ile Ser Ile Ser Trp Ser
    130                 135                 140 gaa cct gct gtc att act gga cca aca tgt tat ctg att gat gtc aaa    480
Glu Pro Ala Val Ile Thr Gly Pro Thr Cys Tyr Leu Ile Asp Val Lys
145                 150                 155                 160 tcg gta gat aat gat gaa ttt aat ata tcc ttc atc aag tca aat gaa    528
Ser Val Asp Asn Asp Glu Phe Asn Ile Ser Phe Ile Lys Ser Asn Glu
                165                 170                 175 gaa aat aaa acc ata gaa att aaa gat tta gaa ata ttc aca agg tat    576
Glu Asn Lys Thr Ile Glu Ile Lys Asp Leu Glu Ile Phe Thr Arg Tyr
            180                 185                 190 tct gta gtg atc act gca ttt act ggg aac att agt gct gca tat gta    624
Ser Val Val Ile Thr Ala Phe Thr Gly Asn Ile Ser Ala Ala Tyr Val
        195                 200                 205 gaa ggg aag tca agt gct gaa atg att gtt act act tta gaa tca gcc    672
Glu Gly Lys Ser Ser Ala Glu Met Ile Val Thr Thr Leu Glu Ser Ala
    210                 215                 220 cca aag gac cca cct aac aac atg aca ttt cag aag ata cca gat gaa    720
Pro Lys Asp Pro Pro Asn Asn Met Thr Phe Gln Lys Ile Pro Asp Glu
225                 230                 235                 240 gtt aca aaa ttt caa tta acg ttc ctt cct cct tct caa cct aat gga    768
Val Thr Lys Phe Gln Leu Thr Phe Leu Pro Pro Ser Gln Pro Asn Gly
                245                 250                 255 aat atc caa gta tat caa gct ctg gtt tac cga gaa gat gat cct act    816
Asn Ile Gln Val Tyr Gln Ala Leu Val Tyr Arg Glu Asp Asp Pro Thr
            260                 265                 270 gct gtc cag att cac aac ctc agt att ata cag aaa acc aac aca ttc    864
Ala Val Gln Ile His Asn Leu Ser Ile Ile Gln Lys Thr Asn Thr Phe
        275                 280                 285 gtc att gca atg cta gaa gga cta aaa ggt gga cat aca tac aat atc    912
Val Ile Ala Met Leu Glu Gly Leu Lys Gly Gly His Thr Tyr Asn Ile
    290                 295                 300 agt gtt tac gca gtc aat agt gct ggt gca ggt cca aag gtt ccg atg    960
Ser Val Tyr Ala Val Asn Ser Ala Gly Ala Gly Pro Lys Val Pro Met
305                 310                 315                 320 aga ata acc atg gat atc aaa gct cca gca cga cca aaa acc aaa cca    1008
Arg Ile Thr Met Asp Ile Lys Ala Pro Ala Arg Pro Lys Thr Lys Pro
                325                 330                 335 acc cct att tat gat gcc aca gga aaa ctg ctt gtg act tca aca aca    1056
Thr Pro Ile Tyr Asp Ala Thr Gly Lys Leu Leu Val Thr Ser Thr Thr
            340                 345                 350 att aca atc aga atg cca ata tgt tac tac agt gat gat cat gga cca    1104
Ile Thr Ile Arg Met Pro Ile Cys Tyr Tyr Ser Asp Asp His Gly Pro
        355                 360                 365 ata aaa aat gta caa gtg ctt gtg aca gaa aca gga gct cag cat gat    1152
Ile Lys Asn Val Gln Val Leu Val Thr Glu Thr Gly Ala Gln His Asp
    370                 375                 380 gga aat gta aca aag tgg tat gat gca tat ttt aat aaa gca agg cca    1200
Gly Asn Val Thr Lys Trp Tyr Asp Ala Tyr Phe Asn Lys Ala Arg Pro
385                 390                 395                 400
```

-continued

```
tat ttt aca aat gaa ggc ttt cct aac cct cca tgt aca gaa gga aag    1248
Tyr Phe Thr Asn Glu Gly Phe Pro Asn Pro Pro Cys Thr Glu Gly Lys
            405                 410                 415 aca aag ttt agt ggc aat gaa gaa atc tac atc ata ggt gct gat aat    1296
Thr Lys Phe Ser Gly Asn Glu Glu Ile Tyr Ile Ile Gly Ala Asp Asn
        420                 425                 430 gca tgc atg att cct ggc aat gaa gac aaa att tgc aat gga cca ctg    1344
Ala Cys Met Ile Pro Gly Asn Glu Asp Lys Ile Cys Asn Gly Pro Leu
    435                 440                 445 aaa cca aaa aag caa tac tta ttt aaa ttt aga gct aca aat att atg    1392
Lys Pro Lys Lys Gln Tyr Leu Phe Lys Phe Arg Ala Thr Asn Ile Met
450                 455                 460 gga caa ttt act gac tct gat tat tct gac cct gtt aag act tta ggg    1440
Gly Gln Phe Thr Asp Ser Asp Tyr Ser Asp Pro Val Lys Thr Leu Gly
465                 470                 475                 480 gaa gga ctt tca gaa aga acc gta gag atc att ctt tcc gtc act ttg    1488
Glu Gly Leu Ser Glu Arg Thr Val Glu Ile Ile Leu Ser Val Thr Leu
            485                 490                 495 tgt atc ctt tca ata att ctc ctt gga aca gct att ttt gca ttt gca    1536
Cys Ile Leu Ser Ile Ile Leu Leu Gly Thr Ala Ile Phe Ala Phe Ala
        500                 505                 510 aga att cga cag aag cag aaa gaa ggt ggc aca tac tct cct cag gat    1584
Arg Ile Arg Gln Lys Gln Lys Glu Gly Gly Thr Tyr Ser Pro Gln Asp
    515                 520                 525 gca gaa att att gac act aaa ttg aag ctg gat cag ctc atc aca gtg    1632
Ala Glu Ile Ile Asp Thr Lys Leu Lys Leu Asp Gln Leu Ile Thr Val
530                 535                 540 gca gac ctg gaa ctg aag gac gag aga tta acg cga tac tct tca ttt    1680
Ala Asp Leu Glu Leu Lys Asp Glu Arg Leu Thr Arg Tyr Ser Ser Phe
545                 550                 555                 560 ttc ttt aga cgc aag gag att ttt gtc atc cag tta ctt agt tat aga    1728
Phe Phe Arg Arg Lys Glu Ile Phe Val Ile Gln Leu Leu Ser Tyr Arg
            565                 570                 575 aaa tcc atc aag cca ata agc aag aaa tcc ttc ctg caa cat gtt gaa    1776
Lys Ser Ile Lys Pro Ile Ser Lys Lys Ser Phe Leu Gln His Val Glu
        580                 585                 590 gag ctt tgc aca aac aac aac cta aag ttt caa gaa gaa ttt tcg gaa    1824
Glu Leu Cys Thr Asn Asn Asn Leu Lys Phe Gln Glu Glu Phe Ser Glu
    595                 600                 605 tta cca aaa ttt ctt cag gat ctt tct tca act gat gct gat ctg cct    1872
Leu Pro Lys Phe Leu Gln Asp Leu Ser Ser Thr Asp Ala Asp Leu Pro
610                 615                 620 tgg aat aga gca aaa aac cgc ttc cca aac ata aaa cca tat aat aat    1920
Trp Asn Arg Ala Lys Asn Arg Phe Pro Asn Ile Lys Pro Tyr Asn Asn
625                 630                 635                 640 aac aga gta aag ctg ata gct gac gct agt gtt cca ggt tcg gat tat    1968
Asn Arg Val Lys Leu Ile Ala Asp Ala Ser Val Pro Gly Ser Asp Tyr
            645                 650                 655 att aat gcc agc tat att tct ggt tat tta tgt cca aat gaa ttt att    2016
Ile Asn Ala Ser Tyr Ile Ser Gly Tyr Leu Cys Pro Asn Glu Phe Ile
        660                 665                 670 gct act caa ggt cca cta cca gga aca gtt gga gat ttt tgg aga atg    2064
Ala Thr Gln Gly Pro Leu Pro Gly Thr Val Gly Asp Phe Trp Arg Met
    675                 680                 685 gtg tgg gaa acc aga gca aaa aca tta gta atg cta aca cag tgt ttt    2112
Val Trp Glu Thr Arg Ala Lys Thr Leu Val Met Leu Thr Gln Cys Phe
690                 695                 700 gaa aaa gga cgg atc aga tgc cat cag tat tgg cca gag gac aac aag    2160
Glu Lys Gly Arg Ile Arg Cys His Gln Tyr Trp Pro Glu Asp Asn Lys
705                 710                 715                 720
```

-continued

| | |
|---|---|
| cca gtt act gtc ttt gga gat ata gtg att aca aag cta atg gag gat<br>Pro Val Thr Val Phe Gly Asp Ile Val Ile Thr Lys Leu Met Glu Asp<br>              725                      730                    735 | 2208 |
| gtt caa ata gat tgg act atc agg gat ctg aaa att gaa agg cat ggg<br>Val Gln Ile Asp Trp Thr Ile Arg Asp Leu Lys Ile Glu Arg His Gly<br>    740                        745                      750 | 2256 |
| gat tgc atg act gtt cga cag tgt aac ttt act gcc tgg cca gag cat<br>Asp Cys Met Thr Val Arg Gln Cys Asn Phe Thr Ala Trp Pro Glu His<br>             755                      760                    765 | 2304 |
| ggg gtt cct gag aac agc gcc cct cta att cac ttt gtg aag ttg gtt<br>Gly Val Pro Glu Asn Ser Ala Pro Leu Ile His Phe Val Lys Leu Val<br>770                          775                      780 | 2352 |
| cga gca agc agg gca cat gac acc aca cct atg att gtt cac tgc agt<br>Arg Ala Ser Arg Ala His Asp Thr Thr Pro Met Ile Val His Cys Ser<br>785                      790                      795                    800 | 2400 |
| gct gga gtt gga aga act gga gtt ttt att gct ctg gac cat tta aca<br>Ala Gly Val Gly Arg Thr Gly Val Phe Ile Ala Leu Asp His Leu Thr<br>                    805                      810                    815 | 2448 |
| caa cat ata aat gac cat gat ttt gtg gat ata tat gga cta gta gct<br>Gln His Ile Asn Asp His Asp Phe Val Asp Ile Tyr Gly Leu Val Ala<br>            820                      825                    830 | 2496 |
| gaa ctg aga agt gaa aga atg tgc atg gtg cag aat ctg gca cag tat<br>Glu Leu Arg Ser Glu Arg Met Cys Met Val Gln Asn Leu Ala Gln Tyr<br>835                          840                      845 | 2544 |
| atc ttt tta cac cag tgc att ctg gat ctc tta tca aat aag gga agt<br>Ile Phe Leu His Gln Cys Ile Leu Asp Leu Leu Ser Asn Lys Gly Ser<br>    850                        855                      860 | 2592 |
| aat cag ccc atc tgt ttt gtt aac tat tca gca ctt cag aag atg gac<br>Asn Gln Pro Ile Cys Phe Val Asn Tyr Ser Ala Leu Gln Lys Met Asp<br>865                      870                      875                    880 | 2640 |
| tct ttg gac gcc atg gaa ggt gat gtt gag ctt gaa tgg gaa gaa acc<br>Ser Leu Asp Ala Met Glu Gly Asp Val Glu Leu Glu Trp Glu Glu Thr<br>                    885                      890                    895 | 2688 |
| act atg taaatattca gaccaaagga tacaattgga agagattttt aaatcccagg<br>Thr Met | 2744 |
| ggccaaagtt acccctcat tcttccgaat tgaaatgtgc aaccttaaag aaatatctat | 2804 |
| gcttctctca ctgtgccttt ccaaacggat tgaacatttt aagactagtt cttgaaaata | 2864 |
| gctaatacag aataattatt tgttttgtac agaataaata ttatgcattt taaatgctta | 2924 |
| agaaaagaca tcccatatgt ttttgaagtc ctccatattt tggaataagc caaatagaaa | 2984 |
| attattatta tattagcatt aatgtttcaa tgtgaatttt ccctatgtat tggatttaat | 3044 |
| tttgaggaca aaagttgtaa atgttgattc agtagtgttg ttttggctta cagggtattg | 3104 |
| atgtttcttg tggataattt ccaggactgt cataatgatc tgtacttcca tgtacacccc | 3164 |
| tgtgttttga atcctctgtt ttatgagtgc tgagatatca tctcatgatc ccgaacagct | 3224 |
| gaacagtaac cccctgacac tgcagggatt acttggcctt tatacaacac acagtagctc | 3284 |
| ttcagggaca cttagggcta tttaatttcg attgtgtctt cagtttgaga accttaaaag | 3344 |
| aaaattaaaa gtgcaattgc acacatgaaa ttacagagta ccattctagc aaacctacat | 3404 |
| ttgtaaactt taaaacacaa gttttncccc ctgtattgta tattcaaata tatagtaaat | 3464 |
| gtatcagagt atttgcccat tagatatgat caacctaata ttaacaattc tgaagagttt | 3524 |
| cttcagcaaa aatgtatcaa gagtaataaa aacactgtgc gtgtttcaag cttgtaaacc | 3584 |
| aatgatctgc tgctgtggtg ccaacagaga cttccaaatg gattatgtta aatggccgtc | 3644 |
| atttcatttc ccaaggttga ttttgagcag tatacttggt ggaactgaaa acaaagaaat | 3704 |

| | | | |
|---|---|---|---|
| taaccatcta | tagcaaattc | aaggtttctt | tatagaaaat ctttcagcct ccatcttatt | 3764 |
| aaatagtgac | aatgtggtaa | gttttgaatt | atatgaactc attttgtcat agatttcaat | 3824 |
| taagagtaat | aaaatagtatt | aattatgctc | ttctatgata agaagtatat cttatgctta | 3884 |
| tttccgctgg | aacatatata | tatgaaaat | gctatggcca ataaaattga attttaatga | 3944 |
| aaaaaaaaaa | aaaaaaaaaa | aaaaaaaaa | | 3973 |

<210> SEQ ID NO 22
<211> LENGTH: 898
<212> TYPE: PRT
<213> ORGANISM: Artificial Sequence
<220> FEATURE:
<223> OTHER INFORMATION: Description of Artificial Sequence: PTPS31-RD#2

<400> SEQUENCE: 22

```
Gly Arg Ser Gly Ser Gln Tyr Pro Val Asp Thr Lys Val Pro Ser Val
 1               5                  10                  15

Pro Thr Asn Ile Ala Phe Ser Asp Val Gln Ser Thr Ser Ala Thr Leu
            20                  25                  30

Thr Trp Ile Arg Pro Asp Thr Ile Leu Gly Tyr Phe Gln Asn Tyr Lys
        35                  40                  45

Ile Thr Thr Gln Leu Arg Ala Gln Lys Cys Lys Glu Trp Glu Ser Glu
    50                  55                  60

Glu Cys Val Glu Tyr Gln Lys Ile Gln Tyr Leu Tyr Glu Ala His Leu
65                  70                  75                  80

Thr Glu Glu Thr Val Tyr Gly Leu Lys Lys Phe Arg Trp Tyr Arg Phe
                85                  90                  95

Gln Val Ala Ala Ser Thr Asn Ala Gly Tyr Gly Asn Ala Ser Asn Trp
            100                 105                 110

Ile Ser Thr Lys Thr Leu Pro Gly Pro Pro Asp Gly Pro Pro Glu Asn
        115                 120                 125

Val His Val Ala Thr Ser Pro Phe Ser Ile Ser Ile Ser Trp Ser
    130                 135                 140

Glu Pro Ala Val Ile Thr Gly Pro Thr Cys Tyr Leu Ile Asp Val Lys
145                 150                 155                 160

Ser Val Asp Asn Asp Glu Phe Asn Ile Ser Phe Ile Lys Ser Asn Glu
                165                 170                 175

Glu Asn Lys Thr Ile Glu Ile Lys Asp Leu Glu Ile Phe Thr Arg Tyr
            180                 185                 190

Ser Val Val Ile Thr Ala Phe Thr Gly Asn Ile Ser Ala Ala Tyr Val
        195                 200                 205

Glu Gly Lys Ser Ser Ala Glu Met Ile Val Thr Thr Leu Glu Ser Ala
    210                 215                 220

Pro Lys Asp Pro Pro Asn Asn Met Thr Phe Gln Lys Ile Pro Asp Glu
225                 230                 235                 240

Val Thr Lys Phe Gln Leu Thr Phe Leu Pro Pro Ser Gln Pro Asn Gly
                245                 250                 255

Asn Ile Gln Val Tyr Gln Ala Leu Val Tyr Arg Glu Asp Asp Pro Thr
            260                 265                 270

Ala Val Gln Ile His Asn Leu Ser Ile Ile Gln Lys Thr Asn Thr Phe
        275                 280                 285

Val Ile Ala Met Leu Glu Gly Leu Lys Gly Gly His Thr Tyr Asn Ile
    290                 295                 300

Ser Val Tyr Ala Val Asn Ser Ala Gly Ala Gly Pro Lys Val Pro Met
305                 310                 315                 320
```

-continued

```
Arg Ile Thr Met Asp Ile Lys Ala Pro Ala Arg Pro Lys Thr Lys Pro
                325                 330                 335
Thr Pro Ile Tyr Asp Ala Thr Gly Lys Leu Leu Val Thr Ser Thr Thr
            340                 345                 350
Ile Thr Ile Arg Met Pro Ile Cys Tyr Tyr Ser Asp His Gly Pro
        355                 360                 365
Ile Lys Asn Val Gln Val Leu Val Thr Glu Thr Gly Ala Gln His Asp
    370                 375                 380
Gly Asn Val Thr Lys Trp Tyr Asp Ala Tyr Phe Asn Lys Ala Arg Pro
385                 390                 395                 400
Tyr Phe Thr Asn Glu Gly Phe Pro Asn Pro Pro Cys Thr Glu Gly Lys
                405                 410                 415
Thr Lys Phe Ser Gly Asn Glu Glu Ile Tyr Ile Ile Gly Ala Asp Asn
            420                 425                 430
Ala Cys Met Ile Pro Gly Asn Glu Asp Lys Ile Cys Asn Gly Pro Leu
        435                 440                 445
Lys Pro Lys Lys Gln Tyr Leu Phe Lys Phe Arg Ala Thr Asn Ile Met
    450                 455                 460
Gly Gln Phe Thr Asp Ser Asp Tyr Ser Asp Pro Val Lys Thr Leu Gly
465                 470                 475                 480
Glu Gly Leu Ser Glu Arg Thr Val Glu Ile Ile Leu Ser Val Thr Leu
                485                 490                 495
Cys Ile Leu Ser Ile Ile Leu Leu Gly Thr Ala Ile Phe Ala Phe Ala
            500                 505                 510
Arg Ile Arg Gln Lys Gln Lys Glu Gly Gly Thr Tyr Ser Pro Gln Asp
        515                 520                 525
Ala Glu Ile Ile Asp Thr Lys Leu Lys Leu Asp Gln Leu Ile Thr Val
    530                 535                 540
Ala Asp Leu Glu Leu Lys Asp Glu Arg Leu Thr Arg Tyr Ser Ser Phe
545                 550                 555                 560
Phe Phe Arg Arg Lys Glu Ile Phe Val Ile Gln Leu Leu Ser Tyr Arg
                565                 570                 575
Lys Ser Ile Lys Pro Ile Ser Lys Ser Phe Leu Gln His Val Glu
            580                 585                 590
Glu Leu Cys Thr Asn Asn Leu Lys Phe Gln Glu Glu Phe Ser Glu
        595                 600                 605
Leu Pro Lys Phe Leu Gln Asp Leu Ser Ser Thr Asp Ala Asp Leu Pro
    610                 615                 620
Trp Asn Arg Ala Lys Asn Arg Phe Pro Asn Ile Lys Pro Tyr Asn Asn
625                 630                 635                 640
Asn Arg Val Lys Leu Ile Ala Asp Ala Ser Val Pro Gly Ser Asp Tyr
                645                 650                 655
Ile Asn Ala Ser Tyr Ile Ser Gly Tyr Leu Cys Pro Asn Glu Phe Ile
            660                 665                 670
Ala Thr Gln Gly Pro Leu Pro Gly Thr Val Gly Asp Phe Trp Arg Met
        675                 680                 685
Val Trp Glu Thr Arg Ala Lys Thr Leu Val Met Leu Thr Gln Cys Phe
    690                 695                 700
Glu Lys Gly Arg Ile Arg Cys His Gln Tyr Trp Pro Glu Asp Asn Lys
705                 710                 715                 720
Pro Val Thr Val Phe Gly Asp Ile Val Ile Thr Lys Leu Met Glu Asp
                725                 730                 735
```

-continued

Val Gln Ile Asp Trp Thr Ile Arg Asp Leu Lys Ile Glu Arg His Gly
                740                 745                 750

Asp Cys Met Thr Val Arg Gln Cys Asn Phe Thr Ala Trp Pro Glu His
            755                 760                 765

Gly Val Pro Glu Asn Ser Ala Pro Leu Ile His Phe Val Lys Leu Val
        770                 775                 780

Arg Ala Ser Arg Ala His Asp Thr Thr Pro Met Ile Val His Cys Ser
785                 790                 795                 800

Ala Gly Val Gly Arg Thr Gly Val Phe Ile Ala Leu Asp His Leu Thr
                805                 810                 815

Gln His Ile Asn Asp His Asp Phe Val Asp Ile Tyr Gly Leu Val Ala
                820                 825                 830

Glu Leu Arg Ser Glu Arg Met Cys Met Val Gln Asn Leu Ala Gln Tyr
                835                 840                 845

Ile Phe Leu His Gln Cys Ile Leu Asp Leu Leu Ser Asn Lys Gly Ser
850                 855                 860

Asn Gln Pro Ile Cys Phe Val Asn Tyr Ser Ala Leu Gln Lys Met Asp
865                 870                 875                 880

Ser Leu Asp Ala Met Glu Gly Asp Val Glu Leu Glu Trp Glu Glu Thr
                885                 890                 895

Thr Met

<210> SEQ ID NO 23
<211> LENGTH: 41
<212> TYPE: PRT
<213> ORGANISM: Homo sapiens

<400> SEQUENCE: 23

Gln Lys Gln Glu Trp Ile Cys Leu Glu Thr Leu Thr Pro Asp Thr Gln
1               5                   10                  15

Tyr Glu Phe Gln Val Arg Val Lys Pro Leu Gln Gly Glu Phe Thr Thr
            20                  25                  30

Trp Ser Pro Trp Ser Gln Pro Leu Ala
        35                  40

<210> SEQ ID NO 24
<211> LENGTH: 92
<212> TYPE: PRT
<213> ORGANISM: Homo sapiens

<400> SEQUENCE: 24

Leu Ser Pro Pro Thr Asn Leu His Leu Glu Ala Asn Pro Asp Thr Gly
1               5                   10                  15

Val Leu Thr Val Ser Trp Glu Arg Ser Thr Thr Pro Asp Ile Thr Gly
            20                  25                  30

Tyr Arg Ile Thr Thr Thr Pro Thr Asn Gly Gln Gln Gly Asn Ser Leu
        35                  40                  45

Glu Glu Val Val His Ala Asp Gln Ser Ser Cys Thr Phe Asp Asn Leu
    50                  55                  60

Ser Pro Gly Leu Glu Tyr Asn Val Ser Val Tyr Thr Val Lys Asp Asp
65                  70                  75                  80

Lys Glu Ser Val Pro Ile Ser Asp Thr Ile Ile Pro
                85                  90

```
<210> SEQ ID NO 25
<211> LENGTH: 98
<212> TYPE: PRT
<213> ORGANISM: Homo sapiens

<400> SEQUENCE: 25

Met Arg Gly Leu Lys Pro Trp Thr Gln Tyr Ala Ile Phe Val Lys Thr
 1               5                  10                  15

Leu Val Thr Phe Ser Asp Glu Arg Arg Thr Tyr Gly Ala Lys Ser Asp
                20                  25                  30

Ile Ile Tyr Val Gln Thr Asp Ala Thr Asn Pro Ser Val Pro Leu Asp
            35                  40                  45

Pro Ile Ser Val Ser Asn Ser Ser Gln Ile Ile Leu Lys Trp Lys
     50                  55                  60

Pro Pro Ser Asp Pro Asn Gly Asn Ile Thr His Tyr Leu Val Phe Trp
 65                  70                  75                  80

Glu Arg Gln Ala Glu Asp Ser Glu Leu Phe Glu Leu Asp Tyr Cys Leu
                85                  90                  95

Lys Gly

<210> SEQ ID NO 26
<211> LENGTH: 99
<212> TYPE: PRT
<213> ORGANISM: Homo sapiens

<400> SEQUENCE: 26

Leu His Gly Leu Lys Pro Trp Thr Gln Tyr Ala Val Tyr Val Lys Ala
 1               5                  10                  15

Val Thr Leu Thr Met Val Glu Asn Asp His Ile Arg Gly Ala Lys Ser
                20                  25                  30

Glu Ile Leu Tyr Ile Arg Thr Asn Ala Ser Val Pro Ser Ile Pro Leu
            35                  40                  45

Asp Val Leu Ser Ala Ser Asn Ser Ser Gln Leu Ile Val Lys Trp
     50                  55                  60

Asn Pro Pro Ser Leu Pro Asn Gly Asn Leu Ser Tyr Tyr Ile Val Arg
 65                  70                  75                  80

Trp Gln Arg Gln Pro Gln Asp Gly Tyr Leu Tyr Arg His Asn Tyr Cys
                85                  90                  95

Ser Lys Asp

<210> SEQ ID NO 27
<211> LENGTH: 99
<212> TYPE: PRT
<213> ORGANISM: Homo sapiens

<400> SEQUENCE: 27

Leu Ala Ser Leu Lys Pro Trp Thr Gln Tyr Ala Val Phe Val Arg Ala
 1               5                  10                  15

Ile Thr Leu Thr Thr Glu Glu Asp Ser Pro His Gln Gly Ala Gln Ser
                20                  25                  30

Pro Ile Val Tyr Leu Arg Thr Leu Pro Ala Ala Pro Thr Val Pro Gln
            35                  40                  45

Asp Val Ile Ser Thr Ser Asn Ser Ser Ser His Leu Leu Val Arg Trp
 50                  55                  60

Lys Pro Pro Thr Gln Arg Asn Gly Asn Leu Thr Tyr Tyr Leu Val Leu
 65                  70                  75                  80
```

Trp Gln Arg Leu Ala Glu Asp Gly Asp Leu Tyr Leu Asn Asp Tyr Cys
            85                  90                  95
His Arg Gly

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: modified_base
<222> LOCATION: (17)
<223> OTHER INFORMATION: a, t, c, g, other or unknown

<400> SEQUENCE: 28
ayttytggvr ratgrtntgg                                              20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: modified_base
<222> LOCATION: (3)
<223> OTHER INFORMATION: a, t, c, g, other or unknown

<400> SEQUENCE: 29
ccnaydcchg crctrcagtg                                              20

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (3)..(4)
<223> OTHER INFORMATION: Variable amino acid

<400> SEQUENCE: 30

Arg Cys Xaa Xaa Tyr Trp Pro
 1               5

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
ccatcagtat tggccagagg                                              20

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (4)
<223> OTHER INFORMATION: Variable amino acid
<221> NAME/KEY: MOD_RES

```
<222> LOCATION: (6)
<223> OTHER INFORMATION: Variable amino acid
<221> NAME/KEY: MOD_RES
<222> LOCATION: (9)
<223> OTHER INFORMATION: Variable amino acid

<400> SEQUENCE: 32

His Cys Ser Xaa Gly Xaa Gly Arg Xaa Gly
 1               5                   10

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
gacggatccg atgccatcag tattgg                                26

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
tggtctagat atttacatag tggtt                                 25

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
ccatcagtat tggccagagg                                       20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
caagctcaac atcaccttcc a                                     21

<210> SEQ ID NO 37
<211> LENGTH: 32
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
cgggatccat catgagaatg aggccaataa gc                         32

<210> SEQ ID NO 38
<211> LENGTH: 30
```

-continued

```
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 38
gctctagagc ttgtaatcac tatatctcca                                      30

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
gatctccgaa ttccatggat ccaggcctct agaagcttac                           40

<210> SEQ ID NO 40
<211> LENGTH: 40
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
aggcttaagg tacctaggtc cggagatctt cgaatgttaa                           40

<210> SEQ ID NO 41
<211> LENGTH: 7
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (6)
<223> OTHER INFORMATION: Ser, Ile or Val

<400> SEQUENCE: 41

His Cys Ser Ala Gly Xaa Gly
  1               5

<210> SEQ ID NO 42
<211> LENGTH: 6
<212> TYPE: PRT
<213> ORGANISM: Artificial Sequence
<220> FEATURE:
<223> OTHER INFORMATION: Description of Artificial Sequence: PTP-S31

<400> SEQUENCE: 42

His Gln Tyr Trp Pro Glu
  1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: peptide
      coded from the 5' end of PTP domain
<221> NAME/KEY: MOD_RES
<222> LOCATION: (2)
```

```
<223> OTHER INFORMATION: Lys or Arg
<221> NAME/KEY: MOD_RES
<222> LOCATION: (3)..(5)
<223> OTHER INFORMATION: Variable amino acid

<400> SEQUENCE: 43

Asn Xaa Xaa Xaa Xaa Asn Arg
  1               5

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: C-terminal
      part of PTP domain
<221> NAME/KEY: MOD_RES
<222> LOCATION: (5)..(10)
<223> OTHER INFORMATION: Variable amino acid

<400> SEQUENCE: 44

Gln Tyr Ile Phe Xaa Xaa Xaa Xaa Xaa Xaa Asp
  1               5                  10

<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: PTP S31D
<221> NAME/KEY: MOD_RES
<222> LOCATION: (4)
<223> OTHER INFORMATION: Variable amino acid
<221> NAME/KEY: MOD_RES
<222> LOCATION: (6)
<223> OTHER INFORMATION: Variable amino acid

<400> SEQUENCE: 45

His Cys Ser Xaa Gly Xaa Gly Arg
  1               5

<210> SEQ ID NO 46
<211> LENGTH: 6
<212> TYPE: PRT
<213> ORGANISM: Artificial Sequence
<220> FEATURE:
<223> OTHER INFORMATION: Description of Artificial Sequence: Consensus
      sequence
<221> NAME/KEY: MOD_RES
<222> LOCATION: (3)
<223> OTHER INFORMATION: Variable amino acid
<221> NAME/KEY: MOD_RES
<222> LOCATION: (5)
<223> OTHER INFORMATION: Variable amino acid

<400> SEQUENCE: 46

Phe Trp Xaa Met Xaa Trp
  1               5

<210> SEQ ID NO 47
<211> LENGTH: 289
<212> TYPE: PRT
<213> ORGANISM: Artificial Sequence
<220> FEATURE:
<223> OTHER INFORMATION: Description of Artificial Sequence: PTP-S31D

<400> SEQUENCE: 47

Met Arg Met Arg Pro Ile Ser Lys Lys Ser Phe Leu Gln His Val Glu
  1               5                  10                  15
```

-continued

```
Glu Leu Cys Thr Asn Asn Asn Leu Lys Phe Gln Glu Glu Phe Ser Glu
         20                  25                  30

Leu Pro Lys Phe Leu Gln Asp Leu Ser Ser Thr Asp Ala Asp Leu Pro
         35                  40                  45

Trp Asn Arg Ala Lys Asn Arg Phe Pro Asn Ile Lys Pro Tyr Asn Asn
     50                  55                  60

Asn Arg Val Lys Leu Ile Ala Asp Ala Ser Val Pro Gly Ser Asp Tyr
 65                  70                  75                  80

Ile Asn Ala Ser Tyr Ile Ser Gly Tyr Leu Cys Pro Asn Glu Phe Ile
                 85                  90                  95

Ala Thr Gln Gly Pro Leu Pro Gly Thr Val Gly Asp Phe Trp Arg Met
                100                 105                 110

Val Trp Glu Thr Arg Ala Lys Thr Leu Val Met Leu Thr Gln Cys Phe
            115                 120                 125

Glu Lys Gly Arg Ile Arg Cys His Gln Tyr Trp Pro Glu Asp Asn Lys
        130                 135                 140

Pro Val Thr Val Phe Gly Asp Ile Val Ile Thr Lys Leu Met Glu Asp
145                 150                 155                 160

Val Gln Ile Asp Trp Thr Ile Arg Asp Leu Lys Ile Glu Arg His Gly
                165                 170                 175

Asp Cys Met Thr Val Arg Gln Cys Asn Phe Thr Ala Trp Pro Glu His
                180                 185                 190

Gly Val Pro Glu Asn Ser Ala Pro Leu Ile His Phe Val Lys Leu Val
            195                 200                 205

Arg Ala Ser Arg Ala His Asp Thr Thr Pro Met Ile Val His Cys Ser
    210                 215                 220

Ala Gly Val Gly Arg Thr Gly Val Phe Ile Ala Leu Asp His Leu Thr
225                 230                 235                 240

Gln His Ile Asn Asp His Asp Phe Val Asp Ile Tyr Gly Leu Val Ala
                245                 250                 255

Glu Leu Arg Ser Glu Arg Met Cys Met Val Gln Asn Leu Ala Gln Tyr
            260                 265                 270

Ile Phe Leu His Gln Cys Ile Leu Asp Leu Leu Ser Asn Lys Gly Ser
        275                 280                 285

Asn
```

```
<210> SEQ ID NO 48
<211> LENGTH: 40
<212> TYPE: PRT
<213> ORGANISM: Artificial Sequence
<220> FEATURE:
<223> OTHER INFORMATION: Description of Artificial Sequence: PTP-S31

<400> SEQUENCE: 48
```

```
Gly Asn Glu Asp Lys Ile Cys Asn Gly Pro Leu Lys Pro Lys Lys Gln
 1               5                  10                  15

Tyr Leu Phe Lys Phe Arg Ala Thr Asn Ile Met Gly Gln Phe Thr Asp
             20                  25                  30

Ser Asp Tyr Ser Asp Pro Val Lys
         35                  40
```

```
<210> SEQ ID NO 49
<211> LENGTH: 106
<212> TYPE: PRT
<213> ORGANISM: Artificial Sequence
<220> FEATURE:
<223> OTHER INFORMATION: Description of Artificial Sequence: S31-FN-4
```

```
<400> SEQUENCE: 49

Pro Ser Val Pro Thr Asn Ile Ala Phe Ser Asp Val Gln Ser Thr Ser
  1               5                  10                  15

Ala Thr Leu Thr Trp Ile Arg Pro Asp Thr Ile Leu Gly Tyr Phe Gln
             20                  25                  30

Asn Tyr Lys Ile Thr Thr Gln Leu Arg Ala Gln Lys Cys Lys Glu Trp
         35                  40                  45

Glu Ser Glu Glu Cys Val Glu Tyr Gln Lys Ile Gln Tyr Leu Tyr Glu
     50                  55                  60

Ala His Leu Thr Glu Glu Thr Val Tyr Gly Leu Lys Lys Phe Arg Trp
 65                  70                  75                  80

Tyr Arg Phe Gln Val Ala Ala Ser Thr Asn Ala Gly Tyr Gly Asn Ala
                 85                  90                  95

Ser Asn Trp Ile Ser Thr Lys Thr Leu Pro
            100                 105

<210> SEQ ID NO 50
<211> LENGTH: 104
<212> TYPE: PRT
<213> ORGANISM: Artificial Sequence
<220> FEATURE:
<223> OTHER INFORMATION: Description of Artificial Sequence: S31-FN-3

<400> SEQUENCE: 50

Gly Pro Pro Asp Gly Pro Pro Glu Asn Val His Val Val Ala Thr Ser
  1               5                  10                  15

Pro Phe Ser Ile Ser Ile Ser Trp Ser Glu Pro Ala Val Ile Thr Gly
             20                  25                  30

Pro Thr Cys Tyr Leu Ile Asp Val Lys Ser Val Asp Asn Asp Glu Phe
         35                  40                  45

Asn Ile Ser Phe Ile Lys Ser Asn Glu Glu Asn Lys Thr Ile Glu Ile
     50                  55                  60

Lys Asp Leu Glu Ile Phe Thr Arg Tyr Ser Val Val Ile Thr Ala Phe
 65                  70                  75                  80

Thr Gly Asn Ile Ser Ala Ala Tyr Val Glu Gly Lys Ser Ser Ala Glu
                 85                  90                  95

Met Ile Val Thr Thr Leu Glu Ser
            100

<210> SEQ ID NO 51
<211> LENGTH: 115
<212> TYPE: PRT
<213> ORGANISM: Artificial Sequence
<220> FEATURE:
<223> OTHER INFORMATION: Description of Artificial Sequence: S31-FN-2

<400> SEQUENCE: 51

Ala Pro Lys Asp Pro Asn Asn Met Thr Phe Gln Lys Ile Pro Asp
  1               5                  10                  15

Glu Val Thr Lys Phe Gln Leu Thr Phe Leu Pro Pro Ser Gln Pro Asn
             20                  25                  30

Gly Asn Ile Gln Val Tyr Gln Ala Leu Val Tyr Arg Glu Asp Asp Pro
         35                  40                  45

Thr Ala Val Gln Ile His Asn Leu Ser Ile Ile Gln Lys Thr Asn Thr
     50                  55                  60
```

```
Phe Val Ile Ala Met Leu Glu Gly Leu Lys Gly Gly His Thr Tyr Asn
 65                  70                  75                  80

Ile Ser Val Tyr Ala Val Asn Ser Ala Gly Ala Gly Pro Lys Val Pro
                 85                  90                  95

Met Arg Ile Thr Met Asp Ile Lys Ala Pro Ala Arg Pro Lys Thr Lys
            100                 105                 110

Pro Thr Pro
        115

<210> SEQ ID NO 52
<211> LENGTH: 122
<212> TYPE: PRT
<213> ORGANISM: Artificial Sequence
<220> FEATURE:
<223> OTHER INFORMATION: Description of Artificial Sequence: S31-FN-1

<400> SEQUENCE: 52

Pro Ile Lys Asn Val Gln Val Leu Val Thr Glu Thr Gly Ala Gln His
  1               5                  10                  15

Asp Gly Asn Val Thr Lys Trp Tyr Asp Ala Tyr Phe Asn Lys Ala Arg
                 20                  25                  30

Pro Tyr Phe Thr Asn Glu Gly Phe Pro Asn Pro Pro Cys Thr Glu Gly
             35                  40                  45

Lys Thr Lys Phe Ser Gly Asn Glu Glu Ile Tyr Ile Gly Ala Asp
     50                  55                  60

Asn Ala Cys Met Ile Pro Gly Asn Glu Asp Lys Ile Cys Asn Gly Pro
 65                  70                  75                  80

Leu Lys Pro Lys Lys Gln Tyr Leu Phe Lys Phe Arg Ala Thr Asn Ile
                 85                  90                  95

Met Gly Gln Phe Thr Asp Ser Asp Tyr Ser Asp Pro Val Lys Thr Leu
            100                 105                 110

Gly Glu Gly Leu Ser Glu Arg Thr Val Glu
            115                 120

<210> SEQ ID NO 53
<211> LENGTH: 103
<212> TYPE: PRT
<213> ORGANISM: Artificial Sequence
<220> FEATURE:
<223> OTHER INFORMATION: Description of Artificial Sequence: PTPS31

<400> SEQUENCE: 53

Ile Lys Asp Leu Glu Ile Phe Thr Arg Tyr Ser Val Val Ile Thr Ala
  1               5                  10                  15

Phe Thr Gly Asn Ile Ser Ala Ala Tyr Val Glu Gly Lys Ser Ser Ala
                 20                  25                  30

Glu Met Ile Val Thr Thr Leu Glu Ser Ala Pro Lys Gly Pro Pro Asn
             35                  40                  45

Asn Met Thr Phe Gln Lys Ile Pro Asp Glu Val Thr Lys Phe Gln Leu
         50                  55                  60

Thr Phe Leu Pro Pro Ser Gln Pro Asn Gly Asn Ile Gln Val Tyr Gln
 65                  70                  75                  80

Ala Leu Val Tyr Arg Glu Asp Asp Pro Thr Ala Val Gln Ile His Asn
                 85                  90                  95

Leu Ser Ile Ile Gln Lys Thr
            100
```

What is claimed is:

1. An isolated antibody or an antigen-binding fragment thereof specific for a human protein tyrosine phosphatase (PTP-S31) protein or glycoprotein molecule comprising an antibody or an antigen-binding fragment thereof specific for a human PTP-S31 protein or glycoprotein molecule selected from the group consisting of PTP-S31 (SEQ ID NO:7), PTPS31D (SEQ ID NO:11), PTPS31D-63 (SEQ ID NO:15), PTPS31-14 (SEQ ID NO:16), PTPS31-2 (SEQ ID NO:17), PTPS31-5 (SEQ ID NO:18), PTPS31-63 (SEQ ID NO:19), PTPS31-III (SEQ ID NO:20) and PTPS31-RD#2 (SEQ ID NO:22).

2. An antibody or a fragment thereof according to claim 1, wherein said antibody is a monoclonal antibody.

3. An antibody or a fragment thereof according according to claim 1, wherein said molecule comprises the amino acid sequence SEQ ID NO:7.

4. An antibody or an antibody fragment thereof according to claim 1, wherein said molecule is selected from the group consisting of PTP-S31 (SEQ ID NO:11), PTPS31D-63 (SEQ ID NO:15), PTPS31-14 (SEQ ID NO:16), PTPS31-2 (SEQ ID NO:17), PTPS31-5 (SEQ ID NO:18), PTPS31-63 (SEQ ID NO:19), PTPS31-III (SEQ ID NO:20) and PTPS31-RD#2 (SEQ ID NO:22).

5. An antibody or a fragment thereof according to claim 3, wherein said antibody is a monoclonal antibody.

6. An antibody or a fragment thereof according to claim 4, wherein said antibody is a monoclonal antibody.

7. A cell producing the antibody or a fragment thereof of claim 1.

8. A cell producing the antibody or a fragment thereof of claim 3.

9. A cell producing the antibody or a fragment thereof of claim 4.

* * * * *